Figure 1:
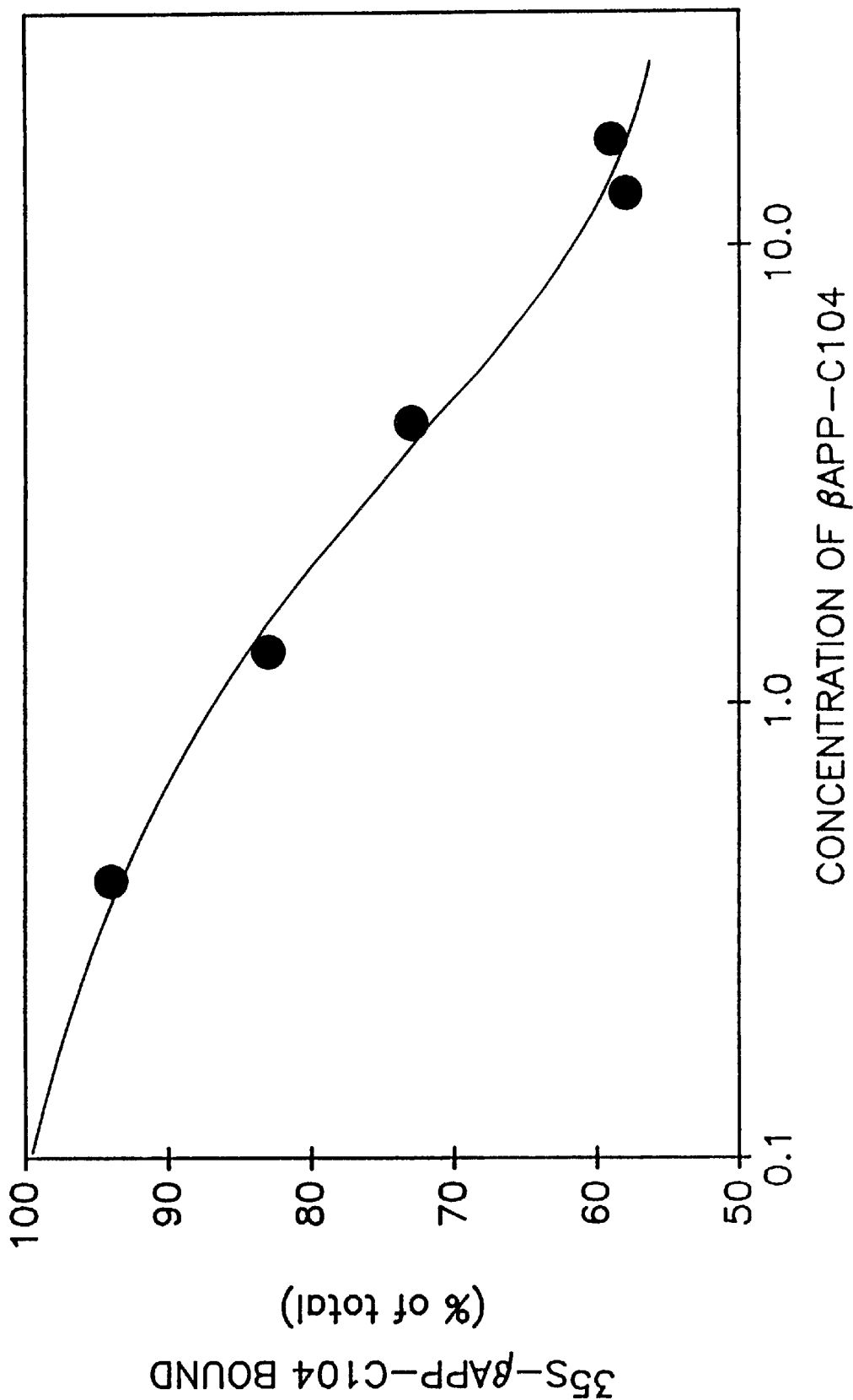

United States Patent [19]
Manly et al.

[11] Patent Number: 6,083,713
[45] Date of Patent: Jul. 4, 2000

[54] CLONING AND EXPRESSION OF βAPP-C100 RECEPTOR (C100-R)

[75] Inventors: Susan P. Manly, Wallingford, Conn.; Michael R. Kozlowski, Palo Alto, Calif.; Rachael L. Neve, Belmont, Mass.

[73] Assignees: Bristol-Myers Squibb Company, New York, N.Y.; McLean Hospital Corporation, Belmont, Mass.

[21] Appl. No.: 08/559,397

[22] Filed: Nov. 15, 1995

Related U.S. Application Data

[63] Continuation-in-part of application No. 08/114,555, Aug. 30, 1993, Pat. No. 5,854,392, and a continuation-in-part of application No. 07/938,184, Aug. 31, 1992, abandoned.

[51] Int. Cl.[7] ............................ C12N 15/12; C12N 15/70; C12N 15/85
[52] U.S. Cl. ........................ 435/69.1; 435/69.7; 435/325; 435/252.3; 435/320.1; 536/23.1; 536/23.4; 536/23.5
[58] Field of Search .................................. 536/23.1, 23.4, 536/23.5; 435/69.1, 320.1, 325, 252.3, 69.7

[56] References Cited

PUBLICATIONS

Leberer et al. The EMBO Journal 11 (1992) 4815–4824.

Rudinger In "Peptide Hormones" (Jun. 1976) ed. J.A. Parsons, University Park Press, Baltimore, pp. 1–7.

*Primary Examiner*—Anthony C. Caputa
*Assistant Examiner*—Robert C. Hayes
*Attorney, Agent, or Firm*—Pennie & Edmonds LLP

[57] ABSTRACT

The present invention relates to the cloning of βAPP-C100 receptor (C100-R), and genetically engineered host cells which express the C100-R. Such engineered cells may be used to evaluate and screen drugs and analogs of β-APP involved in Alzheimer's Disease.

12 Claims, 32 Drawing Sheets

```
CCC CCT CGA GGT CGA CTC CTG GAG CCC GTC AGT ATC GGC GGA ATT     45
 P   P   R   G   R   L   L   E   P   V   S   I   G   G   I

CCT GAA CAA TGG GCT CGA CTG CTC CAA ACC TCC AAC ATT ACA AAA     90
 P   E   Q   W   A   R   L   L   Q   T   S   N   I   T   K

CTG GAA CAG AAG AAG AAC CCA CAG GCT GTT CTG GAT GTT CTC GAG    135
 L   E   Q   K   K   N   P   Q   A   V   L   D   V   L   E

TTT TAC GAC TCC AAA GAA ACA GTC AAC AAC CAG AAA TAC ATG AGC    180
 F   Y   D   S   K   E   T   V   N   N   Q   K   Y   M   S

TTT ACA TCA GGA GAT AAA AGT GCC CAT GGA TAT ATA GCA GCA CAT    225
 F   T   S   G   D   K   S   A   H   G   Y   I   A   A   H

CAG TCG AAT ACC AAA ACA GCT TCA GAA CCT CCT TTG GCT CCT CCT    270
 Q   S   N   T   K   T   A   S   E   P   P   L   A   P   P

GTA TCT GAA GAA GAG GAT GAA GAA GAG GAA GAG GAA GAA GAT GAT    315
 V   S   E   E   E   D   E   E   E   E   E   E   E   D   D

AAT GAG CCC CCG CCT GTC ATT GCA CCA AGA CCA GAG CAT ACA AAA    360
 N   E   P   P   P   V   I   A   P   R   P   E   H   T   K

TCA ATC TAT ACT CGT TCT GTG GTT GAG TCA ATT GCT TCA CCA GCA    405
 S   I   Y   T   R   S   V   V   E   S   I   A   S   P   A

GCA CCA AAT AAA GAA GCC ACC CCA CCT TCT GCT GAG AAT GCC AAT    450
 A   P   N   K   E   A   T   P   P   S   A   E   N   A   N

TCC AGT ACT TTG TAC AGG AAT ACA GAT CGG CAA AGA AAA AAA TCC    495
 S   S   T   L   Y   R   N   T   D   R   Q   R   K   K   S

AAG ATG ACA GAT GAG GAG ATC CTA GAG AAG CTA AGA AGC ATT GTG    540
 K   M   T   D   E   E   I   L   E   K   L   R   S   I   V

AGT GTT GGG GAC CCA AAG AAG AAA TAT ACA AGA TTT GAA AAA ATT    585
 S   V   G   D   P   K   K   K   Y   T   R   F   E   K   I

GGC CAA GGG GCA TCA GGA ACT GTT TAC ACA GCA CTA GAC ATT GCG    630
 G   Q   G   A   S   G   T   V   Y   T   A   L   D   I   A

ACA GGA CAA GAG GTG GCT ATA AAG CAA ATG AAC CTT CAA CAG CAG    675
 T   G   Q   E   V   A   I   K   Q   M   N   L   Q   Q   Q
```

FIG.4A

```
CCC AAA AAG GAA TTA ATT ATT AAT GAA ATT CTT GTC ATG AGG GAA    720
 P   K   K   E   L   I   I   N   E   I   L   V   M   R   E

AAT AAG AAC CCC AAT ATT GTC AAT TAT TTA GAT AGC TAC TTA GTG    765
 N   K   N   P   N   I   V   N   Y   L   D   S   Y   L   V

GGT GAT GAA CTG TGG GTA GTC ATG GAA TAC TTG GCT GGT GGC TCT    810
 G   D   E   L   W   V   V   M   E   Y   L   A   G   G   S

TTG ACT GAC GTG GTC ACA GAA ACC TGT ATG GAT GAA GGA CAG ATA    855
 L   T   D   V   V   T   E   T   C   M   D   E   G   Q   I

GCA GCC GTC TGT AGA GAG TGC CTC CAA GCT TTG GAT TTC TTG CAC    900
 A   A   V   C   R   E   C   L   Q   A   L   D   F   L   H

TCA AAA CAA GTG ATC CAC AGA GAT ATA AAG AGT GAC AAT ATT CTC    945
 S   K   Q   V   I   H   R   D   I   K   S   D   N   I   L

CTC GGG ATG GAT GGT TCT GTT AAA CTG ACT GAT TTT GGA TTC TGT    990
 L   G   M   D   G   S   V   K   L   T   D   F   G   F   C

GCC CAA ATC ACT CCT GAG CAA AGT AAA CGA AGC ACT ATG GTG GGA   1035
 A   Q   I   T   P   E   Q   S   K   R   S   T   M   V   G

ACT CCC TAT TGG ATG GCA CCT GAG GTG GTA ACT CGA AAA GCT TAT   1080
 T   P   Y   W   M   A   P   E   V   V   T   R   K   A   Y

GGC CCG AAA GTT GAT ATC TGG TCT CTG GGA ATC ATG GCC ATT GAA   1125
 G   P   K   V   D   I   W   S   L   G   I   M   A   I   E

ATG GTG GAA GGT GAA CCC CCT TAC CTT AAT GAA AAT CCA CTC AGG   1170
 M   V   E   G   E   P   P   Y   L   N   E   N   P   L   R

GCC TTA TAT CTG ATA GCC ACT AAT GGA ACC CCA GAG CTC CAG AAT   1215
 A   L   Y   L   I   A   T   N   G   T   P   E   L   Q   N

CCC GAG AGA CTG TCA GCT GTA TTC CGT GAC TTC TTA AAT CGC TGT   1260
 P   E   R   L   S   A   V   F   R   D   F   L   N   R   C

CTT GAG ATG GAT GTC GAT AGA CGA GGG TCT GCC AAG GAG CTT TTG   1305
 L   E   M   D   V   D   R   R   G   S   A   K   E   L   L

CAG CAT CCA TTT TTA AAA TTA GCC AAG CCC CTG TCC AGC CTC ACT   1350
 Q   H   P   F   L   K   L   A   K   P   L   S   S   L   T
```

FIG.4B

```
CCT CTG ATT CTT GCT GCA AAG GAA GCC ATT AAG AAC AGT AGC CGT   1395
 P   L   I   L   A   A   K   E   A   I   K   N   S   S   R

TAG AAG TGC AAG CCT TAC CCC TCA CCG TCT CCC GGA TGA GTA AGA   1440
 *

CTG AAC TAA AAC TCT GCT GCA GGA TCC ACA GAA GAA AAG ACA GTC   1485

AAA TGG AGT GGG GGT TCT TTA ACT TTC AAG TGA ATA GAA ACT TCT   1530

TAT AAA CCT TTT TCC TAC TCC CTC AGA TTA TGT AAT TTA TTT GTA   1575

AGC TGA ACG CAG CCC ACA CAG GCA GCA ATG TCG AAG TAG CCA   1620

TTA AGT GGC CAC TTC CAC CGT GAA GCG AGA GAG CCA GTA GTG AAT   1665

CCC CTC ATT CGT GCA TTT ACT TTG AAG AAA AAG AGA TTT CTC AAA   1710

GAT GCA CAC TCC CTC TTC ATA GTG CTG TGT GTT TTT AAG TTA GAG   1755

AGT AGT CCC CCT TCC ATT CAA ACC TCT TTC AAA ATC CCT TAC CCA   1800

ACG TGA TGT TTT TTC ACT TGC ATT GTC ATT AGA TGT CCA GAA AAA   1845

AAG ATG TCA AAA TGT TTT TTT TAA AAA AAA GAA AGC AAA AAA GCA   1890

AAG AAA AAA GGA ATT CCA GCT GAG CGC CGG TCG CTA CCA TTA CCA   1935

GTT GGT CTG GTC TCA AGC GGC CGC CAC CGC GGT GGA                1971
```

FIG.4C

RATBCCAIS RAT CALCIUM CHANNEL ALPHA-1 SUBUNIT mRNA, co 112  71  71
76.7% IDENTITY IN 30 nt OVERLAP

```
               460       470       480       490       500       510
l7.dom  CAGGAATACAGATCGGCAAAGAAAAAAATCCAAGATGACAGATGAGGAGATCCTAGAGAA
                                  X::::::::   ::  ::   : :  ::::::::::X
RATBCC  GATCATCATCACCTTCCAGGAGCAGGGAGACAAGATGATGGAAGAATACAGCCTAGAGAA
              4380      4390      4400      4410      4420      4430

520       530       540       550       560       570
l7.dom  GCTAAGAACATTGTGNGTGTTGGGGACCCAAAGAAGANNNTATACAAGATTTGAAAAAAT RATBCC  AAATGAGAGGGCCTGCATCGACTTTGCCATCAGTGCCAAGCCGCTGACCAGGCACATGCC
              4440      4450      4460      4470      4480      4490
```

FIG.5A

MUSCRP55 MOUSE mRNA FOR CALRETICULIN
78.0% IDENTITY IN 50 nt OVERLAP

```
               250       260       270       280       290       300
l7.dom  TTCAGAACCTCCTTTGGCTCCTCCTGTATCTGAAGAAGAGGATGAAGAAGAGGAAGAGGA
                               X:::::  :::::  ::::::::::  ::    ::::
MUSCRP  TGAGGATAAAGAGGATGATGATGACAGAGATGAAGATGAGGACGAAGAAGATGAGAAGGA
              1220      1230      1240      1250      1260      1270

310       320       330       340       350       360
l7.dom  AGAAGATGATAATGAGCCCCGCCTGTCATTGCACCAAGACCAGAGCATACAAAATAATCT
        ::::::::::X  :  ::  :::
MUSCRP  GGAAGATGAGGAAGAATCCCCTGGCCAAGCCAAGGATGAGCTGTAGAGGCCACACCACCT
              1280      1290      1300      1310      1320      1330
```

RATCALRET RAT mRNA FOR CALRETICULIN
77.6% IDENTITY IN 49 nt OVERLAP

```
               250       260       270       280       290       300
l7.dom  TTCAGAACCTCCTTTGGCTCCTCCTGTATCTGAAGAAGAGGATGAAGAAGAGGAAGAGGA
                               X:::::  ::  :::::::::  ::  ::   ::::
RATCAL  CGAGGATAAAGAGGATGAGGATGACAGAGATGAAGATGAAGATGAAGAGGATGAGAAGGA
                  1190      1200      1210      1220      1230      1240

310       320       330       340       350       360
l7.dom  AGAAGATGATAATGAGCCCCGCCTGTCATTGCACCAAGACCAGAGCATACAAAATAATCT
        ::::::::::X  :  ::  ::
RATCAL  AGAAGATGAGGAGGATGCCACTGGCCAAGCCAAGGATGAGCTGTAGAGGCCACACCACCT
                  1250      1260      1270      1280      1290      1300
```

FIG.5B

A35041 - *RYANODINE RECEPTOR - HUMAN
   15.7% IDENTITY IN 178 aa OVERLAP

```
                                       10         20         30
l7lran                         PPRGRLLEPVSIGGIPEQWARLLQTSNITKL
                                  ..::  ..........  .:. ..  .
A35041   GVGVTTSLRPPHHFSPPCFVAALPAAGAAEAPARLSPAIPLEALRDKALRMLGEAVRDGG
             1770      1780      1790      1800      1810      1820

40        50        60        70        80        90
l7lran   EQKKNPQAVLDVLEFYDSKETVNNQKYMSFTSGDKSAHGYIAAHQSEYQTASEPPLAPPV
         .. ,.:  ..  ...:   . :..   :... ....  .    V.. . ...^  .
A35041   QHARDPVGASVEFQFVPVLKLVSTLLVMGIFGDEDVKQILKMIEPEVFTEEEEEEDEEEE
             1830      1840      1850      1860      1870      1880

100       110       120       130       140
l7lran   SEEEDEEEEEEEDDNEPRLSLHQDQSIQNNLYSSVVESIASPAAPNKEATHL-LLRCQ-F
         .::::::::::  ..       .V...... ..  . :..... . : .. :.. .
A35041   GEEEDEEEKEEDEEETAQEKEDEEKEEEEAAEGEKEEGLEEGLLQMKLPESVKLQMCHLL
             1890      1900      1910      1920      1930      1940

150       160       170       180       190       200
l7lran   QYF-DRNTDRQRKKSKMTDEEILEKLRTLPVLGTQRRFYTRFEKIGQGASGTVYTALDIA
         .::  :..  ...  ..   .:   ..:.::.
A35041   EYFCDQELQHRVESLAAFAERYVDKLQANQRSRYGLLIKAFSMTAAETARRTREFRSPPQ
             1950      1960      1970      1980      1990      2000
```

FIG.5C

```
HUMRYR  HUMAN RYANODINE RECEPTOR mRNA, COMPLETE cds.   113   79   87
 57.0% IDENTITY IN 135 nt OVERLAP
               250       260       270       280       290       300
t7.dam  TCAGAACCTCCTTTGGCTCCTCCTGTATCTGAAGAAGAGGATGAAGAAGAGGAAGAGGAA
                         :: X:::::::: : ::  :::   :   ::: ::
HUMRYR  ACAGCACAGGAAAAGGAAGATGAGGAAAAAGAGGAAGAGGAGGCAGCAGAAGGGGAGAAA
               5800      5810      5820      5830      5840      5850

310       320       330       340       350       360
t7.dam  GAAGATGATAATGAGCCCCGCCTGTCATTGCACCAAG--ACCAGAGCATACAAAATAATC
        ::::X :         :::       : :::  :       :  :::  :::::: :   :: :
HUMRYR  GAAGAAGGCTTGGAGGAAGGGCTG-CTCCAGATGAAGTTGCCAGAGTCTGTGAAGTTACA
               5860      5870      5880      5890      5900      5910

370       380       390       400       410       420
t7.dam  TATACTCGTCTGTGGTTGAGTCAATTGCT-TCACCAGCAGCACCAAATAAAGAAGCCACC
        ::      :     :: ::  ::::  ::: ::  :   ::::  :::   ::
HUMRYR  GATGTGCCAC-CTGCTGGAGT---ATTTCTGTGACCAAGAGCTGCAGCACCGTGTGGAGTC
               5920      5930      5940      5950      5960      5970

430       440       450       460       470       480
t7.dam  CACCTTCTGCTGAGATGCCCAATTCCAGTACTTTGACAGGAATACAGATCGGCAAAGAAAA HUMRYR  CCTGGCAGCCTTTGCGGAGCGCTATGTGGACAAGCTCCAGGCCAACCAGCGGAGCCGCTA
               5980      5990      6000      6010      6020      6030
```

FIG.5D

S04654 - RYANODINE RECEPTOR - RABBIT   63   63   9
15.7% IDENTITY IN 178 aa OVERLAP
                                              10         20         30
l7lran                         PPRGRLLEPVSIGGIPEQWARLLQTSNITKL
                               ....::  ..........  .::  ..  .
S04654  GVGVTTSLRPPHHFSPPCFVAALPAAGVAEAPARLSPAIPLEALRDKALRMLGEAVRDGG
         1770      1780      1790      1800      1810      1820

40         50         60         70         80         90
l7lran  EQKKNPQAVLDVLEFYDSKETVNNQKYMSFTSGDKSAHGYIAAHQSEYQTASEPPLAPPV
        ..  ...:    ...:    . :...   :... ....  .   V..  .  ...^  .
S04654  QHARDPVGGSVEFQFVPVLKLVSTLLVMGIFGDEDVKQILKMIEPEVFTEEEEEEEEEE
         1830      1840      1850      1860      1870      1880

100        110        120        130        140
l7lran  SEEEDEEEEEEEDDNEPRLSLHQDQSIQNNLYSSVVESIASPAAPNKEATHL-LLRCQ-F
        .:::.:: .::....:   . ...... ...  .. :....  V. :  ...^  .:.. .
S04654  EEEEEEEDEEEKEEDEEEEEKEDAEKEEEEAPEGEKEDLEEGLLQMKLPESVKLQMCNLL
         1890      1900      1910      1920      1930      1940

150        160        170        180        190        200
l7lran  QYF-DRNTDRQRKKSKMTDEEILEKLRTLPVLGTQRRFYTRFEKIGQGASGTVYTALDIA
         .::  :...  ...  ..   .:  ......
S04654  EYFCDQELQHRVESLAAFAERYVDKLQANQRSRYALLMRAFTMSAAETARRTREFRSPPQ
         1950      1960      1970      1980      1990      2000

FIG.5E

```
                                                     EcoRI
  1  CTGGTAATGG TAGCGACCGG CGCTCACGTG GAATTCGAGA CTGCTAGATT CGTCCCTGCC
     GACCATTACC ATCGCTGGCC GCGAGTGCAC CTTAAGCTCT GACGATCTAA GCAGGGACGG

61  AGCGTGCTCC GAGGTACTGG AAAGGTCTTG GCAGGGTGGC TGGACCCTTG GCAGGAGCTG
     TCGCACGAGG CTCCATGACC TTTCCAGAAC CGTCCCACCG ACCTGGGAAC CGTCCTCGAC

121  TGAAATCAGC TGCAACTGAA AATGTCTGAC AGCTTGGATA ACGAAGAAAA ACCTCCAGCT
     ACTTTAGTCG ACGTTGACTT TTACAGACTG TCGAACCTAT TGCTTCTTTT TGGAGGTCGA

181  CCCCCACTGA GGATGAACAG TAACAACCGA GATTCTTCAG CACTCAACCA CAGCTCCAAA
     GGGGGTGACT CCTACTTGTC ATTGTTGGCT CTAAGAAGTC GTGAGTTGGT GTCGAGGTTT

241  CCACTGCCCA TGCGCCCGGA AGAGAAGAAT AAGAAAGCCA GGCTTCGCTC TATCTTCCCA
     GGTGACGGGT ACGCGGGCCT TCTCTTCTTA TTCTTTCGGT CCGAAGCGAG ATAGAAGGGT

301  GGAGGAGGGG ATAAAACCAA TAAGAAGAAA GAGAAAGAAC GCCCAGAGAT CTCTCTTCCT
     CCTCCTCCCC TATTTTGGTT ATTCTTCTTT CTCTTTCTTG CGGGTCTCTA GAGAGAAGGA

EcoRI
361  TCAGACTTTG AGCATACGAT TCATGTGGGT TTTGATGCAG TCACCGGGGA ATTCACTCCA
     AGTCTGAAAC TCGTATGCTA AGTACACCCA AAACTACGTC AGTGGCCCCT TAAGTGAGGT

421  GATCTCTATG GCTCACAGAT GTGCCCAGGA AGCTCCAGAG GGAATTCCTG AACAATGGGC
     CTAGAGATAC CGAGTGTCTA CACGGGTCCT TCGAGGTCTC CCTTAAGGAC TTGTTACCCG

481  TCGACTGCTC CAAACCTCCA ACATTACAAA ACTGGAACAG AAGAAGAACC CACAGGCTGT
     AGCTGACGAG GTTTGGAGGT TGTAATGTTT TGACCTTGTC TTCTTCTTGG GTGTCCGACA

541  TCTGGATGTT CTCAAGTTTT ACGACTCCAA AGAAACAGTC AACAACCAGA AATACATGAG
     AGACCTACAA GAGTTCAAAA TGCTGAGGTT TCTTTGTCAG TTGTTGGTCT TTATGTACTC

601  CTTTACATCA GGAGATAAAA GTGCCCATGG ATATATAGCA GCACATCAGT CGAATACCAA
     GAAATGTAGT CCTCTATTTT CACGGGTACC TATATATCGT CGTGTAGTCA GCTTATGGTT

661  AACAGCTTCA GAACC
     TTGTCGAAGT CTTGG
```

FIG.9

```
  1 GAATTCACAC ATGATCTTCT GGGCTCCTCC AAAGGGCTGG CATTACTTTT CTAGCTCTAC
      N  S  H  M  I  F  W  A  P  P  K  G  W  H  Y  F  S  S  S
 61 CCTCTGTAGC ACTCTAAGCT CAGGTCGTCC TCCTCCTACC ACTGCTGCTG CTGTGATCGC
      T  L  C  S  T  L  S  S  G  R  P  P  P  T  A  A  A  V  I
121 CTATCCCCTC TCATCCTCCT TCCTCGCCAA TTTCTGCTCC TCCTCCCGCA TCCCGCTCCT
      A  Y  P  L  S  S  S  F  L  A  N  F  C  S  S  S  R  I  P  L
181 CCAGCAGCTA AAGGCAGAAC TTCGGCAGCA GCTTTCCTTC TCTCCTGCCA CGAAGAGATT
      L  Q  Q  L  K  A  E  L  R  Q  Q  L  S  F  S  P  A  T  K  R
241 GGAACAGCCC AGTACACCGG CCCATCTGAG TTCACTTTGC ATCTCAATTT TGTTCTTCAA
      L  E  Q  P  S  T  P  A  H  L  S  S  L  G  I  S  I  L  F  F
301 CATATTTGAT CCTCTGCCAG CTTTGAGTCA TCTTCAGACG TGGAGCTGTG AAAATCAGCT
      N  I  F  D  P  L  P  A  L  S  H  L  Q  T  W  S  C  E  N  Q
361 GCAACTGAAA ATGTCTGACA GCTTGGATAA CGAAGAAAAA CCTCCAGCTC CCACTGAGGA
      L  Q  L  K  M  S  D  S  L  D  N  E  E  K  P  P  A  P  T  E
421 TGACAGTAAC ACCGAGATTC TTCAGCACTC AACCACAGCT CCAAACCACT GCCCATGCGC
      D  D  S  N  T  E  I  L  Q  H  S  T  T  A  P  N  H  C  P  C
481 CCCGAAGAGA AGAATAAGAA AGCCAGGCTT CGCTCTATCT TCCCAGGAGG AGGGGATAAA
      A  R  K  R  R  I  R  K  P  G  F  A  L  S  S  Q  E  E  G  I
541 ACCAATAAGA AGAAAGAGAA AGAACGCCCA GAGATCTCTC TTCCTTCAGA CTTTGAGCAT
      K  P  I  R  R  K  R  K  N  A  Q  R  S  L  F  L  Q  T  L  S
601 ACGATTCATG TGGGTTTTGA TGCAGTCACC GGGGAATTCA CTCCAGATCT CTATGGCTCA
      I  R  F  M  W  V  L  M  Q  S  P  G  N  S  L  Q  I  S  M  A
661 CAGATGTGCC CAGGAAGCTC CAGAGGGAAT TCCTGAACAA TGGGCTCGAC TGCTCCAAAC
      H  R  C  A  Q  E  A  P  E  G  I  P  E  Q  W  A  R  L  L  Q
```

FIG. 10

FIG. 11A

```
           K   E   A   T   P   P   S   A   E   N   A   N   S   S   T   L   Y   R   N   T
  712  gatcggcaaagaaaaatccaagatgacagatgaggagatcctagagaagctaagaagc
         D   R   Q   R   K   K   S   K   M   T   D   E   E   I   L   E   K   L   R   S
  772  attgtgagtgttggggadccaagaagaaatatacaagatttgaaaaattggccaaggg
         I   V   S   V   G   X   P   K   K   K   Y   T   R   F   E   K   I   G   Q   G
  832  gcatcaggaactgtttacacagcactagacattgcgacaggacaagaggtggctataaag
         A   S   G   T   V   Y   T   A   L   D   I   A   T   G   Q   E   V   A   I   K
  892  caaatgaaccttcaacagcagcccaaaaaggaattaattaatgaaattcttgtcatg
         Q   M   N   L   Q   Q   P   K   K   E   L   I   I   N   E   I   L   V   M
  952  agggaaaataagaaccccaatattgtcaattatttagatagctacttagtgggtgatgaa
         R   E   N   K   N   P   N   I   V   N   Y   L   D   S   Y   L   V   G   D   E
 1012  ctgtgggtagtcatggaatacttggctgtctctttgactgacgtggtcacagaaacc
         L   W   V   V   M   E   Y   L   A   G   S   L   T   D   V   V   T   E   T
 1072  tgtatggatgaaggacagatagcagccgtctgtagagagtgcctccaagctttggattc
         C   M   D   E   G   Q   I   A   A   V   C   R   E   C   L   Q   A   L   D   F
 1132  ttgcactcaaaccaagtgatccacagagatataaagatggacaatattctcctcgggatg
         L   H   S   N   Q   V   I   H   R   D   I   K   M   D   N   I   L   L   G   M
 1192  gatggttctgttaaactggttgtgggaactcccctattctgtgccccaaatcactcctgagcaaagt
         D   G   S   V   K   L   T   D   F   G   F   C   A   Q   I   T   P   E   Q   S
 1252  aaacgaagcactatggttggtatatctggtctctggaatcatggccattgaaatggtggaa
         K   R   S   T   M   V   G   T   P   Y   W   M   A   P   E   V   T   R   K
 1312  gcttatggcccgaaagttgatatctggtctctggaatcatggccattgaaatggtggaa
         A   Y   G   P   K   V   D   I   W   S   L   G   I   M   A   I   E   M   V   E
 1372  ggtgaaccccccttaccttgaaaatccactcaggcccttatatctgatagccactaat
         G   E   P   P   Y   L   N   E   N   P   L   R   A   L   Y   L   I   A   T   N
 1432  ggaaccccagagcccagaatccgagagactgtcagctgtattccgtgacttcttaaat
         G   T   P   E   L   Q   N   P   E   R   L   S   A   V   F   R   D   F   L   N
 1492  cgctgtcttgagatggatgtggatagacgaggcagtgccaaggtctgcaagagcttttgcagcatcca
         R   C   L   E   M   D   V   D   R   R   G   S   A   K   E   L   L   Q   H   P
```

FIG. 11B

```
1552  tttttaaaattagccaagcccctgtccagccctcactcctctgattcttgctgcaaaggaa
       F   L   K   L   A   K   P   L   S   S   L   T   P   L   I   A   K   E
1612  gccattaagaacagtagccgttagagtgcaagcctaccctcaccgtctcccggatga
       A   I   K   N   S   S   R   *
1672  gtaagactgaactaaaactctgctgcaggatccacagaagaaagacagtcaaatggagt
1732  ggggttcctttaacttcaagtgaatagaaacttcttatataaacctttttcctactccctc
1792  agattatgtaatttattgtaagcctgaaccgcagccacacaggcagcaatgtcgaag
1852  tagccattaagtggccaacttccaccgtgaagcgagagagcagttgaatccctcat
1912  tcgtgcatttacttgaagaaaagagattctcaaagtcacactcctcttcatagt
1972  gctgtgttttaagttagagagtattcccctcaaacctctctttcaaaatccct
2032  tacccaacgtgatgttttttcacttgtcattagatgtccagaaaaaa  2082
```

FIG. 11C

```
N-PAK   ......MS DSLDNEEKPP APPLRMNS.. .....NNRDSSA LNHSSKPLPM   37
PAK1    .....MSN NGLDVQDKPP APPMRNTSTM IGAGSKDPGT LNHGSKPLPP      43
STE20   QINSASHSLS NPKHKQHKPK VKPSKPEAKS KPVSVKKSFP ...SKNPLKN   267

N-PAK   APEEKNKKAR L....... .......... .RSIFPGGGD KTNKKKEKER     67
PAK1    NPEEKKKKDR FY...... .......... .RSIL..AGD KTNKKKEKER     72
STE20   SSPPKKQTEK SYYSSSSKKR KSGSNSGTLR MKDVFTSFVQ NIKRNSQDDK   317

N-PAK   PE........ .......... .......... SLPSDFEHTI HVGFDAVTGE FTGIPEQWAR  100
PAK1    HE........ .......... .......... SLPSDFEHTI HVGFDACTGE FTGMPEQWAR  105
STE20   RASSSSNNSS SSSITTALRI EQQQNMQAVM STPYNAKHH HVGMDSKTGE YTIGLPEEWEK  367

N-PAK   LLQTSNITKL EQKKNPQAVL DVLKFYD... .......... .......... ..........  127
PAK1    LLQTSNITKS EQKKNPQAVL DVLEFYN... .......... .......... ..........  132
STE20   LITSGIISKR EQQQNMQAVM DIVKFYQDVT ETNGEDKMFK TFNTTTGLPG              417

N-PAK   .......... SKETV NNQKYMSFTS GDKSAHGYIA ......AHQSN                 157
PAK1    .......... SKKTS NSQKYMSFT. DKSAEDYNS .......SNTLN                160
STE20   SPQVSTPPAN SFNKFPPSTS DSHNYGSRTG TPMSNHVMSP TLNTDSSSAN            467

N-PAK   TKTASEPPLA PPVSEEEDEE EEEE...... .......... ..........            181
PAK1    VKTYSETPAV PPVSEDED.. D......... .......... ..........            179
STE20   GKFIPSRPAP KPPSSASASA PIIKSPVMNS AANVSPLKQT HAPTTPNRTS            517

N-PAK   .......... EDDNEPPP VIAPRPEHTK SI....YTRS VVESIASPAA               215
PAK1    .......... DDDATPPP VIAPRPEHTK SV....YTRS VIEPLPVTPT               213
STE20   PNRSSISRNA TLKKEEQPLP PIPPTKSKTS PIISTAHTPQ QVAQSPKAPA            567
```

FIG. 12A

| | | | | |
|---|---|---|---|---|
| N-PAK | PNKEATPPSA | ENANSS....T | LYRNTDRQRK | KSKMTDEEIL | EKLRSIVSVG | 262 |
| PAK1 | RDVATSPISP | TENNTTPPDA | LTRNTEKQKK | KPKMSDEEIL | EKLRNIVSVG | 263 |
| STE20 | QETVTTPTSK | PAQARSLSKE | L....NEKKRE | ERERRKKQLY | AKLNEICSDG | 614 |
| | | | | |
| N-PAK | DPKKYTRFE | KIGQGASGTV | YTALDIATGQ | EVAIKQMNLQ | QQPKKELIIN | 312 |
| PAK1 | DPKKYTRFE | DIGQGASSTV | YTAMDVATGQ | EVAILQMNLQ | QQPKKELIIN | 313 |
| STE20 | DPSTKYANLV | KIGQGASGGV | YTAYEIGTNV | SVAIKQMNLE | KQPKKELIIN | 664 |
| | | | | |
| N-PAK | EILVMRENKN | PNIVNYLDSY | SVGDELWVVM | EYLAGESLTD | VVTETCMDEG | 362 |
| PAK1 | EILVMRENKN | PNIVNYLDSY | LVGDELWVVM | EYLAGGSLTD | VVTETCMDEG | 363 |
| STE20 | EILVMKGSKH | PNIVNFIDSY | VLKGDLWVIM | EYMEGGSLTD | VVTHCILTEG | 714 |
| | | | | |
| N-PAK | QIAAVERECL | QALDFLHSNQ | VIHRDIKSDN | ILLGMDGSVK | LTDFGFCAQI | 412 |
| PAK1 | QIAAVCRECL | QALEFLHSNQ | VIHRDIDSDN | ILLGMDGSVK | LTDFGFCAQI | 413 |
| STE20 | QIGAVCRETL | SGLEFLHSKG | VLHRDIKSDN | ILLSMEGDIK | LTKFGFCAQI | 764 |
| | | | | |
| N-PAK | TPEQSKRSTM | VGTPYWMAPE | VVTRKAYGPK | VDIWSLGIMA | IEMVEGEPPY | 462 |
| PAK1 | TPEQSKRSTM | VGTPYWMAPE | VVTRKAYGPK | VDIWSLGIMA | IEMIEGEPPY | 463 |
| STE20 | NELNLKRTTM | VGTPYWMAPE | VVSRKEYGPK | VDIWSLGIMI | IEMIEGEPPY | 814 |
| | | | | |
| N-PAK | LNENPLRALY | LIATNGTPEL | QNPERLSAVF | RDFLNRCLEM | DVDRRGSAKE | 512 |
| PAK1 | LNENPLRALY | LIATNGTPEL | QNPEKLSAIF | RDFLNRCLEM | DVEKRGSAKE | 513 |
| STE20 | LNETPLRALY | LIATNGTPKL | KEPENLSSSL | KKFLDWCLCV | EPEDRASATE | 864 |
| | | | | |
| N-PAK | LLQHPFL.KL | AKPLSSLTPL | ILAAK...... | ...EAIKNSS | R.......... | 544 |
| PAK1 | LLQHQFL.KI | AKPLSSLTPL | IAAAK...... | ...EATKNNH | .......... | 544 |
| STE20 | LLHDEYITEI | AEANSSLAPL | VKLARLKKVA | ENMDADEDND | DDNDNEHINK | 914 |

FIG. 12B

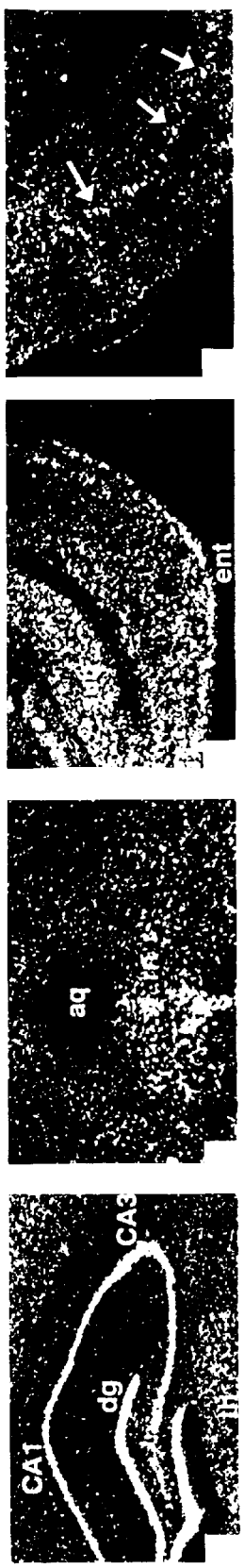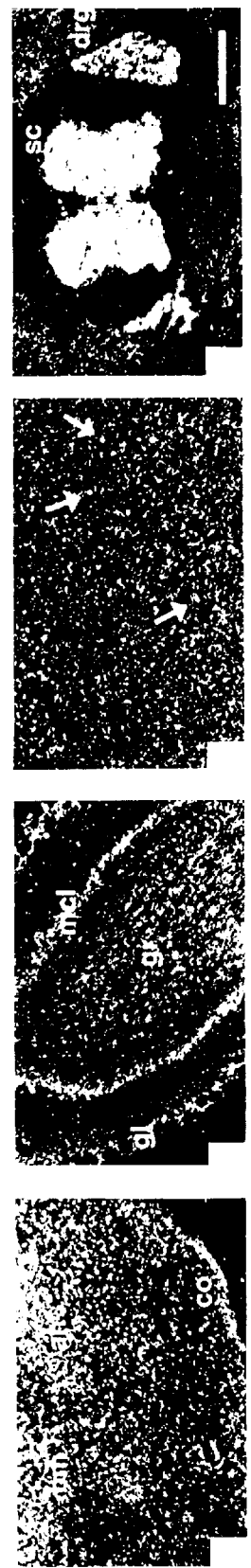
FIG.17A FIG.17B FIG.17C FIG.17D
FIG.17E FIG.17F FIG.17G FIG.17H

HABIR #1 #4

1   GGAATTCTGC CAGTTTATTA CAGAGGACGA TAAATGATTC CATGTGGATA GGGCATAACA
    CCTTAAGACG GTCAAATAAT GTCTCCTGCT ATTTACTAAG GTACACCTAT CCCGTATTGT

61  TACAGAGAAT GAGACTATGC CAGA
    ATGTCTCTTA CTCTGATACG GTCT

1 #1 T3

1   GGAATTCCCA GTGGAAACCA AATGAAACGA CTTTGNCTTG TNGAGGGGGA AGAATGTGAA
    CCTTAAGGGT CACCTTTGGT TTACTTTGCT GAAACNGAAC ANCTCCCCCT TCTTACACTT

61  MAAAAAACAA AAGCAAAATG ACCCGCCCAC AAGATACAAC AGAAACCCCA TCCACTACCC
    KTTTTTTGTT TTCGTTTTAC TGGGCGGGTG TTCTATGTTG TCTTTGGGGT AGGTGATGGG

121 ATCCCTTCCA TGTGAGGCCG ACCACCCAGG CCCCAACACC CT
    TAGGGAAGGT ACACTCCGGC TGGTGGGTCC GGGGTTGTGG GA

4.t3

1   GGAATTCCAA TAAGAAGAAG GAGAAAGAGC GCCCAGAGAT CTCTCTTCCT TCAGACTTTG
    CCTTAAGGTT ATTCTTCTTC CTCTTTCTCG CGGGTCTCTA GAGAGAAGGA AGTCTGAAAC

61  AGCATACGAT TCATGTGGGG TTGATGCAGT CACCGGGAAT TCACTCCAGA
    TCGTATGCTA AGTACACCCC AACTACGTCA GTGGCCCTTA AGTGAGGTCT

FIG.18

```
  1 aataagaagaaggagaaagagcgcccagagatctctcttccttcagactt  50
    ||||||||||  |||||||| |||||||||||||||||||||||||||||
544 aataagaagaaagagaaagaacgcccagagatctctcttccttcagactt 593

51 tgagcatacgattcatgtggg.gttgatgcagtcacc.gggaattcactc  98
    ||||||||||||||||||||| |||||||||||||||| |||||||||||
594 tgagcatacgattcatgtgggttttgatgcagtcaccggggaattcactc 643

99 caga 102
    ||||
644 caga 647
```

FIG.19A

```
 11 ttacagaggacgataaatgattccatgtggatagggcataacat  54
    |||||  |  ||||||| |    |||||    |||   |||   ||||
182 ttacatcaggagataaaagtgcccatggatatatagcagcacat 225
```

FIG.19B

```
  53 naaaaaacaaaagcaaaa   70
     :||||||  |||||||||
1868 aaaaaaaagaaagcaaaa 1885
```

FIG.19C

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
      (A) LENGTH: 1971 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: Coding Sequence
      (B) LOCATION: 1...1395
      (D) OTHER INFORMATION:

(xi) SEQUENCE DESCRIPTION: SEQ ID NO:1:

```
CCC CCT CGA GGT CGA CTC CTG GAG CCC GTC AGT ATC GGC GGA ATT CCT      48
Pro Pro Arg Gly Arg Leu Leu Glu Pro Val Ser Ile Gly Gly Ile Pro
 1               5                  10                  15

GAA CAA TGG GCT CGA CTG CTC CAA ACC TCC AAC ATT ACA AAA CTG GAA      96
Glu Gln Trp Ala Arg Leu Leu Gln Thr Ser Asn Ile Thr Lys Leu Glu
                20                  25                  30

CAG AAG AAG AAC CCA CAG GCT GTT CTG GAT GTT CTC GAG TTT TAC GAC     144
Gln Lys Lys Asn Pro Gln Ala Val Leu Asp Val Leu Glu Phe Tyr Asp
             35                  40                  45

TCC AAA GAA ACA GTC AAC AAC CAG AAA TAC ATG AGC TTT ACA TCA GGA     192
Ser Lys Glu Thr Val Asn Asn Gln Lys Tyr Met Ser Phe Thr Ser Gly
 50                  55                  60

GAT AAA AGT GCC CAT GGA TAT ATA GCA GCA CAT CAG TCG AAT ACC AAA     240
Asp Lys Ser Ala His Gly Tyr Ile Ala Ala His Gln Ser Asn Thr Lys
 65                  70                  75                  80

ACA GCT TCA GAA CCT CCT TTG GCT CCT CCT GTA TCT GAA GAA GAG GAT     288
Thr Ala Ser Glu Pro Pro Leu Ala Pro Pro Val Ser Glu Glu Glu Asp
                 85                  90                  95

GAA GAA GAG GAA GAG GAA GAA GAT GAT AAT GAG CCC CCG CCT GTC ATT     336
Glu Glu Glu Glu Glu Glu Glu Asp Asp Asn Glu Pro Pro Pro Val Ile
                100                 105                 110

GCA CCA AGA CCA GAG CAT ACA AAA TCA ATC TAT ACT CGT TCT GTG GTT     384
Ala Pro Arg Pro Glu His Thr Lys Ser Ile Tyr Thr Arg Ser Val Val
            115                 120                 125

GAG TCA ATT GCT TCA CCA GCA GCA CCA AAT AAA GAA GCC ACC CCA CCT     432
Glu Ser Ile Ala Ser Pro Ala Ala Pro Asn Lys Glu Ala Thr Pro Pro
        130                 135                 140

TCT GCT GAG AAT GCC AAT TCC AGT ACT TTG TAC AGG AAT ACA GAT CGG     480
Ser Ala Glu Asn Ala Asn Ser Ser Thr Leu Tyr Arg Asn Thr Asp Arg
145                 150                 155                 160

CAA AGA AAA AAA TCC AAG ATG ACA GAT GAG GAG ATC CTA GAG AAG CTA     528
Gln Arg Lys Lys Ser Lys Met Thr Asp Glu Glu Ile Leu Glu Lys Leu
                165                 170                 175

AGA AGC ATT GTG AGT GTT GGG GAC CCA AAG AAG AAA TAT ACA AGA TTT     576
Arg Ser Ile Val Ser Val Gly Asp Pro Lys Lys Lys Tyr Thr Arg Phe
            180                 185                 190

GAA AAA ATT GGC CAA GGG GCA TCA GGA ACT GTT TAC ACA GCA CTA GAC     624
Glu Lys Ile Gly Gln Gly Ala Ser Gly Thr Val Tyr Thr Ala Leu Asp
        195                 200                 205

ATT GCG ACA GGA CAA GAG GTG GCT ATA AAG CAA ATG AAC CTT CAA CAG     672
Ile Ala Thr Gly Gln Glu Val Ala Ile Lys Gln Met Asn Leu Gln Gln
```

-continued

```
        210                 215                 220
CAG CCC AAA AAG GAA TTA ATT ATT AAT GAA ATT CTT GTC ATG AGG GAA    720
Gln Pro Lys Lys Glu Leu Ile Ile Asn Glu Ile Leu Val Met Arg Glu
225                 230                 235                 240

AAT AAG AAC CCC AAT ATT GTC AAT TAT TTA GAT AGC TAC TTA GTG GGT    768
Asn Lys Asn Pro Asn Ile Val Asn Tyr Leu Asp Ser Tyr Leu Val Gly
                245                 250                 255

GAT GAA CTG TGG GTA GTC ATG GAA TAC TTG GCT GGT GGC TCT TTG ACT    816
Asp Glu Leu Trp Val Val Met Glu Tyr Leu Ala Gly Gly Ser Leu Thr
            260                 265                 270

GAC GTG GTC ACA GAA ACC TGT ATG GAT GAA GGA CAG ATA GCA GCC GTC    864
Asp Val Val Thr Glu Thr Cys Met Asp Glu Gly Gln Ile Ala Ala Val
        275                 280                 285

TGT AGA GAG TGC CTC CAA GCT TTG GAT TTC TTG CAC TCA AAA CAA GTG    912
Cys Arg Glu Cys Leu Gln Ala Leu Asp Phe Leu His Ser Lys Gln Val
    290                 295                 300

ATC CAC AGA GAT ATA AAG AGT GAC AAT ATT CTC CTC GGG ATG GAT GGT    960
Ile His Arg Asp Ile Lys Ser Asp Asn Ile Leu Leu Gly Met Asp Gly
305                 310                 315                 320

TCT GTT AAA CTG ACT GAT TTT GGA TTC TGT GCC CAA ATC ACT CCT GAG    1008
Ser Val Lys Leu Thr Asp Phe Gly Phe Cys Ala Gln Ile Thr Pro Glu
                325                 330                 335

CAA AGT AAA CGA AGC ACT ATG GTG GGA ACT CCC TAT TGG ATG GCA CCT    1056
Gln Ser Lys Arg Ser Thr Met Val Gly Thr Pro Tyr Trp Met Ala Pro
            340                 345                 350

GAG GTG GTA ACT CGA AAA GCT TAT GGC CCG AAA GTT GAT ATC TGG TCT    1104
Glu Val Val Thr Arg Lys Ala Tyr Gly Pro Lys Val Asp Ile Trp Ser
        355                 360                 365

CTG GGA ATC ATG GCC ATT GAA ATG GGT GAA CCT GAA CCC CCT TAC CTT    1152
Leu Gly Ile Met Ala Ile Glu Met Gly Glu Pro Glu Pro Pro Tyr Leu
    370                 375                 380

AAT GAA AAT CCA CTC AGG GCC TTA TAT CTG ATA GCC ACT AAT GGA ACC    1200
Asn Glu Asn Pro Leu Arg Ala Leu Tyr Leu Ile Ala Thr Asn Gly Thr
385                 390                 395                 400

CCA GAG CTC CAG AAT CCC GAG AGA CTC TCA GCT GTA TTC CGT GAC TTC    1248
Pro Glu Leu Gln Asn Pro Glu Arg Leu Ser Ala Val Phe Arg Asp Phe
                405                 410                 415

TTA AAT CGC TGT CTT GAG ATG GAT GTG GAT AGA CGA GGG TCT GCC AAG    1296
Leu Asn Arg Cys Leu Glu Met Asp Val Asp Arg Arg Gly Ser Ala Lys
            420                 425                 430

GAG CTT TTC CAG CAT CCA TTT TTA AAA TTA GCC AAG CCC CTG TCC AGC    1344
Glu Leu Phe Gln His Pro Phe Leu Lys Leu Ala Lys Pro Leu Ser Ser
        435                 440                 445

CTC ACT CCT CTG ATT CTT GCT GCA AAG GAA GCC ATT AAG AAC AGT AGC    1392
Leu Thr Pro Leu Ile Leu Ala Ala Lys Glu Ala Ile Lys Asn Ser Ser
    450                 455                 460

CGT TAGAAGTGCA AGCCTTACCC CTCACCGTCT CCCGGATGAG TAAGACTGAA CTAAAA   1451
Arg
465

CTCTGCTGCA GGATCCACAG AAGAAAAGAC AGTCAAATGG AGTGGGGTT CTTTAACTTT    1511

CAAGTGAATA GAAACTTCTT ATAAACCTTT TTCCTACTCC CTCAGATTAT GTAATTTATT    1571

TGTAAGCCTG AACCGCAGCC CACACAGGGC AGCAATGTCG AAGTAGCCAT TAAGTGGCCA    1631

CTTCCACCGT GAAGCGAGAG AGCCAGTAGT GAATCCCCTC ATTCGTGCAT TTACTTTGAA    1691

GAAAAAGAGA TTTCTCAAAG ATGCACACTC CCTCTTCATA GTGCTGTGTG TTTTTAAGTT    1751

AGAGAGTAGT CCCCCTTCCA TTCAAACCTC TTTCAAAATC CCTTACCCAA CGTGATGTTT    1811

TTTCACTTGC ATTGTCATTA GATGTCCAGA AAAAAGATG TCAAAATGTT TTTTTTAAAA    1871
```

```
AAAAGAAAGC AAAAAAGCAA AGAAAAAAGG AATTCCAGCT GAGCGCCGGT CGCTACCATT    1931

ACCAGTTGGT CTGGTGTCAA GCGGCCGCCA CCGCGGTGGA                          1971
```

(2) INFORMATION FOR SEQ ID NO:2:

(i) SEQUENCE CHARACTERISTICS:
        (A) LENGTH: 465 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:2:

```
Pro Pro Arg Gly Arg Leu Leu Glu Pro Val Ser Ile Gly Gly Ile Pro
  1               5                  10                  15

Glu Gln Trp Ala Arg Leu Leu Gln Thr Ser Asn Ile Thr Lys Leu Glu
             20                  25                  30

Gln Lys Lys Asn Pro Gln Ala Val Leu Asp Val Leu Glu Phe Tyr Asp
         35                  40                  45

Ser Lys Glu Thr Val Asn Asn Gln Lys Tyr Met Ser Phe Thr Ser Gly
 50                  55                  60

Asp Lys Ser Ala His Gly Tyr Ile Ala Ala His Gln Ser Asn Thr Lys
 65                  70                  75                  80

Thr Ala Ser Glu Pro Pro Leu Ala Pro Pro Val Ser Glu Glu Glu Asp
             85                  90                  95

Glu Glu Glu Glu Glu Glu Glu Asp Asp Asn Glu Pro Pro Pro Val Ile
            100                 105                 110

Ala Pro Arg Pro Glu His Thr Lys Ser Ile Tyr Thr Arg Ser Val Val
            115                 120                 125

Glu Ser Ile Ala Ser Pro Ala Ala Pro Asn Lys Glu Ala Thr Pro Pro
130                 135                 140

Ser Ala Glu Asn Ala Asn Ser Ser Thr Leu Tyr Arg Asn Thr Asp Arg
145                 150                 155                 160

Gln Arg Lys Lys Ser Lys Met Thr Asp Glu Glu Ile Leu Glu Lys Leu
                165                 170                 175

Arg Ser Ile Val Ser Val Gly Asp Pro Lys Lys Lys Tyr Thr Arg Phe
            180                 185                 190

Glu Lys Ile Gly Gln Gly Ala Ser Gly Thr Val Tyr Thr Ala Leu Asp
        195                 200                 205

Ile Ala Thr Gly Gln Glu Val Ala Ile Lys Gln Met Asn Leu Gln Gln
210                 215                 220

Gln Pro Lys Lys Glu Leu Ile Ile Asn Glu Ile Leu Val Met Arg Glu
225                 230                 235                 240

Asn Lys Asn Pro Asn Ile Val Asn Tyr Leu Asp Ser Tyr Leu Val Gly
                245                 250                 255

Asp Glu Leu Trp Val Val Met Glu Tyr Leu Ala Gly Gly Ser Leu Thr
            260                 265                 270

Asp Val Val Thr Glu Thr Cys Met Asp Glu Gly Gln Ile Ala Ala Val
        275                 280                 285

Cys Arg Glu Cys Leu Gln Ala Leu Asp Phe Leu His Ser Lys Gln Val
290                 295                 300

Ile His Arg Asp Ile Lys Ser Asp Asn Ile Leu Leu Gly Met Asp Gly
305                 310                 315                 320

Ser Val Lys Leu Thr Asp Phe Gly Phe Cys Ala Gln Ile Thr Pro Glu
```

```
            325                 330                 335
Gln Ser Lys Arg Ser Thr Met Val Gly Thr Pro Tyr Trp Met Ala Pro
            340                 345                 350
Glu Val Val Thr Arg Lys Ala Tyr Gly Pro Lys Val Asp Ile Trp Ser
            355                 360                 365
Leu Gly Ile Met Ala Ile Glu Met Gly Glu Pro Glu Pro Pro Tyr Leu
            370                 375             380
Asn Glu Asn Pro Leu Arg Ala Leu Tyr Leu Ile Ala Thr Asn Gly Thr
385                 390                 395                 400
Pro Glu Leu Gln Asn Pro Glu Arg Leu Ser Ala Val Phe Arg Asp Phe
                405                 410                 415
Leu Asn Arg Cys Leu Glu Met Asp Val Asp Arg Arg Gly Ser Ala Lys
                420                 425                 430
Glu Leu Phe Gln His Pro Phe Leu Lys Leu Ala Lys Pro Leu Ser Ser
            435                 440                 445
Leu Thr Pro Leu Ile Leu Ala Ala Lys Glu Ala Ile Lys Asn Ser Ser
            450                 455                 460
Arg
465

(2) INFORMATION FOR SEQ ID NO:3:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

CAGGAATACA GATCGGCAAA GAAAAAAATC CAAGATGACA GATGAGGAGA TCCTAGAGAA      60

GCTAAGAACA TTGTGNGTGT TGGGGACCCA AGAAGANNN TATACAAGAT TGAAAAAAT      120

(2) INFORMATION FOR SEQ ID NO:4:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

GATCATCATC ACCTTCCAGG AGCAGGGAGA CAAGATGATG GAAGAATACA GCCTAGAGAA      60

AAATGAGAGG GCCTGCATCG ACTTTGCCAT CAGTGCCAAG CCGCTGACCA GGCACATGCC     120

(2) INFORMATION FOR SEQ ID NO:5:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

TTCAGAACCT CCTTTGGCTC CTCCTGTATC TGAAGAAGAG GATGAAGAAG AGGAAGAGGA      60

AGAAGATGAT AATGAGCCCC GCCTGTCATT GCACCAAGAC CAGAGCATAC AAAATAATCT     120
```

(2) INFORMATION FOR SEQ ID NO:6:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

```
TGAGGATAAA GAGGATGATG ATGACAGAGA TGAAGATGAG GACGAAGAAG ATGAGAAGGA      60
GGAAGATGAG GAAGAATCCC CTGGCCAAGC CAAGGATGAG CTGTAGAGGC CACACCACCT     120
```

(2) INFORMATION FOR SEQ ID NO:7:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
TTCAGAACCT CCTTTGGCTC CTCCTGTATC TGAAGAAGAG GATGAAGAAG AGGAAGAGGA      60
AGAAGATGAT AATGAGCCCC GCCTGTCATT GCACCAAGAC CAGAGCATAC AAAATAATCT     120
```

(2) INFORMATION FOR SEQ ID NO:8:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
CGAGGATAAA GAGGATGAGG ATGACAGAGA TGAAGATGAA GATGAAGAGG ATGAGAAGGA      60
AGAAGATGAG GAGGATGCCA CTGGCCAAGC CAAGGATGAG CTGTAGAGGC CACACCACCT     120
```

(2) INFORMATION FOR SEQ ID NO:9:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
TCAGAACCTC CTTTGGCTCC TCCTGTATCT GAAGAAGAGG ATGAAGAAGA GGAAGAGGAA      60
GAAGATGATA ATGAGCCCCG CCTGTCATTG CACCAAGNNA CCAGAGCATA CAAAATAATC     120
TATACTCGTC TGTGGTTGAG TCAATTGCTN TCACCAGCAG CACCAAATAA AGAAGCCACC     180
CACCTTCTGC TGAGATGCCA ATTCCAGTAC TTTGACAGGA ATACAGATCG GCAAAGAAAA     240
```

(2) INFORMATION FOR SEQ ID NO:10:

(i) SEQUENCE CHARACTERISTICS:
        (A) LENGTH: 240 base pairs
        (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO:10:

ACAGCACAGG AAAAGGAAGA TGAGGAAAAA GAGGAAGAGG AGGCAGCAGA AGGGGAGAAA      60

GAAGAAGGCT TGGAGGAAGG GCTGNCTCCA GATGAAGTTG CCAGAGTCTG TGAAGTTACA     120

GATGTGCCAC NCTGCTGGAG TNNATTTCTG TGACCAAGAG CTGCAGCACC GTGTGGAGTC     180

CCTGGCAGCC TTTGCGGAGC GCTATGTGGA CAAGCTCCAG GCCAACCAGC GGAGCCGCTA     240

(2) INFORMATION FOR SEQ ID NO:11:

(i) SEQUENCE CHARACTERISTICS:
        (A) LENGTH: 209 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:11:

Pro Pro Arg Gly Arg Leu Leu Glu Pro Val Ser Ile Gly Gly Ile Pro
  1               5                  10                  15

Glu Gln Trp Ala Arg Leu Leu Gln Thr Ser Asn Ile Thr Lys Leu Glu
             20                  25                  30

Gln Lys Lys Asn Pro Gln Ala Val Leu Asp Val Leu Glu Phe Tyr Asp
         35                  40                  45

Ser Lys Glu Thr Val Asn Asn Ile Gln Lys Tyr Met Ser Phe Thr Ser
     50                  55                  60

Gly Asp Lys Ser Ala His Gly Tyr Ile Ala Ala His Gln Ser Glu Tyr
 65                  70                  75                  80

Gln Thr Ala Ser Glu Pro Pro Leu Ala Pro Val Ser Glu Glu Glu
                 85                  90                  95

Asp Glu Glu Glu Glu Glu Glu Asp Asp Asn Glu Pro Arg Leu Ser
                100                 105                 110

Leu His Gln Asp Gln Ser Ile Gln Asn Asn Leu Tyr Ser Ser Val Val
        115                 120                 125

Glu Ser Ile Ala Ser Pro Ala Ala Pro Asn Lys Glu Ala Thr His Leu
130                 135                 140

Leu Leu Arg Cys Gln Phe Gln Tyr Phe Asp Arg Asn Thr Asp Arg Gln
145                 150                 155                 160

Arg Lys Lys Ser Lys Met Thr Asp Glu Glu Ile Leu Glu Lys Leu Arg
                165                 170                 175

Thr Leu Pro Val Leu Gly Thr Gln Arg Arg Phe Tyr Thr Arg Phe Glu
                180                 185                 190

Lys Ile Gly Gln Gly Ala Ser Gly Thr Val Tyr Thr Ala Leu Asp Ile
            195                 200                 205

Ala (2) INFORMATION FOR SEQ ID NO:12:

(i) SEQUENCE CHARACTERISTICS:
        (A) LENGTH: 240 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:12:

```
Gly Val Gly Val Thr Thr Ser Leu Arg Pro Pro His His Phe Ser Pro
 1               5                  10                  15

Pro Cys Phe Val Ala Ala Leu Pro Ala Ala Gly Ala Ala Glu Ala Pro
            20                  25                  30

Ala Arg Leu Ser Pro Ala Ile Pro Leu Glu Ala Leu Arg Asp Lys Ala
        35                  40                  45

Leu Arg Met Leu Gly Glu Ala Val Arg Asp Gly Gln His Ala Arg
    50                  55                  60

Asp Pro Val Gly Ala Ser Val Glu Phe Gln Phe Val Pro Val Leu Lys
65                  70                  75                  80

Leu Val Ser Thr Leu Leu Val Met Gly Ile Phe Gly Asp Glu Asp Val
                85                  90                  95

Lys Gln Ile Leu Lys Met Ile Glu Pro Glu Val Phe Thr Glu Glu Glu
                100                 105                 110

Glu Glu Glu Asp Glu Glu Glu Gly Glu Glu Glu Asp Glu Glu Glu
            115                 120                 125

Lys Glu Glu Asp Glu Glu Glu Thr Ala Gln Glu Lys Glu Asp Glu Glu
    130                 135                 140

Lys Glu Glu Glu Glu Ala Ala Glu Gly Glu Lys Glu Glu Gly Leu Glu
145                 150                 155                 160

Glu Gly Leu Leu Gln Met Lys Leu Pro Glu Ser Val Lys Leu Gln Met
                165                 170                 175

Cys His Leu Leu Glu Tyr Phe Cys Asp Gln Glu Leu Gln His Arg Val
                180                 185                 190

Glu Ser Leu Ala Ala Phe Ala Glu Arg Tyr Val Asp Lys Leu Gln Ala
            195                 200                 205

Asn Gln Arg Ser Arg Tyr Gly Leu Leu Ile Lys Ala Phe Ser Met Thr
    210                 215                 220

Ala Ala Glu Thr Ala Arg Arg Thr Arg Glu Phe Arg Ser Pro Pro Gln
225                 230                 235                 240
```

(2) INFORMATION FOR SEQ ID NO:13:

(i) SEQUENCE CHARACTERISTICS:
        (A) LENGTH: 207 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:13:

```
Pro Pro Arg Gly Arg Leu Leu Glu Pro Val Ser Ile Gly Gly Ile Pro
 1               5                  10                  15

Glu Gln Trp Ala Arg Leu Leu Gln Thr Ser Asn Ile Thr Lys Leu Glu
            20                  25                  30

Gln Lys Lys Asn Pro Gln Ala Val Leu Asp Val Leu Glu Phe Tyr Asp
        35                  40                  45

Ser Lys Glu Thr Val Asn Asn Gln Lys Tyr Met Ser Phe Thr Ser Gly
    50                  55                  60

Asp Lys Ser Ala His Gly Tyr Ile Ala Ala His Gln Ser Glu Tyr Gln
65                  70                  75                  80

Thr Ala Ser Glu Pro Pro Leu Ala Pro Val Ser Glu Glu Glu Asp
                85                  90                  95
```

```
Glu Glu Glu Glu Glu Glu Asp Asp Asn Glu Pro Arg Leu Ser Leu
            100                 105                 110

His Gln Asp Gln Ser Ile Gln Asn Asn Leu Tyr Ser Ser Val Val Glu
            115                 120                 125

Ser Ile Ala Ser Pro Ala Ala Pro Asn Lys Glu Ala Thr His Leu Leu
            130                 135                 140

Leu Arg Cys Gln Phe Gln Tyr Phe Asp Arg Asn Thr Asp Arg Gln Arg
145                 150                 155                 160

Lys Lys Ser Lys Met Thr Asp Glu Glu Ile Leu Glu Lys Leu Arg Thr
                165                 170                 175

Leu Pro Val Leu Gly Thr Gln Arg Arg Phe Tyr Thr Arg Phe Lys Ile
                180                 185                 190

Gly Gln Gly Ala Ser Gly Thr Val Tyr Thr Ala Leu Asp Ile Ala
                195                 200                 205
```

(2) INFORMATION FOR SEQ ID NO:14:

(i) SEQUENCE CHARACTERISTICS:
        (A) LENGTH: 240 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:14:

```
Gly Val Gly Val Thr Thr Ser Leu Arg Pro Pro His His Phe Ser Pro
1               5                   10                  15

Pro Cys Phe Val Ala Ala Leu Pro Ala Ala Gly Val Ala Glu Ala Pro
                20                  25                  30

Ala Arg Leu Ser Pro Ala Ile Pro Leu Glu Ala Leu Arg Asp Lys Ala
            35                  40                  45

Leu Arg Met Leu Gly Glu Ala Val Arg Asp Gly Gln His Ala Arg
50                  55                  60

Asp Pro Val Gly Gly Ser Val Glu Phe Gln Phe Val Pro Val Leu Lys
65                  70                  75                  80

Leu Val Ser Thr Leu Leu Val Met Gly Ile Phe Gly Asp Glu Asp Val
                85                  90                  95

Lys Gln Ile Leu Lys Met Ile Glu Pro Glu Val Phe Thr Glu Glu Glu
            100                 105                 110

Glu Glu Glu Glu Glu Glu Glu Glu Glu Glu Glu Glu Glu Glu Glu Asp
            115                 120                 125

Glu Glu Glu Lys Glu Glu Asp Glu Glu Glu Glu Lys Glu Asp Ala
            130                 135                 140

Glu Lys Glu Glu Glu Glu Ala Pro Glu Gly Glu Lys Glu Asp Leu Glu
145                 150                 155                 160

Glu Gly Leu Leu Gln Met Lys Leu Pro Glu Ser Val Lys Leu Gln Met
                165                 170                 175

Cys Asn Leu Leu Glu Tyr Phe Cys Asp Gln Glu Leu Gln His Arg Val
                180                 185                 190

Glu Ser Leu Ala Ala Phe Ala Glu Arg Tyr Val Asp Lys Leu Gln Ala
            195                 200                 205

Asn Gln Arg Ser Arg Tyr Ala Leu Leu Met Arg Ala Phe Thr Met Ser
            210                 215                 220

Ala Ala Glu Thr Ala Arg Arg Thr Arg Glu Phe Arg Ser Pro Pro Gln
225                 230                 235                 240
```

(2) INFORMATION FOR SEQ ID NO:15:

(i) SEQUENCE CHARACTERISTICS:
        (A) LENGTH: 675 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

```
CTGGTAATGG TAGCGACCGG CGCTCACGTG GAATTCGAGA CTGCTAGATT CGTCCCTGCC     60

AGCGTGCTCC GAGGTACTGG AAAGGTCTTG GCAGGGTGGC TGGACCCTTG GCAGGAGCTG    120

TGAAATCAGC TGCAACTGAA AATGTCTGAC AGCTTGGATA ACGAAGAAAA ACCTCCAGCT    180

CCCCCACTGA GGATGAACAG TAACAACCGA GATTCTTCAG CACTCAACCA CAGCTCCAAA    240

CCACTGCCCA TGCGCCCGGA AGAGAAGAAT AAGAAAGCCA GGCTTCGCTC TATCTTCCCA    300

GGAGGAGGGG ATAAAACCAA TAAGAAGAAA GAGAAAGAAC GCCCAGAGAT CTCTCTTCCT    360

TCAGACTTTG AGCATACGAT TCATGTGGGT TTTGATGCAG TCACCGGGGA ATTCACTCCA    420

GATCTCTATG GCTCACAGAT GTGCCCAGGA AGCTCCAGAG GGAATTCCTG AACAATGGGT    480

TCGACTGCTC CAAACCTCCA ACATTACAAA ACTGGAACAG AAGAAGAACC CACAGGCTGT    540

TCTGGATGTT CTCAAGTTTT ACGACTCCAA AGAAACAGTC AACAACCAGA AATACATGAG    600

CTTTACATCA GGAGATAAAA GTGCCCATGG ATATATAGCA GCACATCAGT CGAATACCAA    660

AACAGCTTCA GAACC                                                    675
```

(2) INFORMATION FOR SEQ ID NO:16:

(i) SEQUENCE CHARACTERISTICS:
        (A) LENGTH: 720 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 2...720
        (D) OTHER INFORMATION:

(xi) SEQUENCE DESCRIPTION: SEQ ID NO:16:

```
G AAT TCA CAC ATG ATC TTC TGG GCT CCT CCA AAG GGC TGG CAT TAC TTT     49
  Asn Ser His Met Ile Phe Trp Ala Pro Pro Lys Gly Trp His Tyr Phe
  1               5                  10                  15

TCT AGC TCT ACC CTC TGT AGC ACT CTA AGC TCA GGT CGT CCT CCT CCT       97
Ser Ser Ser Thr Leu Cys Ser Thr Leu Ser Ser Gly Arg Pro Pro Pro
            20                  25                  30

ACC ACT GCT GCT GCT GTG ATC GCC TAT CCC CTC TCA TCC TCC TTC CTC      145
Thr Thr Ala Ala Ala Val Ile Ala Tyr Pro Leu Ser Ser Ser Phe Leu
        35                  40                  45

GCC AAT TTC TGC TCC TCC TCC CGC ATC CCG CTC CTC CAG CAG CTA AAG      193
Ala Asn Phe Cys Ser Ser Ser Arg Ile Pro Leu Leu Gln Gln Leu Lys
50                  55                  60

GCA GAA CTT CGG CAG CAG CTT TCC TTC TCT CCT GCC ACG AAG AGA TTG      241
Ala Glu Leu Arg Gln Gln Leu Ser Phe Ser Pro Ala Thr Lys Arg Leu
65                  70                  75                  80

GAA CAG CCC AGT ACA CCG GCC CAT CTG AGT TCA CTT TGC ATC TCA ATT      289
Glu Gln Pro Ser Thr Pro Ala His Leu Ser Ser Leu Cys Ile Ser Ile
                85                  90                  95
```

```
TTG TTC TTC AAC ATA TTT GAT CCT CTG CCA GCT TTG AGT CAT CTT CAG      337
Leu Phe Phe Asn Ile Phe Asp Pro Leu Pro Ala Leu Ser His Leu Gln
            100                 105                 110

ACG TGG AGC TGT GAA AAT CAG CTG CAA CTG AAA ATG TCT GAC AGC TTG      385
Thr Trp Ser Cys Glu Asn Gln Leu Gln Leu Lys Met Ser Asp Ser Leu
        115                 120                 125

GAT AAC GAA GAA AAA CCT CCA GCT CCC ACT GAG GAT GAC AGT AAC ACC      433
Asp Asn Glu Glu Lys Pro Pro Ala Pro Thr Glu Asp Asp Ser Asn Thr
    130                 135                 140

GAG ATT CTT CAG CAC TCA ACC ACA GCT CCA AAC CAC TGC CCA TGC GCC      481
Glu Ile Leu Gln His Ser Thr Thr Ala Pro Asn His Cys Pro Cys Ala
145                 150                 155                 160

CGG AAG AGA AGA ATA AGA AAG CCA GGC TTC GCT CTA TCT TCC CAG GAG      529
Arg Lys Arg Arg Ile Arg Lys Pro Gly Phe Ala Leu Ser Ser Gln Glu
                165                 170                 175

GAG GGG ATA AAA CCA ATA AGA AGA AAG AGA AAG AAC GCC CAG AGA TCT      577
Glu Gly Ile Lys Pro Ile Arg Arg Lys Arg Lys Asn Ala Gln Arg Ser
            180                 185                 190

CTC TTC CTT CAG ACT TTG AGC ATA CGA TTC ATG TGG GTT TTG ATG CAG      625
Leu Phe Leu Gln Thr Leu Ser Ile Arg Phe Met Trp Val Leu Met Gln
        195                 200                 205

TCA CCG GGG AAT TCA CTC CAG ATC TCT ATG GCT CAC AGA TGT GCC CAG      673
Ser Pro Gly Asn Ser Leu Gln Ile Ser Met Ala His Arg Cys Ala Gln
    210                 215                 220

GAA GCT CCA GAG GGA ATT CCT GAA CAA TGG GCT CGA CTG CTC CAA AC       720
Glu Ala Pro Glu Gly Ile Pro Glu Gln Trp Ala Arg Leu Leu Gln
225                 230                 235
```

(2) INFORMATION FOR SEQ ID NO:17:

(i) SEQUENCE CHARACTERISTICS:
        (A) LENGTH: 239 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:17:

```
Asn Ser His Met Ile Phe Trp Ala Pro Pro Lys Gly Trp His Tyr Phe
1               5                   10                  15

Ser Ser Ser Thr Leu Cys Ser Thr Leu Ser Ser Gly Arg Pro Pro Pro
            20                  25                  30

Thr Thr Ala Ala Ala Val Ile Ala Tyr Pro Leu Ser Ser Phe Leu
        35                  40                  45

Ala Asn Phe Cys Ser Ser Arg Ile Pro Leu Leu Gln Gln Leu Lys
    50                  55                  60

Ala Glu Leu Arg Gln Gln Leu Ser Phe Ser Pro Ala Thr Lys Arg Leu
65                  70                  75                  80

Glu Gln Pro Ser Thr Pro Ala His Leu Ser Ser Leu Cys Ile Ser Ile
                85                  90                  95

Leu Phe Phe Asn Ile Phe Asp Pro Leu Pro Ala Leu Ser His Leu Gln
            100                 105                 110

Thr Trp Ser Cys Glu Asn Gln Leu Gln Leu Lys Met Ser Asp Ser Leu
        115                 120                 125

Asp Asn Glu Glu Lys Pro Pro Ala Pro Thr Glu Asp Asp Ser Asn Thr
    130                 135                 140

Glu Ile Leu Gln His Ser Thr Thr Ala Pro Asn His Cys Pro Cys Ala
145                 150                 155                 160
```

-continued

```
Arg Lys Arg Arg Ile Arg Lys Pro Gly Phe Ala Leu Ser Ser Gln Glu
                165                 170                 175

Glu Gly Ile Lys Pro Ile Arg Arg Lys Arg Lys Asn Ala Gln Arg Ser
            180                 185                 190

Leu Phe Leu Gln Thr Leu Ser Ile Arg Phe Met Trp Val Leu Met Gln
        195                 200                 205

Ser Pro Gly Asn Ser Leu Gln Ile Ser Met Ala His Arg Cys Ala Gln
    210                 215                 220

Glu Ala Pro Glu Gly Ile Pro Glu Gln Trp Ala Arg Leu Leu Gln
225                 230                 235
```

(2) INFORMATION FOR SEQ ID NO:18:

(i) SEQUENCE CHARACTERISTICS:
        (A) LENGTH: 2390 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 309...1940
        (D) OTHER INFORMATION:

(xi) SEQUENCE DESCRIPTION: SEQ ID NO:18:

```
GGCACGAGGC CDAACAAGTA GGTCAGCTCC TCCTGATCAA ATGATATTAC AAATGGCTTC     60

CCTCCATTAT CCACTGTAAT GGTATCTCCC TGGCGAGCTG CTCTGAAACA GCACACCCCT    120

GTCTCCGATA GCAGTATTCT CTTGGTGAGT GCTCCCAGAA GAGGCAAGCT CCAAAACAAG    180

GACATCTAAG AACTGGTACA ATTGGTCAAC AAAAACTTTT GGAGTTCTAT CAATAAACCG    240

AATAGCCTTG GGTCTTTGGA TGGGAAAAGC AAATGAACCC AGAGCTGTGA AATCAGCTGC    300

AACTGAAAATG TCT GAC AGC TTG GAT AAC GAA GAA AAA CCT CCA GCT CCC     350
            Met Ser Asp Ser Leu Asp Asn Glu Glu Lys Pro Pro Ala Pro
              1               5                  10

CCA CTG AGG ATG AAC AGT AAC AAC CGA GAT TCT TCA GCA CTC AAC CAC     398
Pro Leu Arg Met Asn Ser Asn Asn Arg Asp Ser Ser Ala Leu Asn His
15              20                  25                  30

AGA GCC AAA CCA CTG CCC ATG GCC CCG GAA GAG AAG AAT AAG AAA GCC     446
Arg Ala Lys Pro Leu Pro Met Ala Pro Glu Glu Lys Asn Lys Lys Ala
                35                  40                  45

AGG CTT CGC TCT ATC TTC CCA GGA GGA GGG GAT AAA ACC AAT AAG AAG     494
Arg Leu Arg Ser Ile Phe Pro Gly Gly Gly Asp Lys Thr Asn Lys Lys
            50                  55                  60

AAA GAG AAA GAA CGC CCA GAG ATC TCT CTT CCT TCA GAC TTT GAG CAT     542
Lys Glu Lys Glu Arg Pro Glu Ile Ser Leu Pro Ser Asp Phe Glu His
65              70                  75

ACG ATT CAT GTG GGT TTT GAT GCA GTC ACC GGG GAA TTA ACC GGA ATT     590
Thr Ile His Val Gly Phe Asp Ala Val Thr Gly Glu Leu Thr Gly Ile
    80                  85                  90

CCT GAA CAA TGG GCT CGA CTG CTC CAA ACC TCC AAC ATA ACA AAA CTG     638
Pro Glu Gln Trp Ala Arg Leu Leu Gln Thr Ser Asn Ile Thr Lys Leu
95              100                 105                 110

GAA CAG AAG AAG AAC CCA CAG GCT GTT CTG GAT GTT CTC AAG TTT TAC     686
Glu Gln Lys Lys Asn Pro Gln Ala Val Leu Asp Val Leu Lys Phe Tyr
                115                 120                 125

GAC TCC AAA GAA ACA GTC AAC AAC CAG AAA TAC ATG AGC TTT ACA TCA     734
Asp Ser Lys Glu Thr Val Asn Asn Gln Lys Tyr Met Ser Phe Thr Ser
            130                 135                 140
```

```
GGA GAT AAA AGT GCC CAT GGA TAT ATA GCA GCA CAT CAG TCG AAT ACC      782
Gly Asp Lys Ser Ala His Gly Tyr Ile Ala Ala His Gln Ser Asn Thr
        145                 150                 155

AAA ACA GCT TCA GAA CCT CCT TTG GCT CCT CCT GTA TCT GAA GAA GAG      830
Lys Thr Ala Ser Glu Pro Pro Leu Ala Pro Pro Val Ser Glu Glu Glu
160                 165                 170

GAT GAA GAA GAG GAA GAG GAA GAA GAT GAT AAT GAG CCC CCG CCT GTC      878
Asp Glu Glu Glu Glu Glu Glu Glu Asp Asp Asn Glu Pro Pro Pro Val
175                 180                 185                 190

ATT GCA CCA AGA CCA GAG CAT ACA AAA TCA ATC TAT ACT CGT TCT GTG      926
Ile Ala Pro Arg Pro Glu His Thr Lys Ser Ile Tyr Thr Arg Ser Val
                195                 200                 205

GTT GAG TCA ATT GCT TCA CCA GCA GCA CCA AAT AAA GAA GCC ACC CCA      974
Val Glu Ser Ile Ala Ser Pro Ala Ala Pro Asn Lys Glu Ala Thr Pro
            210                 215                 220

CCT TCT GCT GAG AAT GCC AAT TCC AGT ACT TTG TAC AGG AAT ACA GAT     1022
Pro Ser Ala Glu Asn Ala Asn Ser Ser Thr Leu Tyr Arg Asn Thr Asp
        225                 230                 235

CGG CAA AGA AAA AAA TCC AAG ATG ACA GAT GAG GAG ATC CTA GAG AAG     1070
Arg Gln Arg Lys Lys Ser Lys Met Thr Asp Glu Glu Ile Leu Glu Lys
    240                 245                 250

CTA AGA AGC ATT GTG AGT GTT GGG GAD CCA AAG AAG AAA TAT ACA AGA     1118
Leu Arg Ser Ile Val Ser Val Gly Xaa Pro Lys Lys Lys Tyr Thr Arg
255                 260                 265                 270

TTT GAA AAA ATT GGC CAA GGG GCA TCA GGA ACT GTT TAC ACA GCA CTA     1166
Phe Glu Lys Ile Gly Gln Gly Ala Ser Gly Thr Val Tyr Thr Ala Leu
                275                 280                 285

GAC ATT GCG ACA GGA CAA GAG GTG GCT ATA AAG CAA ATG AAC CTT CAA     1214
Asp Ile Ala Thr Gly Gln Glu Val Ala Ile Lys Gln Met Asn Leu Gln
            290                 295                 300

CAG CAG CCC AAA AAG GAA TTA ATT ATT AAT GAA ATT CTT GTC ATG AGG     1262
Gln Gln Pro Lys Lys Glu Leu Ile Ile Asn Glu Ile Leu Val Met Arg
        305                 310                 315

GAA AAT AAG AAC CCC AAT ATT GTC AAT TAT TTA GAT AGC TAC TTA GTG     1310
Glu Asn Lys Asn Pro Asn Ile Val Asn Tyr Leu Asp Ser Tyr Leu Val
    320                 325                 330

GGT GAT GAA CTG TGG GTA GTC ATG GAA TAC TTG GCT GGT GGC TCT TTG     1358
Gly Asp Glu Leu Trp Val Val Met Glu Tyr Leu Ala Gly Gly Ser Leu
335                 340                 345                 350

ACT GAC GTG GTC ACA GAA ACC TGT ATG GAT GAA GGA CAG ATA GCA GCC     1406
Thr Asp Val Val Thr Glu Thr Cys Met Asp Glu Gly Gln Ile Ala Ala
                355                 360                 365

GTC TGT AGA GAG TGC CTC CAA GCT TTG GAT TTC TTG CAC TCA AAC CAA     1454
Val Cys Arg Glu Cys Leu Gln Ala Leu Asp Phe Leu His Ser Asn Gln
            370                 375                 380

GTG ATC CAC AGA GAT ATA AAG ATG GAC AAT ATT CTC CTC GGG ATG GAT     1502
Val Ile His Arg Asp Ile Lys Met Asp Asn Ile Leu Leu Gly Met Asp
        385                 390                 395

GGT TCT GTT AAA CTG ACT GAT TTT GGA TTC TGT GCC CAA ATC ACT CCT     1550
Gly Ser Val Lys Leu Thr Asp Phe Gly Phe Cys Ala Gln Ile Thr Pro
    400                 405                 410

GAG CAA AGT AAA CGA AGC ACT ATG GTG GGA ACT CCC TAT TGG ATG GCA     1598
Glu Gln Ser Lys Arg Ser Thr Met Val Gly Thr Pro Tyr Trp Met Ala
415                 420                 425                 430

CCT GAG GTG GTA ACT CGA AAA GCT TAT GGC CCG AAA GTT GAT ATC TGG     1646
Pro Glu Val Val Thr Arg Lys Ala Tyr Gly Pro Lys Val Asp Ile Trp
                435                 440                 445

TCT CTG GGA ATC ATG GCC ATT GAA ATG GTG GAA GGC GAA CCC CCT TAC     1694
Ser Leu Gly Ile Met Ala Ile Glu Met Val Glu Gly Glu Pro Pro Tyr
            450                 455                 460
```

-continued

```
CTT AAT GAA AAT CCA CTC AGG GCC TTA TAT CTG ATA GCC ACT AAT GGA    1742
Leu Asn Glu Asn Pro Leu Arg Ala Leu Tyr Leu Ile Ala Thr Asn Gly
            465                 470                 475

ACC CCC GAG CTC CAG AAT CCC GAG AGA CTG TCA GCT GTA TTC CGT GAC    1790
Thr Pro Glu Leu Gln Asn Pro Glu Arg Leu Ser Ala Val Phe Arg Asp
480                 485                 490

TTC TTA AAT CGC TGT CTT GAG ATG GAT GTG GAT AGA CGA GGG TCT GCC    1838
Phe Leu Asn Arg Cys Leu Glu Met Asp Val Asp Arg Arg Gly Ser Ala
495                 500                 505                 510

AAG GAG CTT TTG CAG CAT CCA TTT TTA AAA TTA GCC AAG CCC CTG TCC    1886
Lys Glu Leu Leu Gln His Pro Phe Leu Lys Leu Ala Lys Pro Leu Ser
                515                 520                 525

AGC CTC ACT CCT CTG ATT CTT GCT GCA AAG GAA GCC ATT AAG AAC AGT    1934
Ser Leu Thr Pro Leu Ile Leu Ala Ala Lys Glu Ala Ile Lys Asn Ser
            530                 535                 540

AGC CGT TAGAAGTGCA AGCCTTACCC CTCACCGTCT CCCGGATGAG TAAGACTGAA CT  1992
Ser Arg

AAAACTCTGC TGCAGGATCC ACAGAAGAAA AGACAGTCAA ATGGAGTGGG GGTTCTTTAA  2052

CTTTCAAGTG AATAGAAACT TCTTACAAAC CTTTTTCCTA CTCCCTCAGA TTATGTAATT  2112

TATTTGTAAG CCTGAACCGC AGCCCACACA GGGCAGCAAT GTCGAAGTAG CCATTAAGTG  2172

GCCAACTTCC ACCGTGAAGC GAGAGAGCCA GTATTGAATC CCCTCATTCG TGCATTTACT  2232

TTGAAGAAAA AGAGATTTCT CAAAGATGCA CACTCCCTCT TCATAGTGCT GTGTGTTTTT  2292

AAGTTAGAGA GTATTCCCCC TCCATTCAAA CCTCTTTCAA AATCCCTTAC CCAACGTGAT  2352

GTTTTTTCAC TTGCATTGTC ATTAGATGTC CAGAAAAA                          2390
```

(2) INFORMATION FOR SEQ ID NO:19:

(i) SEQUENCE CHARACTERISTICS:
  (A) LENGTH: 544 amino acids
  (B) TYPE: amino acid
  (C) STRANDEDNESS:
  (D) TOPOLOGY: unknown (ii) MOLECULE TYPE: peptide (xi) SEQUENCE DESCRIPTION: SEQ ID NO:19:

```
Met Ser Asp Ser Leu Asp Asn Glu Glu Lys Pro Ala Pro Pro Leu
1               5                   10                  15

Arg Met Asn Ser Asn Asn Arg Asp Ser Ser Ala Leu Asn His Arg Ala
                20                  25                  30

Lys Pro Leu Pro Met Ala Pro Glu Glu Lys Asn Lys Lys Ala Arg Leu
            35                  40                  45

Arg Ser Ile Phe Pro Gly Gly Asp Lys Thr Asn Lys Lys Lys Glu
        50                  55                  60

Lys Glu Arg Pro Glu Ile Ser Leu Pro Ser Asp Phe Glu His Thr Ile
65                  70                  75                  80

His Val Gly Phe Asp Ala Val Thr Gly Glu Leu Thr Gly Ile Pro Glu
                85                  90                  95

Gln Trp Ala Arg Leu Leu Gln Thr Ser Asn Ile Thr Lys Leu Glu Gln
                100                 105                 110

Lys Lys Asn Pro Gln Ala Val Leu Asp Val Leu Lys Phe Tyr Asp Ser
            115                 120                 125

Lys Glu Thr Val Asn Asn Gln Lys Tyr Met Ser Phe Thr Ser Gly Asp
        130                 135                 140

Lys Ser Ala His Gly Tyr Ile Ala Ala His Gln Ser Asn Thr Lys Thr
```

```
        145                 150                 155                 160
   Ala Ser Glu Pro Pro Leu Ala Pro Pro Val Ser Glu Glu Asp Glu
                   165                 170                 175

Glu Glu Glu Glu Glu Asp Asp Asn Glu Pro Pro Val Ile Ala
               180                 185                 190

Pro Arg Pro Glu His Thr Lys Ser Ile Tyr Thr Arg Ser Val Val Glu
                   195                 200                 205

Ser Ile Ala Ser Pro Ala Ala Pro Asn Lys Glu Ala Thr Pro Pro Ser
           210                 215                 220

Ala Glu Asn Ala Asn Ser Ser Thr Leu Tyr Arg Asn Thr Asp Arg Gln
   225                 230                 235                 240

Arg Lys Lys Ser Lys Met Thr Asp Glu Glu Ile Leu Glu Lys Leu Arg
                   245                 250                 255

Ser Ile Val Ser Val Gly Xaa Pro Lys Lys Tyr Thr Arg Phe Glu
                   260                 265                 270

Lys Ile Gly Gln Gly Ala Ser Gly Thr Val Tyr Thr Ala Leu Asp Ile
               275                 280                 285

Ala Thr Gly Gln Glu Val Ala Ile Lys Gln Met Asn Leu Gln Gln Gln
   290                 295                 300

Pro Lys Lys Glu Leu Ile Ile Asn Glu Ile Leu Val Met Arg Glu Asn
   305                 310                 315                 320

Lys Asn Pro Asn Ile Val Asn Tyr Leu Asp Ser Tyr Leu Val Gly Asp
                   325                 330                 335

Glu Leu Trp Val Val Met Glu Tyr Leu Ala Gly Gly Ser Leu Thr Asp
                   340                 345                 350

Val Val Thr Glu Thr Cys Met Asp Glu Gly Gln Ile Ala Ala Val Cys
               355                 360                 365

Arg Glu Cys Leu Gln Ala Leu Asp Phe Leu His Ser Asn Gln Val Ile
   370                 375                 380

His Arg Asp Ile Lys Met Asp Asn Ile Leu Leu Gly Met Asp Gly Ser
   385                 390                 395                 400

Val Lys Leu Thr Asp Phe Gly Phe Cys Ala Gln Ile Thr Pro Glu Gln
                   405                 410                 415

Ser Lys Arg Ser Thr Met Val Gly Thr Pro Tyr Trp Met Ala Pro Glu
                   420                 425                 430

Val Val Thr Arg Lys Ala Tyr Gly Pro Lys Val Asp Ile Trp Ser Leu
               435                 440                 445

Gly Ile Met Ala Ile Glu Met Val Glu Gly Glu Pro Pro Tyr Leu Asn
   450                 455                 460

Glu Asn Pro Leu Arg Ala Leu Tyr Leu Ile Ala Thr Asn Gly Thr Pro
   465                 470                 475                 480

Glu Leu Gln Asn Pro Glu Arg Leu Ser Ala Val Phe Arg Asp Phe Leu
                   485                 490                 495

Asn Arg Cys Leu Glu Met Asp Val Asp Arg Arg Gly Ser Ala Lys Glu
                   500                 505                 510

Leu Leu Gln His Pro Phe Leu Lys Leu Ala Lys Pro Leu Ser Ser Leu
                   515                 520                 525

Thr Pro Leu Ile Leu Ala Ala Lys Glu Ala Ile Lys Asn Ser Ser Arg
           530                 535                 540

(2) INFORMATION FOR SEQ ID NO:20:

(i) SEQUENCE CHARACTERISTICS:
        (A) LENGTH: 100 base pairs
```

```
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

AATAAGAAGA AGGAGAAAGA GCGCCAGAGA TCTCTCTCCT TCAGACTTTG AGCATACGAT    60

TCATGTGGGG TTGATGCAGT CACCGGGAAT TCACTCCAGA                         100

(2) INFORMATION FOR SEQ ID NO:21:

(i) SEQUENCE CHARACTERISTICS:
        (A) LENGTH: 104 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

AATAAGAAGA AAGAGAAAGA ACGCCCAGAG ATCTCTCTTC CTTCAGACTT TGAGCATACG    60

ATTCATGTGG GTTTTGATGC AGTCACCGGG GAATTCACTC CAGA                    104

(2) INFORMATION FOR SEQ ID NO:22:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

TTACAGAGGA CGATAAATGA TTCCATGTGG ATAGGGCATA ACAT                     44

(2) INFORMATION FOR SEQ ID NO:23:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

TTACATCAGG AGATAAAAGT GCCCATGGAT ATATAGCAGC ACAT                     44

(2) INFORMATION FOR SEQ ID NO:24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

NAAAAAACAA AAGCAAAA                                                  18

(2) INFORMATION FOR SEQ ID NO:25:

(i) SEQUENCE CHARACTERISTICS:
        (A) LENGTH: 18 base pairs
```

(B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

AAAAAAAAGA AAGCAAAA                                                 18

(2) INFORMATION FOR SEQ ID NO:26:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

GGAATTCTGC CAGTTTATTA CAGAGGACGA TAAATGATTC CATGTGGATA GGGCATAACA    60

TACAGAGAAT GAGACTATGC CAGA                                          84

(2) INFORMATION FOR SEQ ID NO:27:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

GGAATTCCCA GTGGAAACCA AATGAAACGA CTTTGNCTTG TNGAGGGGGA AGAATGTGAA    60

MAAAAAACAA AAGCAAAATG ACCCGCCCAC AAGATACAAC AGAAACCCCA TCCACTACCC   120

ATCCCTTCCA TGTGAGGCCG ACCACCCAGG CCCCAACACC CT                     162

(2) INFORMATION FOR SEQ ID NO:28:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

GGAATTCCAA TAAGAAGAAG GAGAAAGAGC GCCCAGAGAT CTCTCTTCCT TCAGACTTTG    60

AGCATACGAT TCATGTGGGG TTGATGCAGT CACCGGGAAT TCACTCCAGA             110

(2) INFORMATION FOR SEQ ID NO:29:

(i) SEQUENCE CHARACTERISTICS:
        (A) LENGTH: 544 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:29:

Met Ser Asp Ser Leu Asp Asn Glu Glu Lys Pro Ala Pro Pro Leu Arg
1               5                   10                  15

-continued

```
Arg Met Asn Ser Asn Asn Arg Asp Ser Ser Ala Leu Asn His Ser Ser
         20                  25                  30

Lys Pro Leu Pro Met Ala Pro Glu Glu Lys Asn Lys Lys Ala Arg Leu
         35                  40                  45

Arg Ser Ile Phe Pro Gly Gly Gly Asp Lys Thr Asn Lys Lys Lys Glu
 50                  55                  60

Lys Glu Arg Pro Glu Ile Ser Leu Pro Ser Asp Phe Glu His Thr Ile
 65                  70                  75                  80

His Val Gly Phe Asp Ala Val Thr Gly Glu Phe Thr Gly Ile Pro Glu
                 85                  90                  95

Gln Trp Ala Arg Glu Glu Gln Thr Ser Asn Ile Thr Lys Leu Glu Gln
             100                 105                 110

Lys Lys Asn Pro Gln Ala Val Leu Asp Val Leu Lys Phe Tyr Gln Ser
             115                 120                 125

Lys Glu Thr Val Asn Asn Gln Lys Tyr Met Ser Phe Thr Ser Gly Asp
             130                 135                 140

Lys Ser Ala His Gly Tyr Ile Ala Ala His Gln Ser Asn Thr Lys Thr
145                 150                 155                 160

Ala Ser Glu Pro Pro Leu Ala Pro Val Ser Glu Glu Asp Glu
                 165                 170                 175

Glu Glu Glu Glu Glu Asp Asp Asn Glu Pro Pro Val Ile Ala
             180                 185                 190

Pro Arg Pro Glu His Thr Lys Ser Ile Tyr Thr Arg Ser Val Val Glu
             195                 200                 205

Ser Ile Ala Ser Pro Ala Ala Pro Asn Lys Glu Ala Thr Pro Pro Ser
210                 215                 220

Ala Glu Asn Ala Asn Ser Ser Thr Leu Tyr Arg Asn Thr Asp Arg Gln
225                 230                 235                 240

Arg Lys Lys Ser Lys Met Thr Asp Glu Glu Ile Leu Glu Lys Leu Arg
                 245                 250                 255

Ser Ile Val Ser Val Gly Asp Pro Lys Lys Tyr Thr Arg Glu Glu
                 260                 265                 270

Lys Ile Gly Gln Gly Ala Ser Gly Thr Val Tyr Thr Ala Leu Asp Ile
             275                 280                 285

Ala Thr Gly Gln Glu Val Ala Ile Lys Gln Met Asn Leu Gln Gln Gln
290                 295                 300

Pro Lys Lys Glu Leu Ile Ile Asn Glu Ile Leu Val Met Arg Glu Asn
305                 310                 315                 320

Lys Asn Pro Asn Ile Val Asn Tyr Leu Asp Ser Tyr Ser Val Gly Asp
                 325                 330                 335

Glu Leu Trp Val Val Met Glu Tyr Leu Ala Gly Glu Ser Leu Thr Asp
                 340                 345                 350

Val Val Thr Glu Thr Cys Met Asp Glu Gly Gln Ile Ala Ala Val Glu
                 355                 360                 365

Arg Glu Cys Leu Gln Ala Leu Asp Phe Leu His Ser Asn Gln Val Ile
             370                 375                 380

His Arg Asp Ile Lys Ser Asp Asn Ile Leu Leu Gly Met Asp Gly Ser
385                 390                 395                 400

Val Lys Leu Thr Asp Phe Gly Phe Cys Ala Gln Ile Thr Pro Glu Gln
                 405                 410                 415

Ser Lys Arg Ser Thr Met Val Gly Thr Pro Tyr Trp Met Ala Pro Glu
                 420                 425                 430

Val Val Thr Arg Lys Ala Tyr Gly Pro Lys Val Asp Ile Trp Ser Leu
```

-continued

```
                435                 440                 445
Gly Ile Met Ala Ile Glu Met Val Glu Gly Glu Pro Pro Tyr Leu Asn
    450                 455                 460

Glu Asn Pro Leu Arg Ala Leu Tyr Leu Ile Ala Thr Asn Gly Thr Pro
465                 470                 475                 480

Glu Leu Gln Asn Pro Glu Arg Leu Ser Ala Val Glu Arg Asp Phe Leu
                485                 490                 495

Asn Arg Cys Leu Glu Met Asp Val Asp Arg Arg Gly Ser Ala Lys Glu
            500                 505                 510

Leu Leu Gln His Pro Phe Leu Lys Leu Ala Lys Pro Leu Ser Ser Leu
        515                 520                 525

Thr Pro Leu Ile Leu Ala Ala Lys Glu Ala Ile Lys Asn Ser Ser Arg
530                 535                 540
```

(2) INFORMATION FOR SEQ ID NO:30:

(i) SEQUENCE CHARACTERISTICS:
        (A) LENGTH: 544 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:30:

```
Met Ser Asn Asn Gly Leu Asp Val Gln Asp Lys Pro Pro Ala Pro Pro
1               5                   10                  15

Met Arg Asn Thr Ser Thr Met Ile Gly Ala Gly Ser Lys Asp Pro Gly
            20                  25                  30

Thr Leu Asn His Gly Ser Lys Pro Leu Pro Pro Asn Pro Glu Glu Lys
        35                  40                  45

Lys Lys Lys Asp Arg Phe Tyr Arg Ser Ile Leu Ala Gly Asp Lys Thr
    50                  55                  60

Asn Lys Lys Lys Glu Lys Glu Arg His Glu Ile Ser Leu Pro Ser Asp
65                  70                  75                  80

Phe Glu His Thr Ile His Val Gly Phe Asp Ala Gln Thr Gly Glu Phe
                85                  90                  95

Thr Gly Met Pro Glu Gln Trp Ala Arg Glu Glu Gln Thr Ser Asn Ile
            100                 105                 110

Thr Lys Ser Glu Gln Lys Lys Asn Pro Gln Ala Val Leu Asp Val Leu
        115                 120                 125

Glu Phe Tyr Asn Ser Lys Lys Thr Ser Asn Ser Gln Lys Tyr Met Ser
    130                 135                 140

Phe Thr Asp Lys Ser Ala Glu Asp Tyr Asn Ser Ser Asn Thr Leu Asn
145                 150                 155                 160

Val Lys Thr Tyr Ser Glu Thr Pro Ala Val Pro Pro Val Ser Glu Asp
                165                 170                 175

Glu Asp Asp Asp Asp Ala Thr Pro Pro Pro Val Ile Ala Pro Arg
            180                 185                 190

Pro Glu His Thr Lys Ser Val Tyr Thr Arg Ser Val Ile Glu Pro Leu
        195                 200                 205

Pro Val Thr Pro Thr Arg Asp Val Ala Thr Ser Pro Ile Ser Pro Thr
    210                 215                 220

Glu Asn Asn Thr Thr Pro Pro Asp Ala Leu Thr Arg Asn Thr Glu Lys
225                 230                 235                 240

Gln Lys Lys Lys Pro Lys Met Ser Asp Glu Glu Ile Leu Glu Lys Leu
```

-continued

```
                245                 250                 255
Arg Asn Ile Val Ser Val Gly Asp Pro Lys Lys Tyr Thr Arg Glu
                260                 265                 270
Glu Asp Ile Gly Gln Gly Ala Ser Ser Thr Val Tyr Thr Ala Met Asp
            275                 280                 285
Val Ala Thr Gly Gln Glu Val Ala Ile Leu Gln Met Asn Leu Gln Gln
        290                 295                 300
Gln Pro Lys Lys Glu Leu Ile Ile Asn Glu Thr Leu Val Met Arg Glu
305                 310                 315                 320
Asn Lys Asn Pro Asn Ile Val Asn Tyr Leu Asp Ser Tyr Leu Val Gly
                325                 330                 335
Asp Glu Leu Trp Val Val Met Glu Tyr Leu Ala Gly Gly Ser Leu Thr
            340                 345                 350
Asp Val Val Thr Glu Thr Cys Met Asp Glu Gly Gln Ile Ala Ala Val
        355                 360                 365
Cys Arg Glu Cys Leu Gln Ala Leu Glu Phe Leu His Ser Asn Gln Val
    370                 375                 380
Ile His Arg Asp Ile Asp Ser Asp Asn Ile Leu Leu Gly Met Asp Gly
385                 390                 395                 400
Ser Val Lys Leu Thr Asp Phe Gly Phe Cys Ala Gln Ile Thr Pro Glu
                405                 410                 415
Gln Ser Lys Arg Ser Thr Met Val Gly Thr Pro Tyr Trp Met Ala Pro
            420                 425                 430
Glu Val Val Thr Arg Lys Ala Tyr Gly Pro Lys Val Asp Ile Trp Ser
        435                 440                 445
Leu Gly Ile Met Ala Ile Glu Met Ile Glu Gly Glu Pro Pro Tyr Leu
    450                 455                 460
Asn Glu Asn Pro Leu Arg Ala Leu Tyr Leu Ile Ala Thr Asn Gly Thr
465                 470                 475                 480
Pro Glu Leu Gln Asn Pro Glu Lys Leu Ser Ala Ile Phe Arg Asp Phe
                485                 490                 495
Leu Asn Arg Cys Leu Glu Met Asp Val Glu Lys Arg Gly Ser Ala Lys
            500                 505                 510
Glu Leu Leu Gln His Gln Phe Leu Lys Ile Ala Lys Pro Leu Ser Ser
        515                 520                 525
Leu Thr Pro Leu Ile Ala Ala Ala Lys Glu Ala Thr Lys Asn Asn His
    530                 535                 540
```

(2) INFORMATION FOR SEQ ID NO:31:

(i) SEQUENCE CHARACTERISTICS:
        (A) LENGTH: 694 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:31:

```
Gln Ile Asn Ser Ala Ser His Ser Leu Ser Asn Pro Lys His Lys Gln
1               5                   10                  15
His Lys Pro Lys Val Lys Pro Ser Lys Pro Glu Ala Lys Ser Lys Pro
            20                  25                  30
Val Ser Val Lys Lys Ser Phe Pro Ser Lys Asn Pro Leu Lys Asn Ser
        35                  40                  45
Ser Pro Pro Lys Lys Gln Thr Glu Lys Ser Tyr Tyr Ser Ser Ser Ser
```

```
              50                  55                  60
Lys Lys Arg Lys Ser Gly Ser Asn Ser Gly Thr Leu Arg Met Lys Asp
 65                  70                  75                  80

Val Phe Thr Ser Phe Val Gln Asn Ile Lys Arg Asn Ser Gln Asp Asp
                 85                  90                  95

Lys Arg Ala Ser Ser Ser Asn Ser Ser Ser Ser Ser Ile Thr
                100                 105                 110

Thr Ala Leu Arg Ile Ser Thr Pro Tyr Asn Ala Lys His Ile His His
                115                 120                 125

Val Gly Val Asp Ser Lys Thr Gly Glu Tyr Thr Gly Leu Pro Glu Glu
130                 135                 140

Trp Glu Lys Glu Glu Thr Ser Ser Gly Ile Ser Lys Arg Glu Gln Gln
145                 150                 155                 160

Gln Asn Met Gln Ala Val Met Asp Ile Val Lys Phe Tyr Gln Asp Val
                165                 170                 175

Thr Glu Thr Asn Gly Glu Asp Lys Met Phe Lys Thr Phe Asn Thr Thr
                180                 185                 190

Thr Gly Leu Pro Gly Ser Pro Gln Val Ser Thr Pro Ala Asn Ser
                195                 200                 205

Phe Asn Lys Phe Pro Pro Ser Thr Ser Asp Ser His Asn Tyr Gly Ser
210                 215                 220

Arg Thr Gly Thr Pro Met Ser Asn His Val Met Ser Pro Thr Leu Asn
225                 230                 235                 240

Thr Asp Ser Ser Ser Ala Asn Gly Lys Phe Ile Pro Ser Arg Pro Ala
                245                 250                 255

Pro Lys Pro Pro Ser Ser Ala Ser Ala Ser Ala Pro Ile Ile Lys Ser
                260                 265                 270

Pro Val Met Asn Ser Ala Ala Asn Val Ser Pro Leu Lys Gln Thr His
                275                 280                 285

Ala Pro Thr Thr Pro Asn Arg Thr Ser Pro Asn Arg Ser Ser Ile Ser
                290                 295                 300

Arg Asn Ala Thr Leu Lys Lys Glu Glu Gln Pro Leu Pro Pro Ile Pro
305                 310                 315                 320

Pro Thr Lys Ser Lys Thr Ser Pro Ile Ile Ser Thr Ala His Thr Pro
                325                 330                 335

Gln Gln Val Ala Gln Ser Pro Lys Ala Pro Ala Gln Glu Thr Val Thr
                340                 345                 350

Thr Pro Thr Ser Lys Pro Ala Gln Ala Arg Ser Leu Ser Lys Glu Leu
                355                 360                 365

Asn Glu Lys Lys Arg Glu Glu Arg Glu Arg Lys Lys Gln Leu Tyr
                370                 375                 380

Ala Lys Leu Asn Glu Ile Cys Ser Asp Gly Asp Pro Ser Thr Lys Tyr
385                 390                 395                 400

Ala Asn Leu Val Lys Ile Gly Gln Gly Ala Ser Gly Val Tyr Thr
                405                 410                 415

Ala Tyr Glu Ile Gly Thr Asn Val Ser Val Ala Ile Lys Gln Met Asn
                420                 425                 430

Leu Glu Lys Gln Pro Lys Lys Glu Leu Ile Ile Asn Glu Ile Leu Val
                435                 440                 445

Met Lys Gly Ser Lys His Pro Asn Ile Val Asn Phe Ile Asp Ser Tyr
                450                 455                 460

Val Leu Lys Gly Asp Leu Trp Val Ile Met Glu Tyr Met Glu Gly Gly
465                 470                 475                 480
```

```
Ser Leu Thr Asp Val Val Thr His Cys Ile Leu Thr Glu Gly Gln Ile
                485                 490                 495

Gly Ala Val Cys Arg Glu Thr Leu Ser Gly Leu Glu Phe Leu His Ser
            500                 505                 510

Lys Gly Val Leu His Arg Asp Ile Lys Ser Asp Asn Ile Leu Leu Ser
        515                 520                 525

Met Glu Gly Asp Ile Lys Leu Thr Lys Phe Gly Phe Cys Ala Gln Ile
    530                 535                 540

Asn Glu Leu Asn Leu Lys Arg Thr Thr Met Val Gly Thr Pro Tyr Trp
545                 550                 555                 560

Met Ala Pro Glu Val Val Ser Arg Lys Glu Tyr Gly Pro Lys Val Asp
                565                 570                 575

Ile Trp Ser Leu Gly Ile Met Ile Ile Glu Met Ile Glu Gly Glu Pro
            580                 585                 590

Pro Tyr Leu Asn Glu Thr Pro Leu Arg Ala Leu Tyr Leu Ile Ala Thr
        595                 600                 605

Asn Gly Thr Pro Lys Leu Lys Glu Pro Glu Asn Leu Ser Ser Ser Leu
    610                 615                 620

Lys Lys Phe Leu Asp Trp Cys Leu Cys Val Glu Pro Glu Asp Arg Ala
625                 630                 635                 640

Ser Ala Thr Glu Leu Leu His Asp Glu Tyr Ile Thr Glu Ile Ala Glu
                645                 650                 655

Ala Asn Ser Ser Leu Ala Pro Leu Val Lys Leu Ala Arg Leu Lys Lys
            660                 665                 670

Val Ala Glu Asn Met Asp Ala Asp Glu Asp Asn Asp Asp Asp Asn Asp
        675                 680                 685

Asn Glu His Ile Asn Lys
    690

(2) INFORMATION FOR SEQ ID NO:32:

(i) SEQUENCE CHARACTERISTICS:
        (A) LENGTH: 13 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:32:

Ser Pro Ala Ala Pro Asn Lys Glu Ala Thr Pro Pro Ser
1               5                   10

(2) INFORMATION FOR SEQ ID NO:33:

(i) SEQUENCE CHARACTERISTICS:
        (A) LENGTH: 15 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:33:

Asn Thr Asp Arg Gln Arg Lys Lys Ser Lys Met Thr Asp Glu Glu
1               5                   10                  15

(2) INFORMATION FOR SEQ ID NO:34:

(i) SEQUENCE CHARACTERISTICS:
```

-continued

```
            (A) LENGTH: 35 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: CDS
            (B) LOCATION: 4..33

(xi) SEQUENCE DESCRIPTION: SEQ ID NO:34:

ACC ATG GAC TAC AAA GAC GAT GAC GAT AAA TCG AT                          35
    Met Asp Tyr Lys Asp Asp Asp Asp Lys Ser
      1               5                  10

(2) INFORMATION FOR SEQ ID NO:35:

(i) SEQUENCE CHARACTERISTICS:
            (A) LENGTH: 10 amino acids
            (B) TYPE: amino acid
            (D) TOPOLOGY: linear (ii) MOLECULE TYPE: protein (xi) SEQUENCE DESCRIPTION: SEQ ID NO:35:

Met Asp Tyr Lys Asp Asp Asp Asp Lys Ser
  1               5                  10
```

CLONING AND EXPRESSION OF βAPP-C100 RECEPTOR (C100-R)

The present application is a continuation-in-part of application Ser. No. 08/114,555, filed Aug. 30, 1993, now U.S. Pat. No. 5,854,392 and is a continuation-in-part of application Ser. No. 07/938,184, filed Aug. 31, 1992, now abandoned, which is incorporated by reference herein in its entirety.

This invention was made with Government support under Contract #RO1 NS 28965 awarded by the National Institutes of Health. Therefore, the government has certain rights in the invention.

TABLE OF CONTENTS
1. INTRODUCTION
2. BACKGROUND OF THE INVENTION
3. SUMMARY OF THE INVENTION
4. BRIEF DESCRIPTION OF THE FIGURES
5. DETAILED DESCRIPTION OF THE INVENTION
   5.1. THE C100-R CODING SEQUENCE
   5.2. EXPRESSION OF THE C100-R
      5.2.1. EXPRESSION SYSTEMS
      5.2.2. IDENTIFICATION OF TRANSFECTANTS OR TRANSFORMANTS THAT EXPRESS THE C100-R
      5.2.3. RECOVERY OF THE C100-R
   5.3. GENERATION OF ANTIBODIES THAT DEFINE THE C100-R
   5.4. ANTI-SENSE RNA AND RIBOZYMES
   5.5. USES OF THE C100-R, DNA AND ENGINEERED CELL LINES
      5.5.1. SCREENING OF PEPTIDE LIBRARY WITH C100-R PROTEIN OR ENGINEERED CELL LINES
      5.5.2. SCREENING OF ORGANIC COMPOUNDS WITH C100-R PROTEIN OR ENGINEERED CELL LINES
   5.6. USE OF C100-R OR LIGANDS
6. EXAMPLES
   6.1. MATERIAL AND METHODS
      6.1.1. IN VITRO TRANSLATION OF FLAG-βAPP-C100
      6.1.2. CELL CULTURE
      6.1.3. BINDING TO CELLS
      6.1.4. BINDING AUTORADIOGRAPHY
      6.1.5. SCREENING FOR THE C100-R cDNA BY EXPRESSION CLONING
      6.1.6. cDNA CHARACTERIZATION
      6.1.7. IN SITU HYBRIDIZATION USING βAPP-C100 BINDING PROTEIN PROBE
      6.1.8. CLONING OF THE FULL LENGTH RAT APP-4
      6.1.9. PRECIPITATION ASSAYS WITH βAPP-C100 GST FUSION
      6.1.10. IMMUNOPRECIPITATION AND ACTIVATION F C100-R
      6.1.11. ANTIBODIES AND IMMUNOBLOTS
      6.1.12. SYNAPTOSOMAL PLASMA MEMBRANE PREPARATIONS
      6.1.13. RNA BLOT ANALYSIS
      6.1.14. IN SITU HYBRIDIZATION HISTOCHEMISTRY
   6.2. RESULTS
      6.2.1. RADIOLIGAND BINDING
      6.2.2. CLONING AND CHARACTERIZATION OF THE C100-R
      6.2.3. IN VITRO BINDING OF C100-R TO APP, APP-C100 AND ACTIVATED CDC42 AND RAC1
      6.2.4. IN SITU HYBRIDIZATION
7. EXAMPLE: CLONING OF HUMAN C100-R
8. DEPOSIT OF MICROORGANISMS

1. INTRODUCTION

The present invention relates to the cloning of the receptor for the carboxy-terminus of the β-amyloid precursor protein (including the amyloid domain), referred to herein as C100-R, and genetically engineered host cells which express the C100-R. Such engineered cells may be used to evaluate and screen drugs and analogs of the β-amyloid precursor protein (β-APP) which may be used for the diagnosis and/or treatment of Alzheimer's Disease.

2. BACKGROUND OF THE INVENTION

Alzheimer's disease is a neurodegenerative disorder that is the most frequent cause of dementia among aged individuals. The disease is characterized by the accumulation of amyloid-containing plaques in the brain, particularly in the temporal cortex and hippocampus and along the walls of the cerebral vasculature (Roch et al., 1966, Nature 209: 109–110; Terry et al., 1981, Ann. Neurol. 10: 184–192; Glenner G. G., 1983, Arch. Pathol. Lab. Med. 107: 281–282; Katzman, R., 1983, Banbury Report 15, Cold Spring Harbor Lab., Cold Spring, N.Y.).

The amyloid peptide (βA4), found in the plaques of the brain derives from a protein referred to as the amyloid (or beta-amyloid) precursor protein (βAPP). βAPP is normally cleaved within the amyloid domain, which lies near its C-terminus, so that no intact amyloid is produced. An alternative processing pathway results in cleavage of βAPP N-terminal to the amyloid domain, releasing the entire C-terminal from which intact amyloid peptide (βA4) of the amyloid protein precursor may be produced (Glenner and Wong, 1984, Biochem Biophys Res. Commun. 120: 885–890; Masters et al., 1985, Proc. Natl Acad. Sci. USA 82: 4245–4249).

Recent evidence suggests that aberrant processing of β-APP underlies the neuronal degeneration that occurs in Alzheimer's Disease. Neve and coworkers have proposed that the primary βAPP processing event in Alzheimer's Disease is cleavage of the amino terminus of the β/A4 sequence, producing a carboxy-terminal βAPP fragment of 100 amino acid residues (βAPP-C100) which was expressed from a cDNA sequence encoding the carboxyterminal 104 amino acids of βAPP (Yankner et al., 1989, Science 245: 417–420). Hereinafter, this fragment of βAPP will be referred to as βAPP-C100 regardless of whether it is expressed from a cDNA encoding the carboxyterminal 100 or 104 amino acid residues of βAPP. Expression of the βAPP-C100 peptide in primate cells has been shown to lead to production of a protein that aggregates and accumulates into deposit-like structures that result in formation of amyloid-like fibrils (Wolf et al., 1990 EMBO J. 9: 2079–2084). A retroviral recombinant which directs the expression of βAPP-C100 has also been shown to be neurotoxic when transfected into PC-12 cells that have been induced to differentiate by addition of NGF (nerve growth factor). Furthermore, the conditioned media from these transfected cells is toxic to differentiated neuroblastoma and neural cells, and the neurotoxicity can be removed from the medium by immunoabsorption with an antibody to βAPP-C100 suggesting that βAPP-C100 is secreted by transfected cells and is neurotoxic (Yankner et al., 1989, Science 245:

417–420). The toxicity of βAPP-C100 has been further demonstrated by transplantation of cells expressing the peptide into the brains of newborn mice and by creation of mice transgenic for human βAPP-C100 (Neve et al., 1992, Proc. Natl. Acad. Sci. USA 89: 3448–3452). Taken together, evidence indicates a role for βAPP-C100 in development of the neurodegeneration in Alzheimer's disease.

Despite the intense interest in the βAPP-C100 peptide, and its biological role in development of Alzheimer's Disease, very little is known about the proteins, receptors or other tissue elements with which the βAPP-C100 peptide interacts to produce neurotoxicity. Very recently, the high affinity binding of βAPP-C100 to the surface of differentiated PC-12 cells has been demonstrated and correlated with neurotoxicity (Kozlowski et al., 1992, J. of Neuroscience 12: 1679–1687). Both the binding interaction and the occurrence of the neurotoxic response have the same pH dependence. In addition, in PC-12 cells, both the binding and the susceptibility to neurotoxicity develop with similar time courses during NGF-induced differentiation. Furthermore, a single amino-acid change in the βAPP-C100 peptide (Tyr$_{687}$ to Phe), which eliminates its neurotoxic effect, also produces a loss of binding potency. However, the molecular species responsible for binding has not been identified or characterized. The isolation of a cDNA clone coding for the βAPP-C100 binding site or receptor would facilitate studies aimed at determining the biological function of C100-R and its role in development of Alzheimer's Disease. However, this has not, heretofore, been accomplished.

3. SUMMARY OF THE INVENTION

The present invention relates to the C100-R genes and proteins. The neurotoxic effects, resulting from the interaction between βAPP-C100 and the C100-R suggest that therapeutic applications designed to block this particular receptor/ligand interaction may be useful for treatment of Alzheimer's Disease. The DNA sequences disclosed herein may be engineered into expression systems designed for the production of C100-R and/or cell lines which express the C100-R. Such cell lines may be used advantageously for screening and identifying β-APP analogs, including agonists and antagonists. In accordance with another aspect of the invention, the C100-R DNA, antisense oligonucleotide sequences, or antagonists including antibodies to C100-R may be used in the diagnosis and therapy of Alzheimer's Disease. Transgenic animals containing the C100-R transgene may be used as animal models for the evaluation of β-APP-C100 analogs in vivo.

The invention is based, in part, on the discovery, identification and cloning of a βAPP-C100 binding site that is expressed in neuronally derived cells. The cDNA represents an ~11 kb mRNA with a 1632 base pair (bp) open reading frame encoding a novel 61 kilodalton (kDa) putative serine/threonine kinase.

Immunoprecipitated C100-R, expressed recombinantly in COS-7 cells, phosphorylates a myelin basic protein substrate in the presence of the activated p21 proteins Rac1 and Cdc42. These two members of the Ras-related Rho subfamily of small GTPases regulate cytoskeletal organization; and in particular, Rac1 is a key component of the machinery controlling axonal outgrowth. Therefore, the interaction of the C-terminal domain of APP with C100-R is likely to be involved in neuronal signal transduction mediated by Rac1 and Cdc42.

Disruption of this signal transduction pathway may play a part in the disassembly of the cytoskeleton that occurs in Alzheimer's disease. Therefore, the cDNA clone encoding the C100-R may be of therapeutic value for the diagnoses and design of drugs for treatment of Alzheimer's Disease.

4. BRIEF DESCRIPTION OF THE FIGURES

FIG. 1.—Representative curve showing the inhibition of $^{35}$S-βAPP-C100 binding to (A) NGF-treated (5d) PC12 cells and (B) SK-N-MC cells, by βAPP-C100.

Figure 2A:
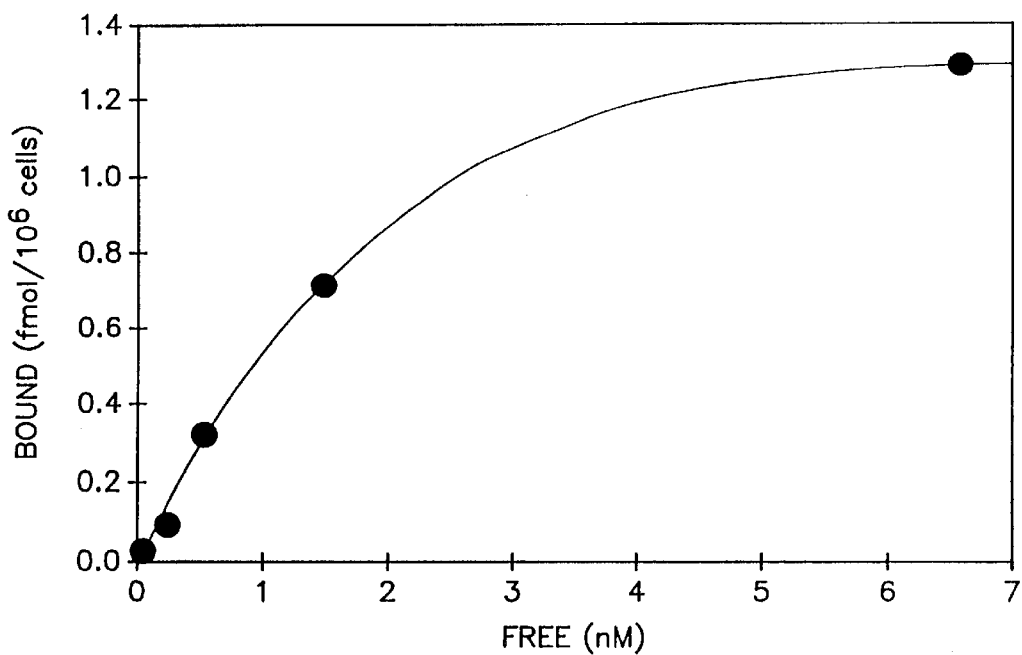
Figure 2B:
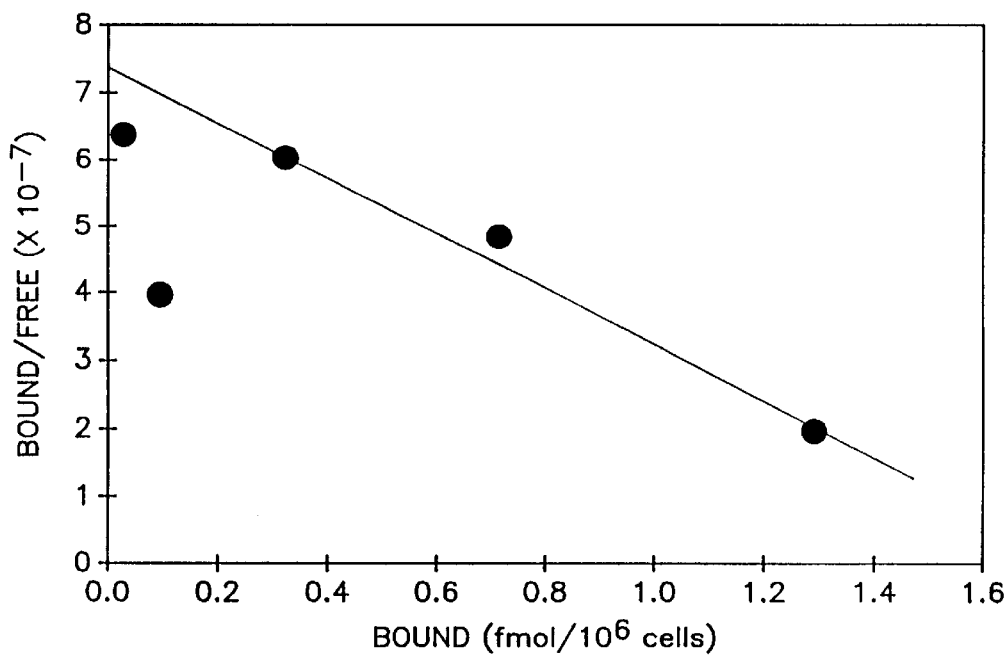

FIGS. 2A–2B.—Representative saturation isotherm (top panel) and Scatchard plot (bottom panel) of $^{35}$S-βAPP-C100 binding to NGF-treated (6d) PC12 cells. The lines were computer generated and represent the best interpretation of the data.

Figure 3:
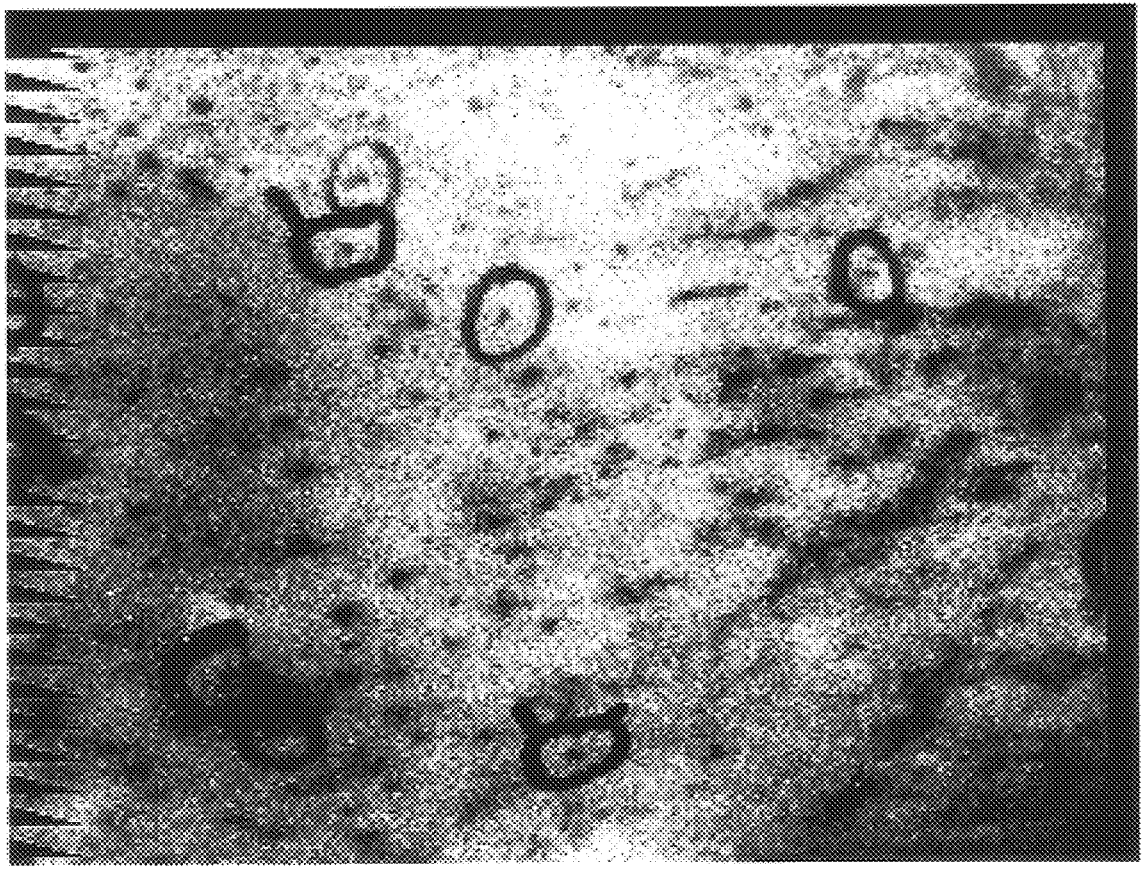

FIG. 3.—Screening of λgt11 rat cDNA libraries using the Direct Binding method.

FIGS. 4A–C.—Nucleotide Sequence of cDNA insert of rat C100-R clone, AB1R (SEQ ID NOS:1 and 2). Underlined region represents SER/THR Kinase "signature" or conserved catalytic core sequence.

FIGS. 5A–E.—Sequence homology between C100-R and (A) "B" type calcium channels (SEQ ID NOS:3 and 4), (B) calreticulin (SEQ ID NOS:5–8), and (C) Ryanodine calcium channel (SEQ ID NOS:9–14).

Figure 6:
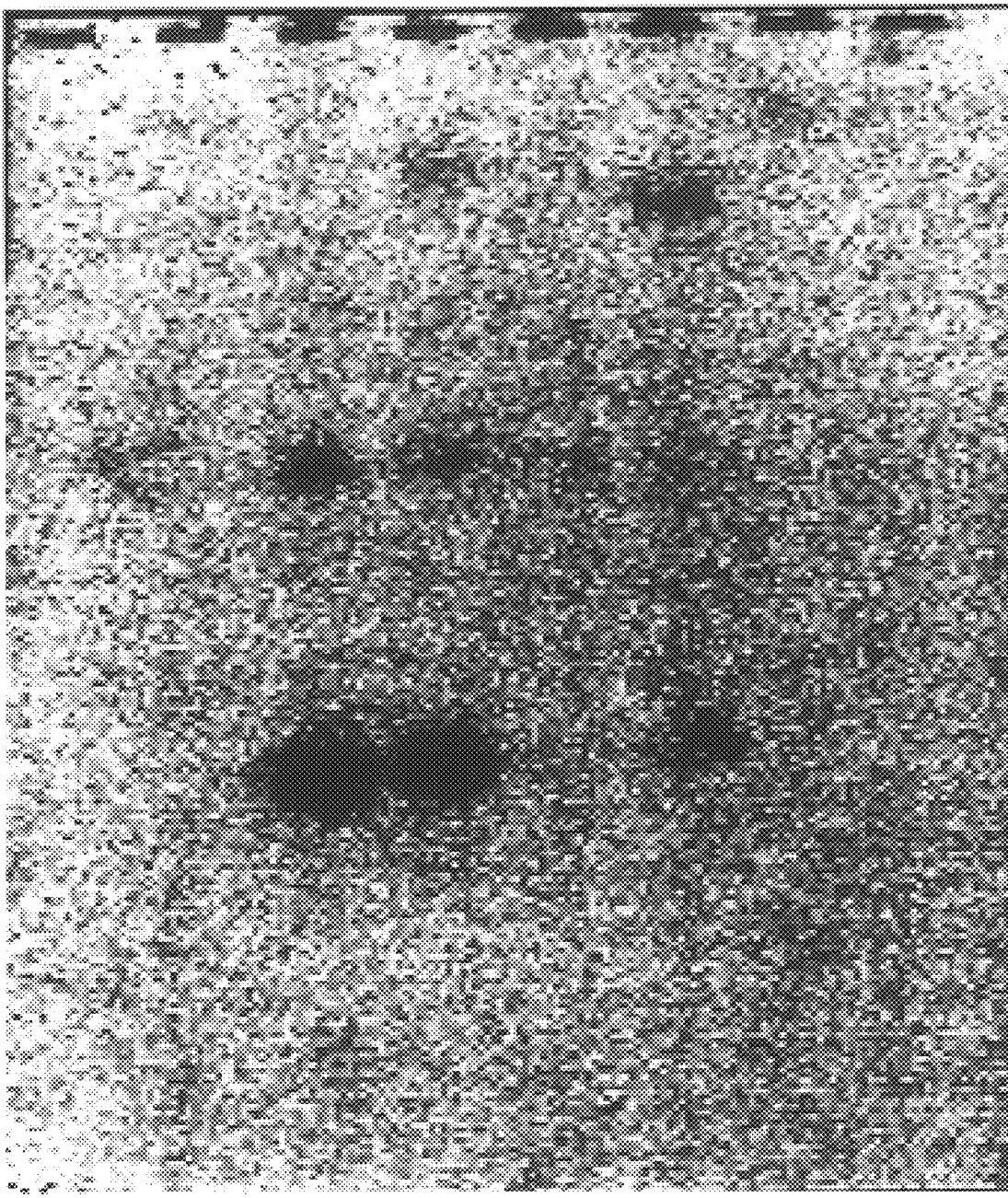

FIG. 6.—Southern blot analysis of the AB1R cDNA. Lane A is EcoRI digested human DNA. Lane B is EcoRI digested mouse DNA. Lane C is HindIII digested mouse DNA. Lane D is HindIII digested human DNA. λ/HindIII markers were run to establish molecular weights.

Figure 7A:
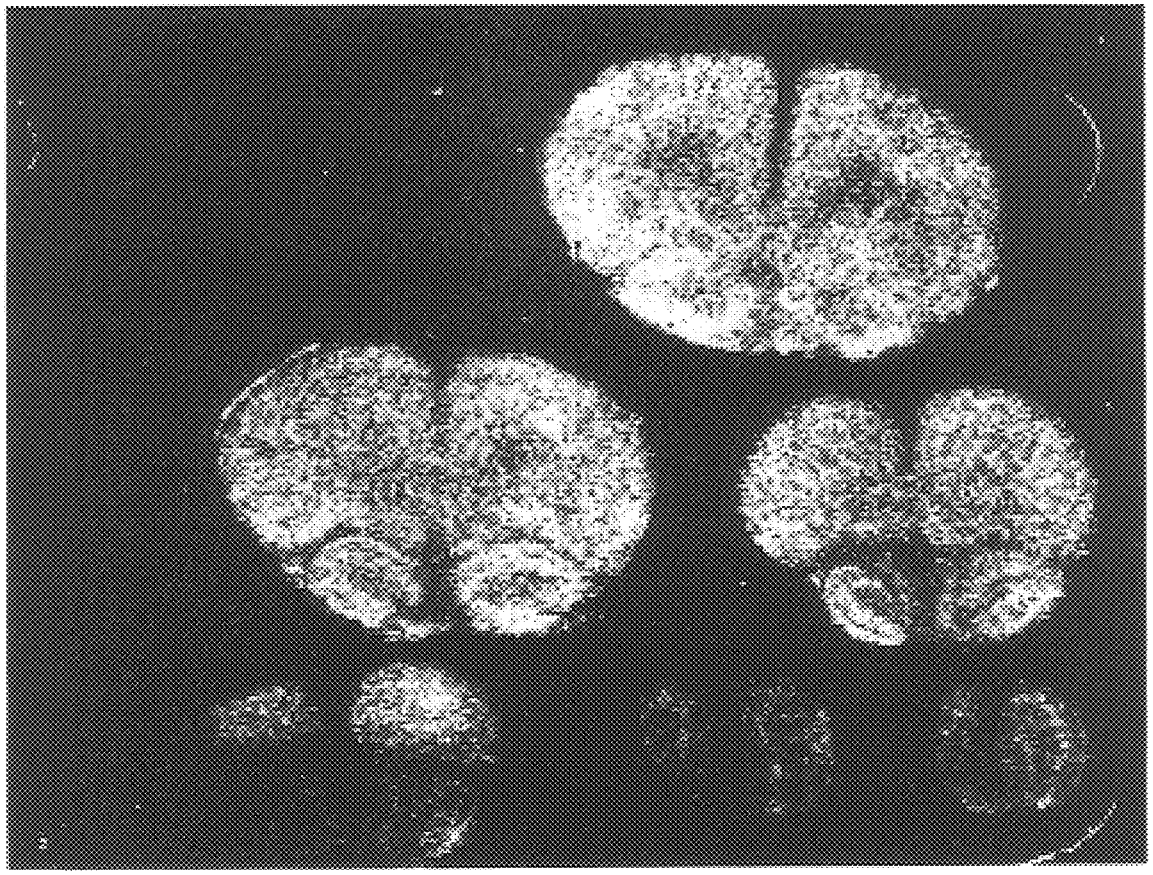
Figure 7B:
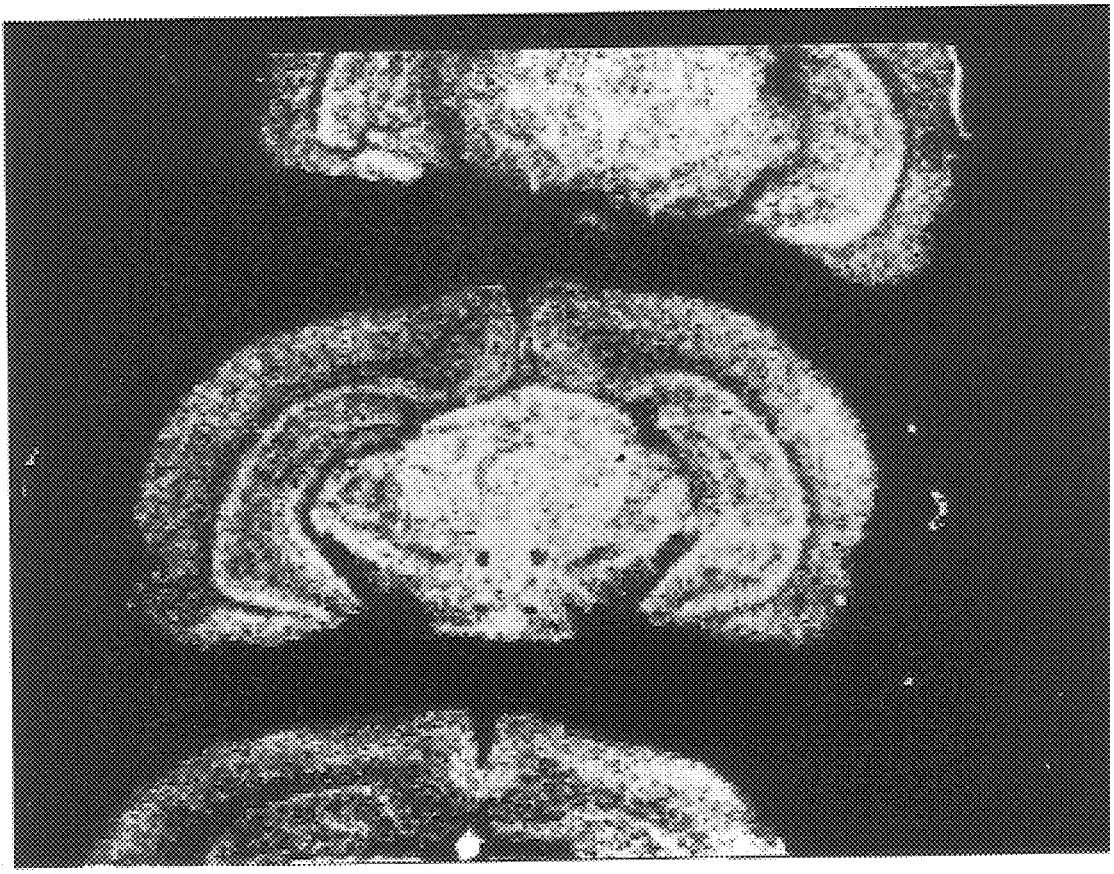

FIGS. 7 A and B.—Representative autoradiographs of specific binding to rat brain sections at (FIG. 7A) anterior and (FIG. 7B) middle to posterior levels. The images were digitized and enhanced so that areas with higher levels of binding are lighter. Note that certain areas of the olfactory tubercle (lower part of sections in (A) and hippocampus (mid-lateral part of section in (B) stand out against the relatively uniform labelling of the rest of the grey matter.

Figure 8A:
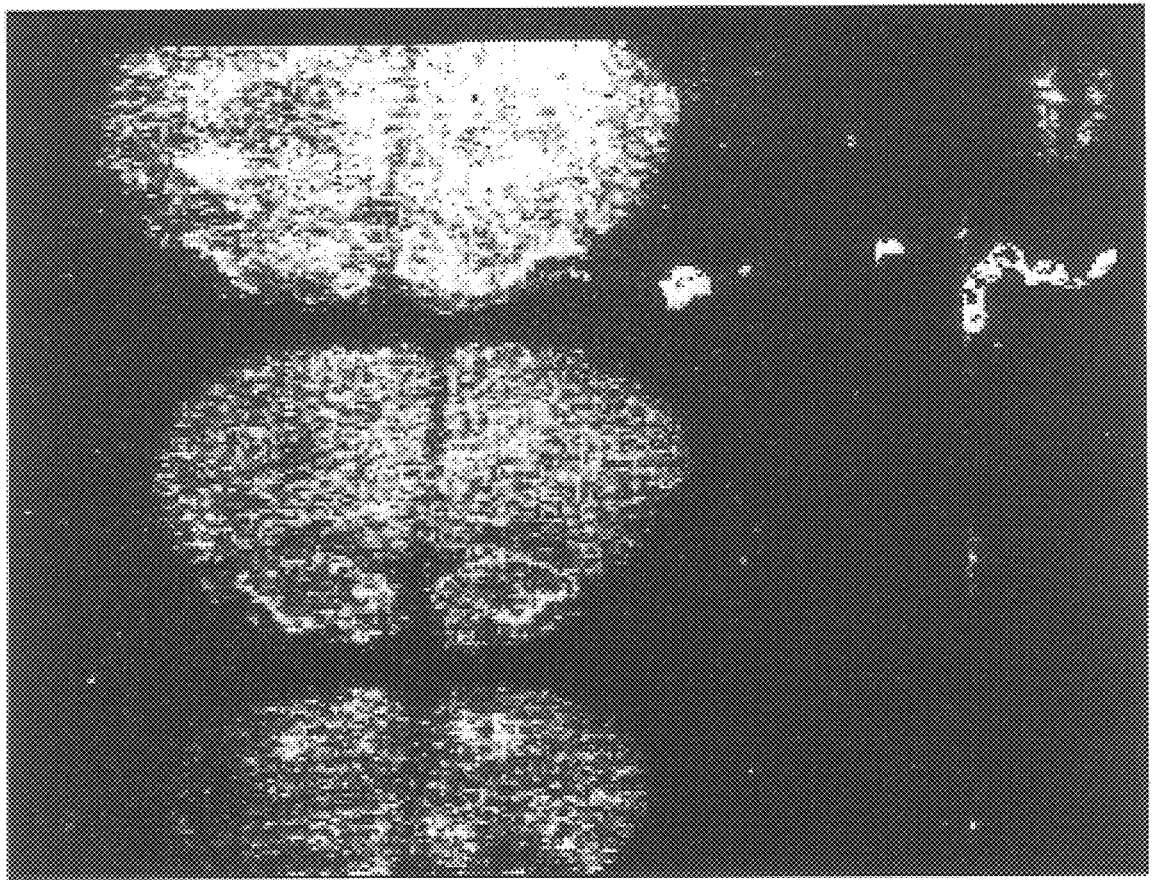
Figure 8B:
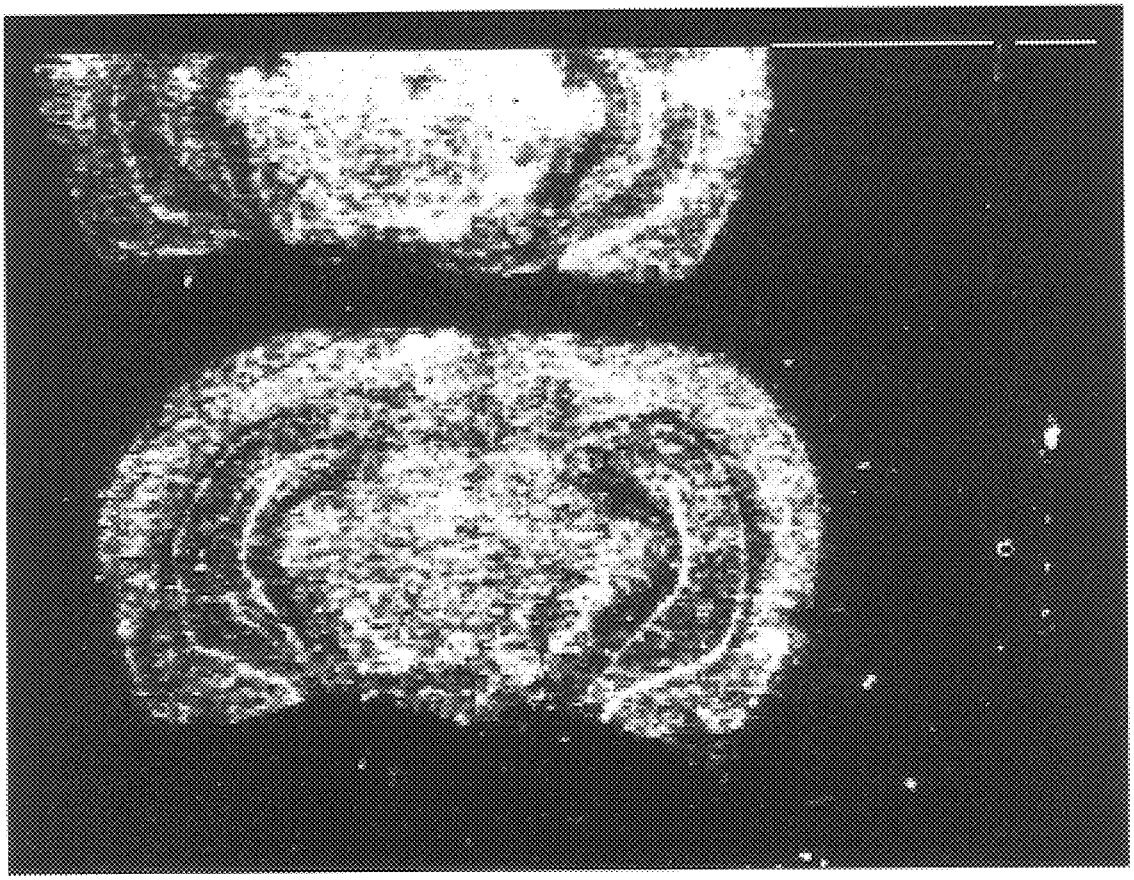

FIGS. 8A–B.—Representative autoradiographs of the in situ hybridization of the pAB1R antisense probe. section locations and method of reproduction are as in FIGS. 7A–7B. Note the areas of high labelling (lightest areas) in the olfactory tubercle and hippocampus in agreement with the results from the binding autoradiography (FIGS. 7A–7B).

FIG. 9.—Nucleotide sequence of cDNA insert of rat C100-R clone, AB2R (SEQ ID NO: 15). The EcoRI fragment from nucleotide 31 through nucleotide 409 was used to screen a human hippocampal cDNA library.

FIG. 10.—Nucleotide sequence of rat C100-R clone (SEQ ID NOS:16 and 17). The disclosed sequence is the result of cloning and sequencing of a number of overlapping rat cDNA clones. The * above nucleotide 686 represents the junction with the rat C100-R nucleotide sequence depicted in FIG. 4 (nucleotide 40).

Figure 11A:
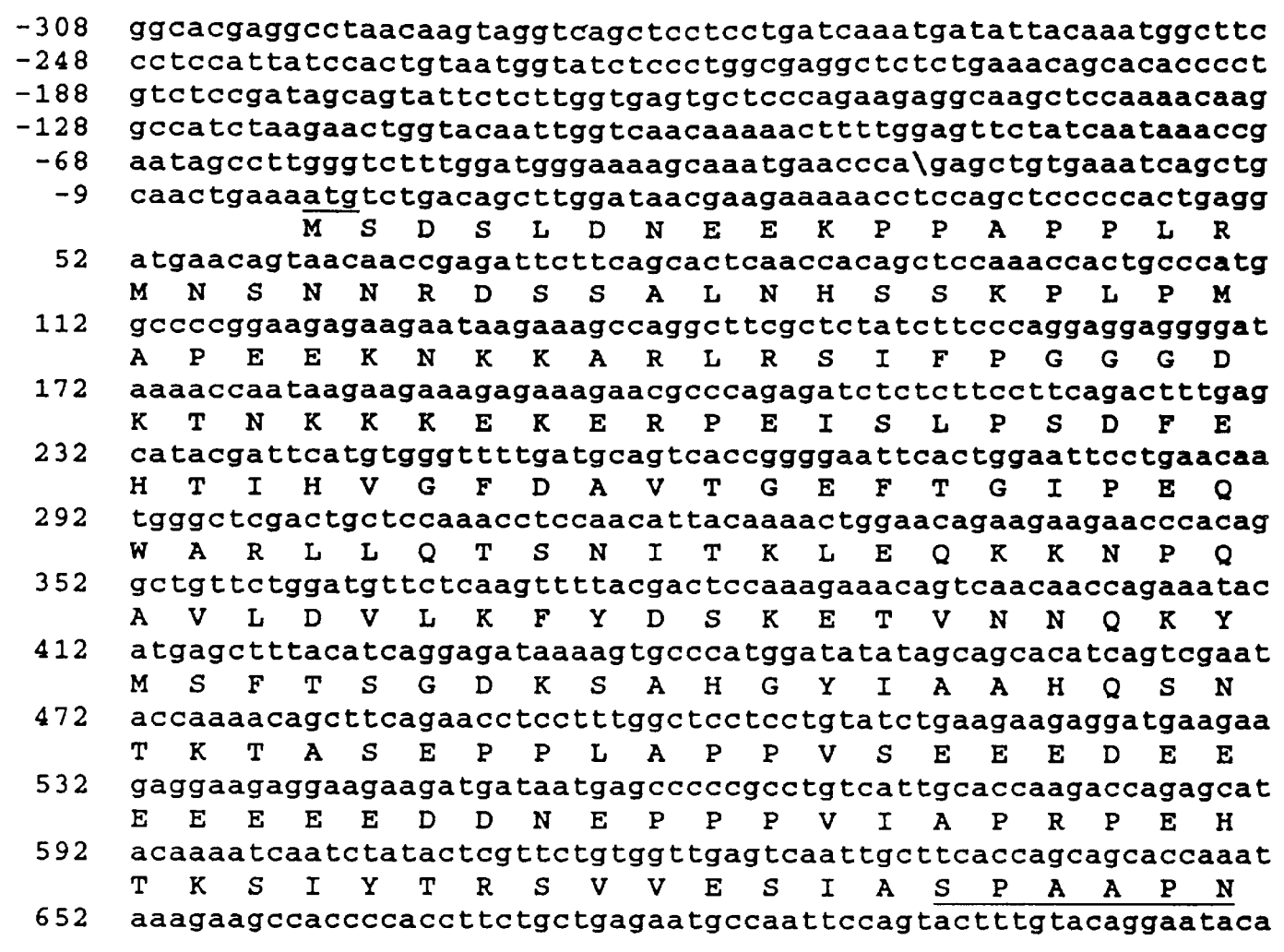

FIGS. 11.A–C—Nucleotide sequence of the cDNA encoding the complete C100-R (SEQ ID NOS:18 and 19). Alternative splicing of the transcript occurs at position −27, as indicated by a backslash; the sequence of only one of the spliced forms is shown. Peptide sequences that were used to make antisera are underlined. The 3'UTR is not shown in its entirety.

FIGS. 12A–B.—Amino acid sequence homology between C100-R (SEQ ID NO: 29), Pak1 (SEQ ID NO: 30) and STE20 (SEQ ID NO: 31). Note the strong homology in the C-terminal kinase domain. The Cdc42/Rac1-binding domain near the N-terminus is boxed. Additional members of the Pak family, not shown in this figure, have been cloned.

Figure 13:
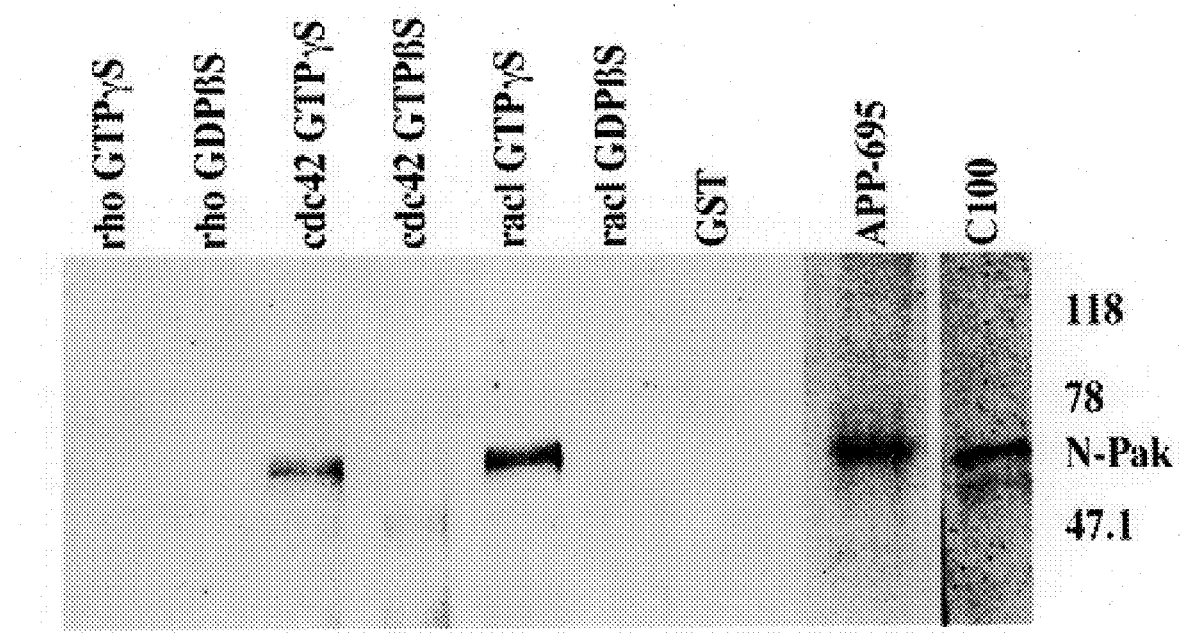

FIG. 13.—Co-immunoprecipitation of radiolabelled C100-R by APP-695, APP-C100, and GTP-activated p21 GST fusion proteins. The 61-kDa C100-R in vitro translation product is indicated. Note that it is absent in the control GST lane. It also fails to bind to GST-Rho, whether GDP-or GTP-bound, and to GDP-bound GST-Cdc42 and GST-Rac1.

Figure 14A:
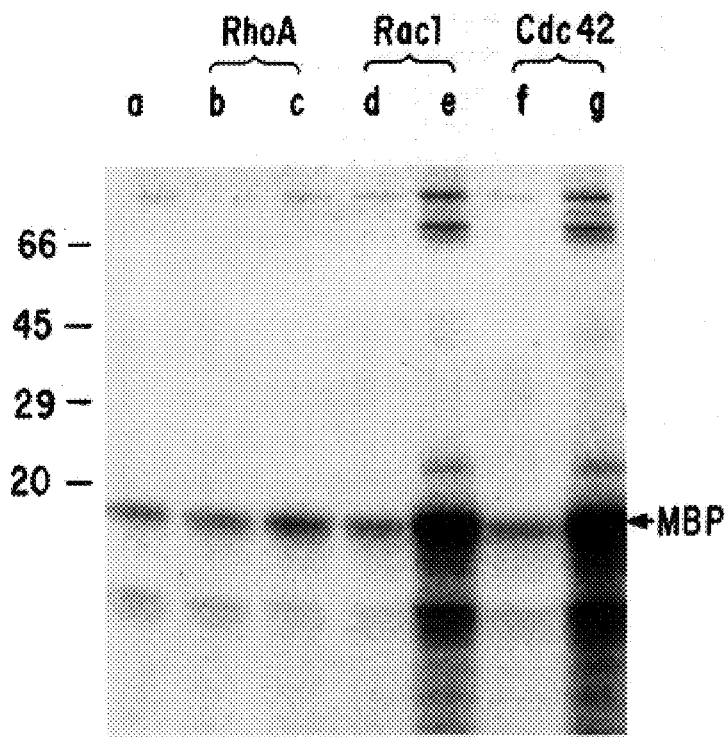

FIG. 14A.—Activation of C100-R by GTP-bound Cdc42 and Rac1. Immunoprecipitated myc-C100-R fusion protein was incubated for 20 min at 25° C. with GST(a), GST-RhoA (b,c) GST-Rac1 (d,e) or GST-Cdc42(f,g) which were bound to either GDPβS (b,d,f) or GTPγS (c,e,g). The precipitates were washed and the bound C100-R was assayed for its ability to phosphorylate myelin basic protein (MBP). Molecular mass standards are shown on the left (kDa).

Figure 14B:
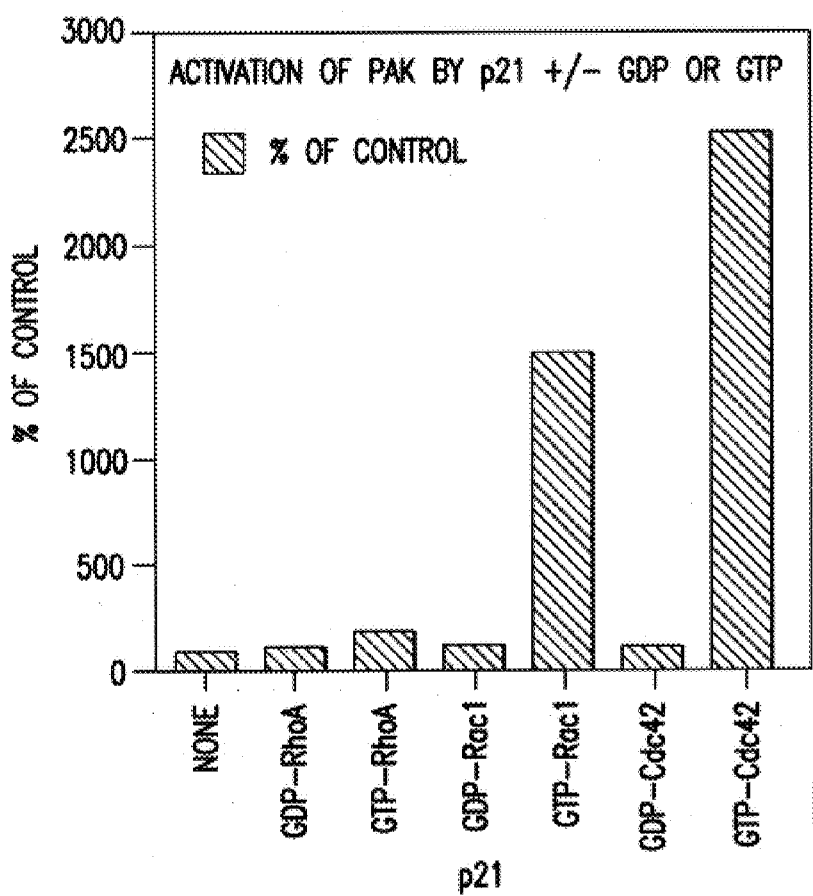

FIG. 14B. Quantitation of the amount of MBP phosphoprotein following MBP incubation with the immunoprecipitated myc-C100-R and the indicated GST-p21 fusion proteins.

Figure 15A:
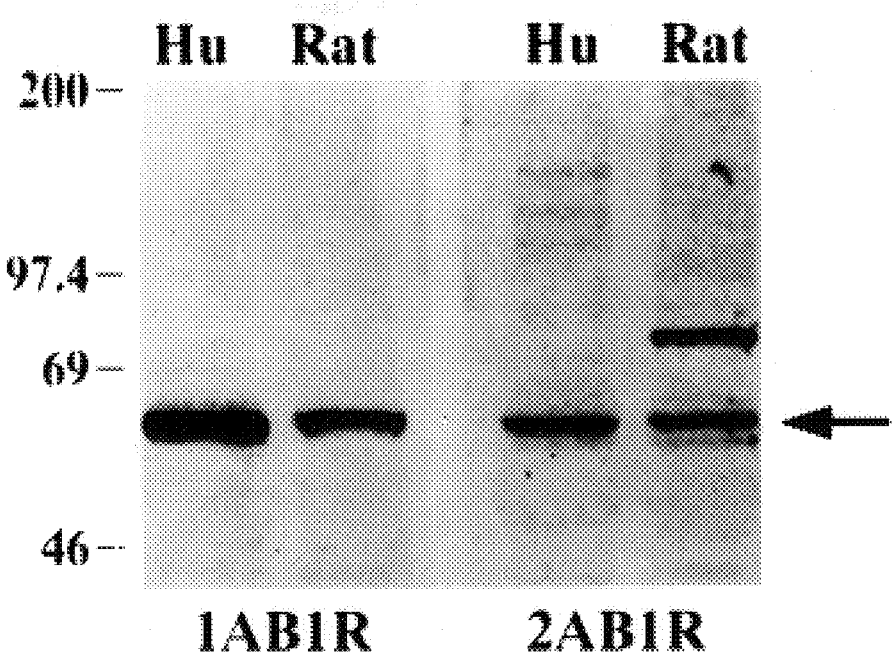

FIG. 15A.—Immunoblot analyses of C100-R in human and rat brain homogenates. As indicated by the arrows, two independent immunoaffinity-purified antibodies (1AB1R and 2AB1R) generated against distinct peptides within the C100-R sequence immunodetected a 61 kDa band in total human (Hu) and rat brain homogenates. The higher molecular weight band may represent the product of an alternatively spliced C100-R mRNA, or may represent a closely-related protein with which the antibody cross-reacts.

Figure 15B:
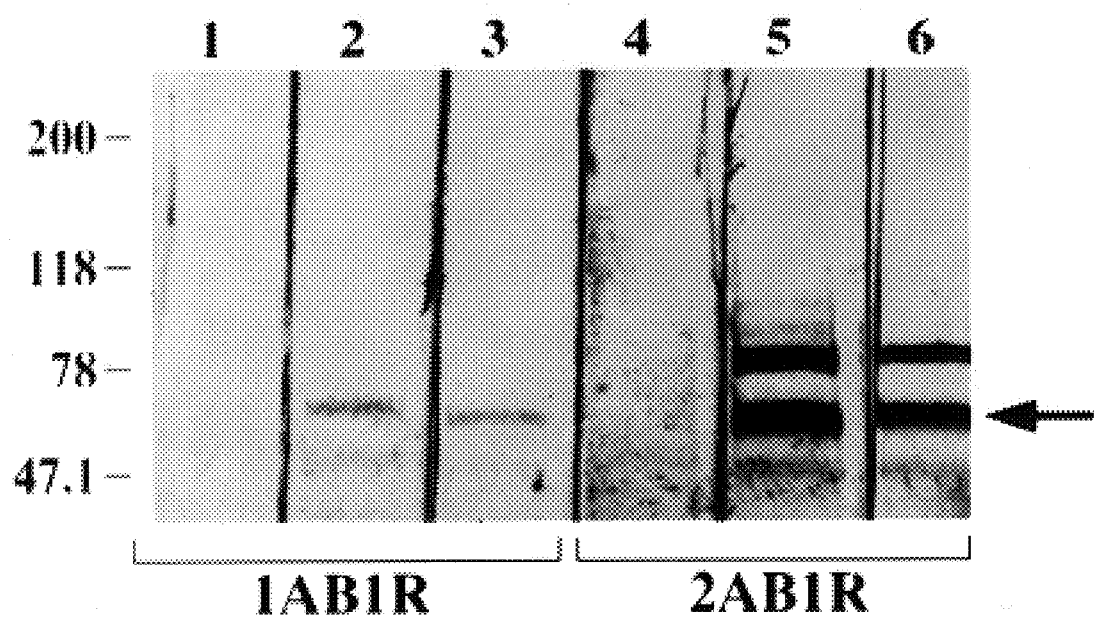

FIG. 15B. Immunoabsorption experiments demonstrate the specificity of the two antibodies in immunoblots of total rat brain homogenates. Lane 1, 1AB1R antibody preabsorbed with the 1AB1R peptide; lane 2, 1AB1R antibody preabsorbed with the 2AB1R peptide; lane 3, 1AB1R antibody without preabsorption; lane 4, 2AB1R antibody preabsorbed with the 2AB1R antibody without preabsorption.

Figure 15C:
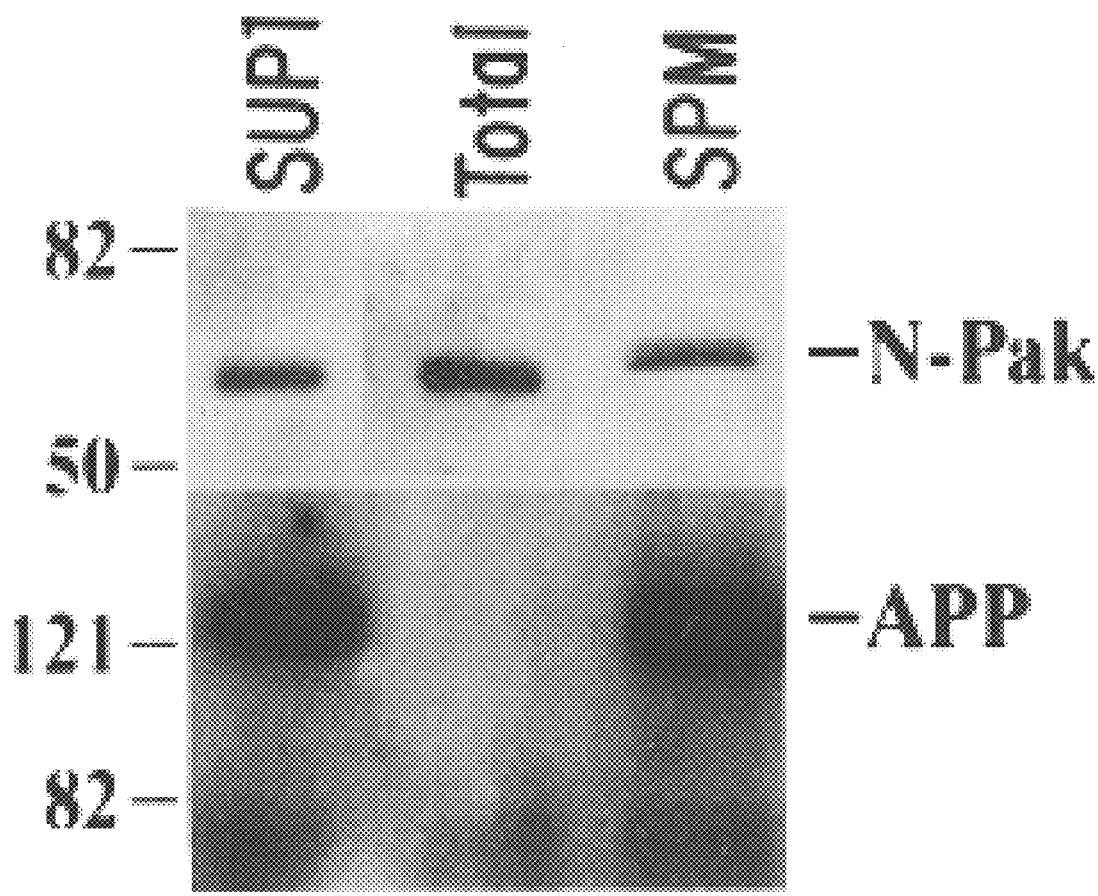

FIG. 15C.—Fractions of human fetal brain were immunoblotted with 1AB1R (top) or the anti-APP antibody S369 (bottom). Note co-localization of C-100-R and APP immunoreactivity in the synaptosomal plasma membrane fraction. "Sup 1" refers to the supernatant retrieved after the first low-speed spin following homogenation of the brain tissue.

Figure 16A:
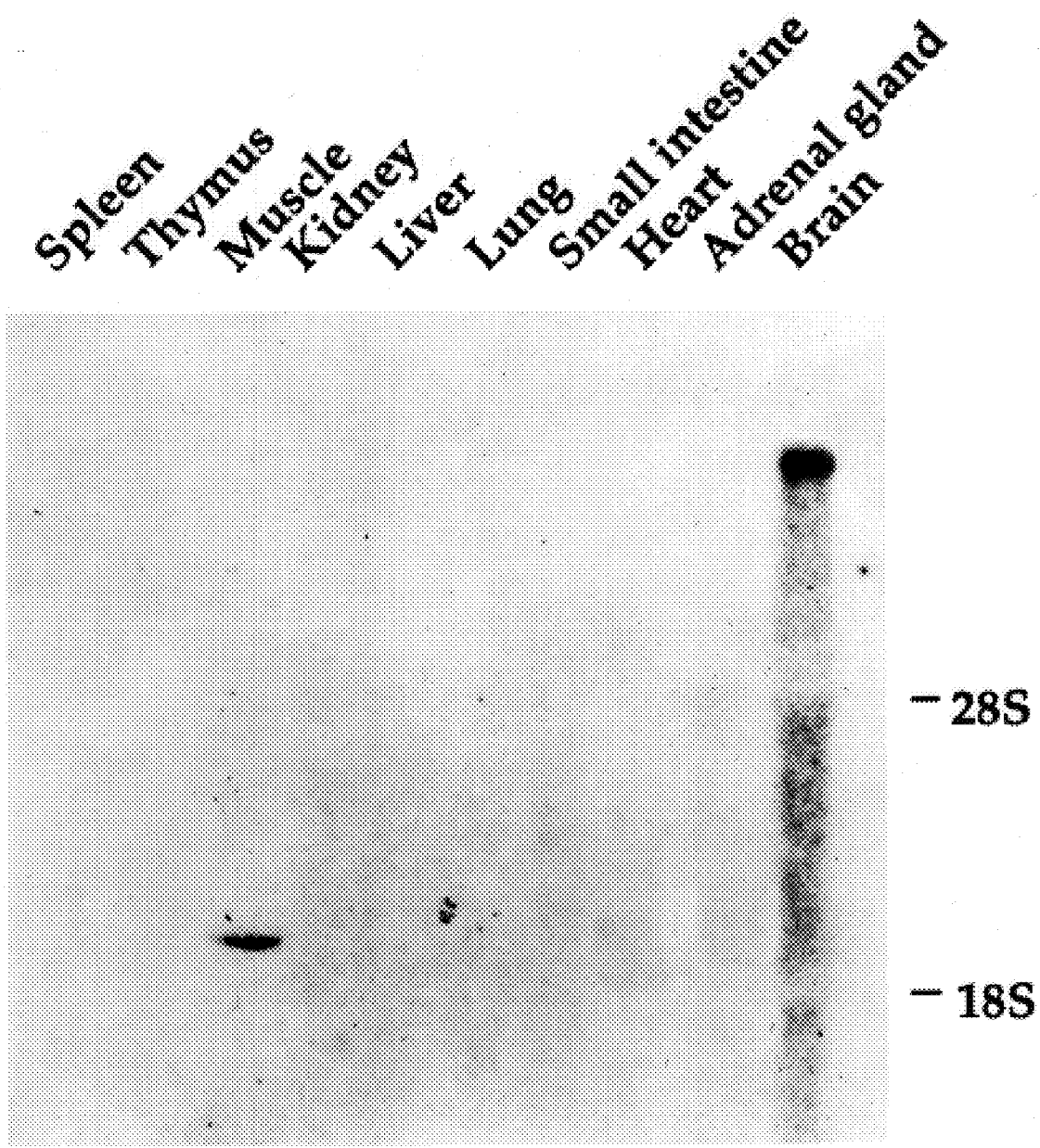

FIG. 16A.—RNA blot analyses of C100-R gene expression. The C100-R cDNA was used to probe an RNA blot containing RNA from a range of human fetal (20–22 week) tissues. 20 ug of total RNA was loaded in each lane.

Figure 16B:
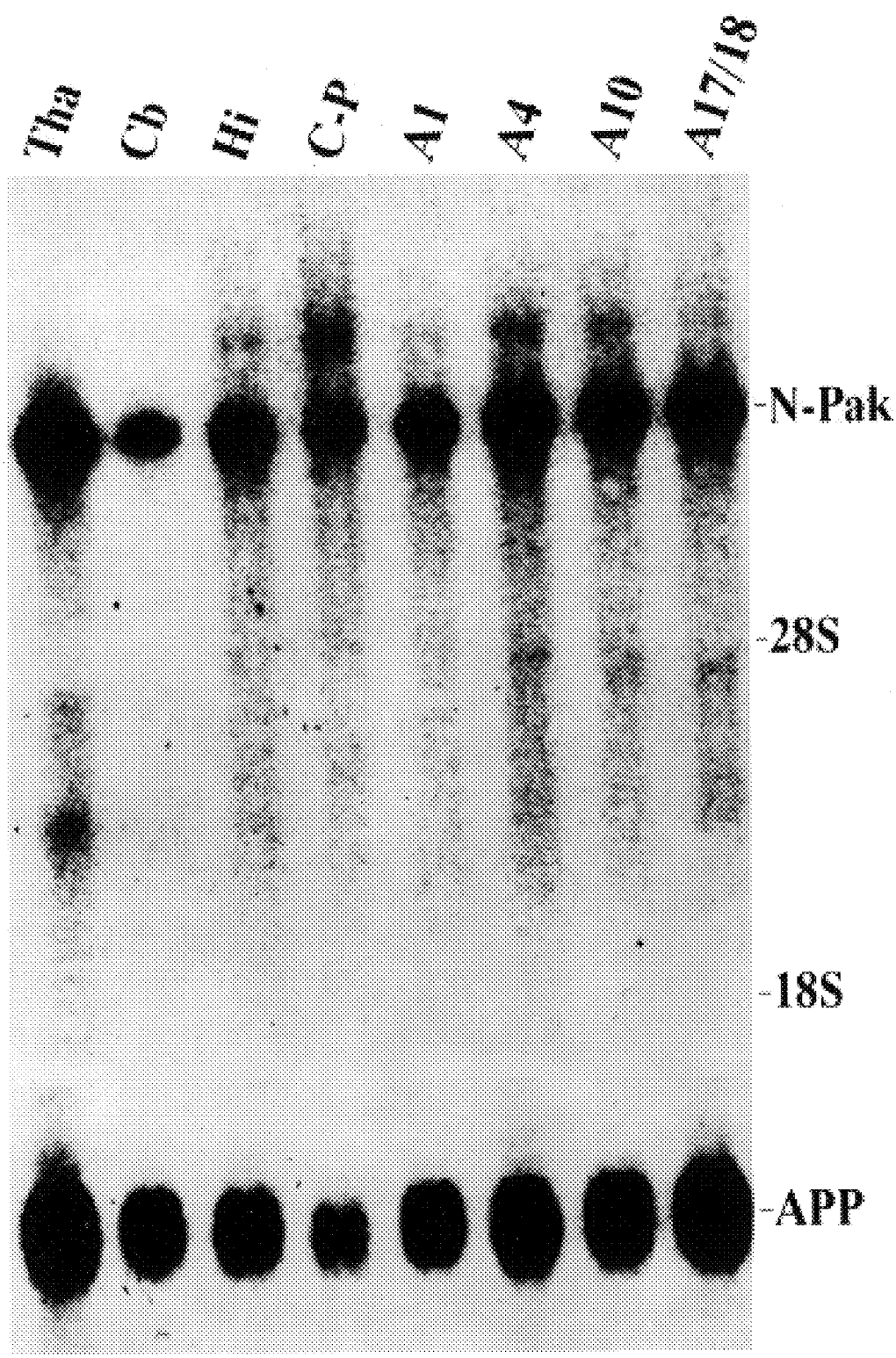

FIG. 16B.—Analysis of C100-R mRNA expression in subregions of human fetal (20 week) brain. Tha, thalamus; Cb, cerebellum; Hi, hippocampus; C-P, caudate-putamen; A1, primary sensory cortex; A4, primary motor cortex; A10, frontal cortex; A17/18, visual cortex.

Figure 16C:

FIG. 16C.—Expression of C100 -R mRNA expression in human and rat nervous system tissues.

FIGS. 17A–H.—In situ hybridization analysis of C-100-R gene expression in the rat brain.

FIGS. 18A–C.—Nucleotide sequence of cDNA inserts of human C100-R (SEQ ID NOS:26–28) clone. The nucleotide designated M is either A or C and the nucleotide designated K is either T or G.

FIG. 19A.—Sequence homology between human C100-R and rat C100-R (SEQ ID NOS:20 and 21). Human #4.t3 sequence is aligned with the rat C100-R sequence depicted in FIG. 9 starting at nucleotide 544.

FIG. 19B.—Sequence homology between human C100-R and rat C100-R (SEQ ID NOS: 22 and 23). Human clone HABIR #1#4 is aligned with the rat C100-R sequence depicted in FIG. 4, starting at nucleotide 182.

FIG. 19C.—Sequence homology between human C100-R and rat C100-R (SEQ ID NOS: 24 and 25). Human clone #1#1T3 is aligned with the rat C100-R sequence depicted in FIG. 4 starting at nucleotide 1868.

5. DETAILED DESCRIPTION OF THE INVENTION

The present invention relates to the cloning and expression of the C100-R. The C100-R was initially characterized as a binding site present in neuronally derived cells, that bound specifically to the amyloid peptide βAPP-C100. Expression of the βAPP-C100 amyloid peptide has been shown in animal models to correlate with the specific type of neuronal degeneration that occurs in Alzheimer's Disease. The C100-R produced herein may be used to evaluate and screen drugs and analogs of β-APP that may be used in the diagnosis and/or treatment of Alzheimer's Disease.

5.1. The C100-R Coding Sequence

The initial rat C100-R cDNA clone, designated λAB1R, was obtained by screening a λgt11 rat brain expression library with β-APP-C100 ligand labeled with $^{35}$S-methionine or a peptide epitope "flag" sequence as described in Section 6, infra. The initial clone, designated pABIR-rat, was found to contain a 1970 bp insert comprised of the nucleotide coding sequence and deduced amino acid sequence depicted in FIGS. 4A–4C. A corresponding cDNA clone has been deposited with the ATCC and assigned numbers described in Section 8, infra. Sequence analysis reveals that the clone encompasses the carboxy-terminal section of the gene and contains 1395 base pairs of coding sequence and 575 bp of 3' untranslated sequence (FIGS. 4A–4C).

As indicated by the detection of an 11 Kb C100-R mRNA on Northern blots, the nucleotide sequence depicted in FIGS. 4A–4C is only a partial representation of the C100-R gene. Full length rat C100-R cDNA sequence may be obtained using a variety of different methods.

For example, in a specific embodiment of the invention described herein, RNA prepared from rat brain and a primer specific for the most 5' end of the ABIR cDNA insert, was utilized for first strand synthesis in a reverse transcriptase reaction. Following second strand synthesis, the cDNA was inserted into the bacterial Bluescript plasmid (Stratagene). Additional rat C100-R cDNA clones were isolated and sequenced (FIG. 9 and FIG. 10). The new sequences overlap with those rat sequences shown in FIG. 4 and extend the coding region towards the amino-terminal end of the C100-R protein (FIG. 10). The sequence disclosed in FIG. 9 diverges upstream of nucleotide 106 from the rat sequence shown in FIG. 10, indicating that alternatively spliced mRNAs may exist for the C100-R clone.

The partial C100-R cDNA clones were used to reprobe rat brain cDNA libraries, and numerous cDNA clones overlapping with the original clone and extending it at the 5' end were isolated. At least three of these cDNAs contained a full-length coding sequence. Sequence analysis of these clones revealed a 1632 bp open reading frame (FIGS. 11A–11C) encoding a 544 amino acid protein with a calculated molecular mass of 60.7 kDa. A portion of the sequence of the cDNA was found to be homologous to that coding for the serine/theonine kinase domain of the yeast STE20 protein (Leberer et al., 1992, EMBO J. 11: 4815–4824; Ramer and Davis, 1993, Proc. Natl. Acad. Sci. USA 90: 452–456), with 67% identity over an interval of 683 bp at the 3' end of each coding sequence. A search of the protein database revealed that the putative neural APP binding protein (C100-R) was closely related to rat p65$^{PAK}$ (Pak1; Manser et al., 1994) and yeast STE20 proteins (FIGS. 12A–12B) with highest homology in the serine/theonine kinase domain (70% between C100-R and STE20; 90% between C100-R and p65$^{PAK}$). In addition, these three kinases shared, in their N-terminal domains, a peptide motif representing the Cdc42/Rac1-binding domain of Pak1 (FIG. 12A). The overall identity between C100-R and p65$^{PAK}$ protein sequences was 83%. P65$^{PAK}$ is a serine/theonine protein kinase that is activated by the Rho family p21 proteins Cdc42 and Rac1. The very close similarity between C100-R and p$_{65}$$^{PAK}$ indicates an analogous function for C100-R. At least four spliced forms of C100-R mRNA were identified. All four spliced forms diverged within the 5' UTR, at bp −27 (FIG. 10).

The invention also relates to C100-R genes isolated from other species, including humans, in which C100-R activity exists. Members of the C100-R family are defined herein as those receptors that bind βAPP-C100 or fragments of the peptide. Such receptors may demonstrate about 80% homology at the nucleotide level, and even 90% homology at the amino acid level in substantial stretches of DNA sequence. Therefore, in addition to the C100-R nucleotide sequence that encodes the amino acid sequence of the C100-R protein shown in FIGS. 10 and 11, nucleotide sequences capable of hybridizing to such C100-R sequences under highly or less highly stringent hybridization conditions are well within the scope of the invention. High stringent hybridization conditions may be defined as hybridization to filter-bound DNA in 0.5M NaHPO$_4$, 7% sodium dodesyl sulfate (SDS), 1 mm EDTA at 65° C., followed by washing in 0.1× SSC/0.1% SDS at 68° C. (Ausubel, F. M. et al., eds, 1989 Current Protocols in Molecular Biology, Vol. I, Green Publishing Associates, Inc., and John Wiley & Sons, Inc., New York at p. 2.10.3). Less highly stringent conditions, such as moderately stringent conditions, may be defined as hybridization carried out as described above, followed by washing in 0.2× SSC/0.1% SDS at 42° C. (Ausubel et al., 1989, supra).

To identify C100-R genes isolated from other species a bacteriophage cDNA library may be screened, under moderately stringent hybridization conditions, using a radioactively labeled fragment of the rat C100-R clone. Alternatively, the rat C100-R sequence can be used to design degenerate or fully degenerate oligonucleotide probes which can be used as PCR probes or to screen bacteriophage cDNA libraries. A polymerase chain reaction (PCR) based strategy may be used to clone human C100-R. Two pools of degenerate oligonucleotides, corresponding to conserved motifs between the rat C100-R and the serine/theonine p65$^{PAK}$/STE20 family of kinases, may be designed to serve as primers in a PCR reaction. The template for the reaction is cDNA obtained by reverse transcription of mRNA prepared from cell lines or tissue known to express human APP-R. The PCR product may be subcloned and sequenced to insure that the amplified sequences represent the C100-R sequences. The PCR fragment may then be used to isolate a full length C100-R cDNA clone by radioactively labeling the amplified fragment and screening a bacteriophage cDNA library. Alternatively, the labeled fragment may be used to screen a genomic library. For a review of cloning strategies which may be used, see e.g., Maniatis, 1989, Molecular Cloning, A Laboratory Manual, Cold Springs Harbor Press, N.Y.; and Ausubel et al., 1989, Current Protocols in Molecular Biology, (Green Publishing Associates and Wiley Interscience, N.Y.)

A cDNA library may also be constructed in a mammalian expression vector such as pcDNA1, that contains SV40 origin of replication sequences which permit high copy number expression of plasmids when transferred into COS cells. The expression of C100-R on the surface of transfected COS cells may be detected in a number of ways, including the use of a labeled ligand such as βAPP-C100 or a βAPP-C100 agonist labeled with a radiolabel, fluorescent label or an enzyme. Cells expressing the human C100-R may be enriched by subjecting transfected cells to a FACS (fluorescent activated cell sorter) sort.

In a specific embodiment described herein, an adult hippocampal cDNA library was screened with a labeled nucleotide fragment from the rat C100-R clone. The large EcoRI fragment, extending from nucleotide 31 through nucleotide 409 of the AB2R rat clone (FIG. 9) was used to probe the human cDNA library. The library was screened using the following hybridization and washing conditions: hybridization in 6×55 C at 68° C. followed by washingt at 0.1×55 C at 65° C. Several clones were obtained and the cDNA inserts were sequenced. Human C100-R sequences are shown in FIG. 18, and regions of homology between the rat and human C100-R sequences are shown in FIGS. 19A–19C.

Any of the methods described above for isolation of full length rat C100-R clones may be used equally well for isolation of full length human C100-R clones. For instance, probes specific for the most 5' sequence of the human clone may be used to rescreen the human cDNA library. With each successful round of sequencing new 5' probes may be designed and used to reprobe libraries until the entire sequence has been obtained.

In accordance with the invention, nucleotide sequences which encode C100-R, fragments, fusion proteins or functional equivalents thereof, may be used to generate recombinant DNA molecules that direct the expression of the C100-R, or a functionally active peptide, fusion protein or functional equivalent thereof, in appropriate host cells. Alternatively, nucleotide sequences which hybridize to portions of the C100-R sequence may also be used in nucleic acid hybridization assays, Southern and Northern blot analyses, etc.

Due to the degeneracy of the genetic code, other DNA sequences which encode substantially the C100-R amino acid sequence, e.g., such as the rat sequence depicted in FIGS. 4A–4C or a functional equivalent may be used in the practice of the present invention for the cloning and expression of the C100-R.

Such DNA sequences also include those which are capable of hybridizing to the rat or human C100-R sequence and encode a naturally occurring C100-R in another species or cell type. The stringency conditions may be adjusted in a number of ways. For example, when performing polymerase chain reactions (PCR), the temperature at which annealing of primers to template takes place or the concentration of MgCl$_2$ in the reaction buffer may be adjusted. When using radioactively labeled DNA fragments or oligonucleotides to probe filters, the stringency may be adjusted by changes in the ionic strength of the wash solutions or by careful control of the temperature at which the filter washes are carried out.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within the C100-R sequence, which result in a silent change thus producing a functionally equivalent C100-R. Such amino acid substitutions may be made on the basis of similarity in polarity, charge, solubility, hydrophobicity, hydrophilicity, and/or the amphipatic nature of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. As used herein, a functionally equivalent C100-R refers to a receptor which binds to β-APP-C100 or fragments, but not necessarily with the same binding affinity of its counterpart native C100-R.

The DNA sequences of the invention may be engineered in order to alter the C100-R coding sequence for a variety of ends including but not limited to alterations which modify processing and expression of the gene product. For example, mutations may be introduced using techniques which are well known in the art, e.g. site-directed mutagenesis, to insert new restriction sites, to alter glycosylation patterns, phosphorylation, etc. For example, in certain expression systems such as yeast, host cells may over glycosylate the gene product. When using such expression systems it may be preferable to alter the C100-R coding sequence to eliminate any N-linked glycosylation site. In another embodiment of the invention, the C100-R or a modified C100-R sequence may be ligated to a heterologous sequence to encode a fusion protein. The fusion protein may be engineered to contain a cleavage site located between the C100-R sequence and the heterologous protein sequence, so that the C100-R can be cleaved away from the heterologous moiety.

In a specific embodiment described herein the C100-R coding sequence was ligated in frame to the N-terminal myc epitope [EQKLISEEDL] in expression vector pMT3 (Kaufman R. J. et al., 1987, EMBO J. 6: 187–193). Following transfection of the recombinant expression vector into mammalian cells, expression of a C-100R/myc fusion protein was detected in immunoprecipitation assays utilizing anti-myc antibodies.

In an alternate embodiment of the invention, the coding sequence of C100-R could be synthesized in whole or in part, using chemical methods well known in the art. See, for example, Caruthers, et al., 1980, Nuc. Acids Res. Symp. Ser. 7: 215–233; Crea and Horn, 180, Nuc. Acids Res. 9(10): 2331; Matteucci and Caruthers, 1980, Tetrahedron Letters 21: 719; and Chow and Kempe, 1981, Nuc. Acids Res. 9(12): 2807–2817. Alternatively, the protein itself could be produced using chemical methods to synthesize the C100-R amino acid sequence in whole or in part. For example, peptides can be synthesized by solid phase techniques, cleaved from the resin, and purified by preparative high performance liquid chromatography. (E.g., see Creighton, 1983, Proteins Structures And Molecular Principles, W. H. Freeman and Co., N.Y. pp. 50–60). The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49.

5.2. Expression of the C100-R

In order to express a biologically active C100-R, the nucleotide sequence coding for C100-R, or a functional equivalent as described in Section 5.1 supra, is inserted into an appropriate expression vector, i.e., a vector which contains the necessary elements for the transcription and translation of the inserted coding sequence. The C100-R gene products as well as host cells or cell lines transfected or transformed with recombinant C100-R expression vectors can be used for a variety of purposes. These include but are not limited to generating antibodies (i.e., monoclonal or polyclonal) that bind to the receptor, including those that competitively inhibit binding and "neutralize" β-APP activity of βAPP or fragments of βAPP, and the screening and selection of β-APP analogs or drugs that act via the C100-R; etc.

5.2.1. Expression Systems

Methods which are well known to those skilled in the art can be used to construct expression vectors containing the C100-R coding sequence and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the C100-R coding sequence. These include but are not limited to microorganisms such as bacteria transformed with recombinant bacteriophage DNA, plasmid DNA or cosmid DNA expression vectors containing the C100-R coding sequence; yeast transformed with recombinant yeast expression vectors containing the C100-R coding sequence; insect cell systems infected with recombinant virus expression vectors (e.g., baculovirus) containing the C100-R coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the C100-R coding sequence; or animal cell systems infected with recombinant virus expression vectors (e.g., adenovirus, vaccinia virus) including cell lines engineered to contain multiple copies of the C100-R DNA either stably amplified (e.g., CHO/dhfr) or unstably amplified in double-minute chromosomes (e.g., murine cell lines).

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the C100-R DNA, SV40-, BPV- and EBV-based vectors may be used with an appropriate selectable marker.

In bacterial systems a number of expression vectors may be advantageously selected depending upon the use intended for the C100-R expressed. For example, when large quantities of C100-R are to be produced for the generation of antibodies, vectors which direct the expression of high levels of fusion protein products that are readily purified may be desirable. Such vectors include but are not limited to the E. coli expression vector pUR278 (Ruther et al., 1983, EMBO J. 2: 1791), in which the C100-R coding sequence may be ligated into the vector in frame with the lacZ coding region so that a hybrid C100-R/lacZ protein is produced; pIN vectors (Inouye & Inouye, 1985, Nucleic acids Res. 13: 3101–3109; Van Heeke & Schuster, 1989, J. Biol. Chem. 264: 5503–5509); and the like. Alternatively, pMT3 vectors may be used to express c-myc/C100-R fusion proteins. PGEX vectors may also be used to express foreign polypeptides as fusion proteins with glutathione S-transferase (GST). In general, such fusion proteins are soluble and can easily be purified from lysed cells by affinity chromatography, e.g., adsorption to glutathione-agarose beads followed by elution in the presence of free glutathione. The pGEX vectors are designed to include thrombin or factor Xa protease cleavage sites so that the cloned polypeptide of interest can be released from the GST moiety. See also Booth et al., 1988, Immunol. Lett. 19: 65–70; and Gardella et al., 1990, J. Biol. Chem. 265: 15854–15859; Pritchett et al., 1989, Biotechniques 7: 580.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II.

In cases where plant expression vectors are used, the expression of the C100-R coding sequence may be driven by any of a number of promoters. For example, viral promoters such as the 35S RNA and 19S RNA promoters of CaMV (Brisson et al., 1984, Nature 310: 511–514), or the coat protein promoter of TMV (Takamatsu et al., 1987, EMBO J. 6: 307–311) may be used; alternatively, plant promoters such as the small subunit of RUBISCO (Coruzzi et al., 1984, EMBO J. 3: 1671–1680; Broglie et al., 1984, Science 224: 838–843); or heat shock promoters, e.g., soybean hsp17.5-E or hsp17.3-B (Gurley et al., 1986, Mol. Cell. Biol. 6: 559–565) may be used. These constructs can be introduced into plant cells using Ti plasmids, Ri plasmids, plant virus vectors, direct DNA transformation, microinjection, electroporation, etc. For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7-9.

An alternative expression system which could be used to express C100-R is an insect system. In one such system, *Autographa californica* nuclear polyhidrosis virus (AcNPV) is used as a vector to express foreign genes. The virus grows in *Spodoptera frugiperda* cells. The C100-R coding sequence may be cloned into non-essential regions (for example the polyhedrin gene) of the virus and placed under control of an AcNPV promoter (for example the polyhedrin promoter). Successful insertion of the C100-R coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Viol. 46: 584; Smith, U.S. Pat. No. 4,215,051).

In mammalian host cells, a number of viral based expression systems may be utilized. In cases where an adenovirus is used as an expression vector, the C100-R coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing C100-R in infected hosts. (E.g., See Logan & Shenk, 1984, Proc. Natl. Acad. Sci. (USA) 81: 3655–3659). Alternatively, the vaccinia 7.5K promoter may be used. (E.g., see Mackett et al., 1982, Proc. Natl. Acad. Sci. (USA) 79: 7415–7419; Mackett et al., 1984, J. Virol. 49: 857–864; Panicali et al., 1982, Proc. Natl. Acad. Sci. 79: 4927–4931).

Specific initiation signals may also be required for efficient translation of inserted C100-R coding sequences. These signals include the ATG initiation codon and adjacent sequences. In cases where the entire C100-R gene, including its own initiation codon and adjacent sequences, is inserted into the appropriate expression vector, no additional translational control signals may be needed. However, in cases where only a portion of the C100-R coding sequence is inserted, exogenous translational control signals, including the ATG initiation codon, must be provided. Furthermore, the initiation codon must be in phase with the reading frame of the C100-R coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, Methods in Enzymol. 153: 516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, WI38, etc.

For long-term, high-yield production of recombinant proteins, stable expression is preferred. For example, cell lines which stably express the C100-R may be engineered. Rather than using expression vectors which contain viral origins of replication, host cells can be transformed with the C100-R DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media.

The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the C100-R on the cell surface, and which respond to βAPP-C100 mediated signal transduction. Such engineered cell lines are particularly useful in screening for βAPP-C100 analogs.

A number of selection systems may be used, including but not limited to the herpes simplex virus thymidine kinase (Wigler, et al., 1977, Cell 11: 223), hypoxanthine-guanine phosphoribosyltransferase (Szybalska & Szybalski, 1962, Proc. Natl. Acad. Sci. USA 48: 2026), and adenine phosphoribosyltransferase (Lowy, et al., 1980, Cell 22: 817) genes can be employed in tk$^-$, hgprt$^-$ or aprt$^-$ cells, respectively. Also, antimetabolite resistance can be used as the basis of selection for dhfr, which confers resistance to methotrexate (Wigler, et al., 1980, Natl. Acad. Sci. USA 77: 3567; O'Hare, et al., 1981, Proc. Natl. Acad. Sci. USA 78: 1527); gpt, which confers resistance to mycophenolic acid (Mulligan & Berg, 1981, Proc. Natl. Acad. Sci. USA 78: 2072); neo, which confers resistance to the aminoglycoside G-418 (Colberre-Garapin, et al., 1981, J. Mol. Biol. 150: 1); and hygro, which confers resistance to hygromycin (Santerre, et al., 1984, Gene 30: 147) genes. Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85: 8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

5.2.2. Identification of Transfectants or Transformants that Express the C100-R The host cells which contain the coding sequence and which express the biologically active gene product may be identified by at least four general approaches; (a) DNA-DNA or DNA-RNA hybridization; (b) the presence or absence of "marker" gene functions; (c) assessing the level of transcription as measured by the expression of C100-R mRNA transcripts in the host cell; and (d) detection of the gene product as measured by immunoassay or by its biological activity.

In the first approach, the presence of the C100-R coding sequence inserted in the expression vector can be detected by DNA-DNA or DNA-RNA hybridization using probes comprising nucleotide sequences that are homologous to the C100-R coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the C100-R coding sequence is inserted within a marker gene sequence of the vector, recombinants containing the C100-R coding sequence can be identified by the absence of the marker gene function. Alternatively, a marker gene can be placed in tandem with the C100-R sequence under the control of the same or different promoter used to control the expression of the C100-R coding sequence. Expression of the marker in response to induction or selection indicates expression of the C100-R coding sequence.

In the third approach, transcriptional activity for the C100-R coding region can be assessed by hybridization assays. For example, RNA can be isolated and analyzed by Northern blot using a probe homologous to the C100-R coding sequence or particular portions thereof. Alternatively, total nucleic acids of the host cell may be extracted and assayed for hybridization to such probes.

In the fourth approach, the expression of the C100-R protein product can be assessed immunologically, for example by Western blots, immunoassays such as radioimmuno-precipitation, enzyme-linked immunoassays and the like. The ultimate test of the success of the expression system, however, involves the detection of the biologically active C100-R gene product. A number of assays can be used to detect receptor activity including but not limited to β-APP binding assays; and β-APP biological assays using engineered cell lines as the test substrate.

5.2.3. Recovery of the C100-R

Once a clone that produces high levels of biologically active C100-R is identified, the clone may be expanded and used to produce large amounts of the receptor which may be purified using techniques well-known in the art including, but not limited to immuno-affinity purification, chromatographic methods including high performance liquid chromatography, affinity chromatography using immobilized ligand such as β-APP-C100 or analogs thereof bound to beads, immunoaffinity purification using antibodies and the like.

Where the C100-R coding sequence is engineered to encode a cleavable fusion protein, purification may be readily accomplished using affinity purification techniques. For example, a collagenase cleavage recognition consensus sequence may be engineered between the carboxy terminus of C100-R and protein A. The resulting fusion protein may be readily purified using an IgG column that binds the protein A moiety. Unfused C100-R may be readily released from the column by treatment with collagenase. Another example would be the use of pGEX vectors that express foreign polypeptides as fusion proteins with glutathionine S-transferase (GST). The fusion protein may be engineered with either thrombin or factor Xa cleavage sites between the cloned gene and the GST moiety. The fusion protein may be easily purified from cell extracts by adsorption to glutathione agarose beads followed by elution in the presence of glutathione. In this aspect of the invention, any cleavage site or enzyme cleavage substrate may be engineered between the C100-R sequence and a second peptide or protein that has a binding partner which could be used for purification, e.g., any antigen for which an immuno-affinity column can be prepared.

5.3. Generation of Antibodies That Define the C100-R

Various procedures known in the art may be used for the production of antibodies to epitopes of the recombinantly produced C100-R. Neutralizing antibodies i.e., those which compete for the βAPP-C100 binding site of the receptor are especially preferred for diagnostics and therapeutics. Such antibodies include but are not limited to polyclonal, monoclonal, chimeric, single chain, Fab fragments and fragments produced by an Fab expression library.

For the production of antibodies, various host animals may be immunized by injection with the C100-R including but not limited to rabbits, mice, rats, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies to C100-R may be prepared by using any technique which provides for the production of antibody molecules by continuous cell lines in culture. These include but are not limited to the hybridoma technique originally described by Kohler and Milstein, (Nature, 1975, 256: 495–497), the human B-cell hybridoma technique (Kosbor et al., 1983, Immunology Today, 4: 72; Cote et al., 1983, Proc. Natl. cad. Sci., 80: 2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81: 6851–6855; Neuberger et al., 1984, Nature, 312: 604–608; Takeda et al., 1985, Nature, 314: 452–454) by splicing the genes from a mouse antibody molecule of appropriate antigen specificity together with genes from a human antibody molecule of appropriate biological activity can be used.

Antibody fragments which contain specific binding sites of C100-R may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246: 1275–1281) to allow rapid and easy identification of monoclonal Fab fragments with the desired specificity to C100-R.

In a specific embodiment described herein, anti-C100-R peptide antibodies to two different epitopes of the predicted C100-R amino acid sequence were generated. The peptides SPAAPNKEATPPS (amino acids 212–223 of C100-R; 1AB1 (SEQ ID NO: 32)) and NTDRQRKKSKMTDEE (amino acids 235–249 of C100-R; 2AB1R (SEQ ID NO: 33)) were synthesized and injected into rabbits.

The resulting polyclonal serum was immunoaffinity purified and the antibodies were used to probe immunoblots of human and rat brain homogenates (FIG. 15A). The two antibodies recognized a protein that migrated at a molecular weight of 61 kDA in both human and rat brain. Antibody 2AB1R cross-reacted with an −80 kDa protein in rat brain. This 80 kDa protein may represent another member of the C100-R family, the product of yet-undiscovered alternatively spliced transcript from the C100-R gene, or an unrelated protein. Immunoabsorption of antibody 1AB1R with its cognate peptide (FIG. 15B, lane 1) but not with the 2AB1R peptide (lane 2) abolished its immunoreactivity with the 61 kDa band; similarly, immunoabsorption of antibody 2AB1R with the 2AB1R peptide 9 lane 4) but not with the 1AB1R peptide (lane 5) abolished its specific staining of the 61 kDa protein. Immunoblots of tissue that had been fractionated into soluble and integral membrane components revealed that C100-R is a soluble protein. Synaptic plasma membrane fractions were prepared from human fetal brain tissue. Immunoblot analysis of the fractions showed the C100-R and APP are associated with (although neither is restricted to) synaptic plasma membranes (FIG. 15C), suggesting that C100-R like APP is present in the synaptic terminal (Koo et al., 1990 Proc. Natl. Acad. Sci. USA 87: 1561–1565; Schubert et al., 1991 Brain Res. 563: 184–194; Moya et al., 1994 Dev. Biol.1 171: 597–603).

5.4. Anti-Sense RNA and Ribozymes

Also within the scope of the invention are oligoribonucleotide sequences, that include anti-sense RNA and DNA molecules and ribozymes that function to inhibit the translation of C100-R mRNA. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of the C100-R nucleotide sequence, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. Within the scope of the invention are engineered hammerhead motif ribozyme molecules that specifically and efficiently catalyze endonucleolytic cleavage of C100-R RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both anti-sense RNA and DNA molecules and ribozymes of the invention may be prepared by any method known in the art for the synthesis of RNA molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

5.5. Uses of the C100-R, DNA and Engineered Cell Lines

The C100-R DNA, antisense oligonucleotides and ribozymes, APP-R expression products, antibodies and engineered cell lines described above have a number of uses for the diagnosis and treatment of Alzheimer's Disease.

For example, the C100-R DNA sequence may be used in hybridization assays of biopsies or autopsies to diagnose abnormalities of C100-R expression; e.g., Southern or Northern analysis, including in situ hybridization assays. In therapeutic applications, antisense or ribozyme molecules designed on the basis of the C100-R DNA sequence may be utilized to block transcription and expression of the C100-R gene product. Alternatively, the C100-R DNA could be used in gene therapy approach to introduce the normal recombinant gene into the defective cells of an individual or to correct an endogenous mutation in order to reconstitute the C100-R and its function.

In another embodiment of the invention, antibodies specific for the C100-R may be used to determine the pattern of receptor expression in biopsy tissue, or for diagnostic imaging in vivo; in such applications, "neutralizing" antibodies may be preferred. For example, an antibody conjugated to an imaging compound could be administered to a patient to "map" the locations and distribution of the C100-R in vivo.

In another embodiment of the invention, the APP-R itself, or a fragment containing its BAPP-C100 binding site, could be administered in vivo. The free C100-R or the peptide fragment could competitively bind to β-APP and inhibit its interaction with the native receptor in vivo.

In yet another embodiment of the invention, the engineered cell lines which express the entire C100-R or its ligand binding domain may be utilized to screen and identify active βAPP-C100 agonists or antagonists. Alternatively, cell lines that endogenously express the C100-R may be used for this purpose; e.g., neuroblastoma cell lines such as SK-N-MC as exemplified herein may be used. βAPP-derived peptides, other peptides, synthetic compounds, natural products, and other sources of potentially biologically active materials can be screened in the following manners. The ability of a test compound to inhibit the binding of βAPP-C100 (which can be labelled e.g., with $^{35}$Met or a "flag" sequence or detected with antibodies to the peptide) to the C100-R, and thus its potential to act as either agonists or antagonists may be measured. As a source of the receptor either whole C100-R-expressing cells homogenates, or subcellular fractions may be used. The binding may be measured using standard receptor binding techniques, such as those described in Section 6.1.3. The ability of agents to prevent, or mimic, the effects of βAPP-C100 on signal transduction responses in the C100-R-expressing cells may be measured. For example, responses such as changes in cytosolic concentrations of calcium, activation of specific protein kinases, altered secretion of hormones or neurotransmitters, modulation of second messenger production, or changes in cellular metabolism may be monitored. These assays may be performed in whole cells or membrane preparations using conventional techniques developed for these purposes. In engineered cells or cell lines that respond to the toxic effects βAPP-C100, the ability of substances to induce or prevent the toxicity may be measured. Toxicity may be monitored as described in the literature (Yankner et al., 1989, Science 245: 417–420), or by other established techniques.

Transgenic animals that contain the C100-R DNA as the transgene may be engineered to determine the in vivo effects of the βAPP-C100 agonists or antagonists found in the above or other screens, or to profile other agents that are potentially therapeutic for Alzheimer's Disease.

Recently, computer generated models for ligand-receptor interactions have been developed, and in a specific embodiment of the invention, information derived from computer modeling of C100-R may be used for design of receptor agonist or antagonist. Changes made to C100-R sequences, using for example techniques for site directed mutagenesis, and expression of mutant receptors in cell lines may be used to further define the functional role of particular receptor regions and residues.

In an embodiment of the invention the C100-R and/or cell lines that express the C100-R may be used to screen for antibodies, peptides, organic molecules or other ligands that act as agonists or antagonists of neuronal signal transduction mediated by C100-R. For example, anti-C100-R antibodies capable of neutralizing the activity of βAPP-C100, may be used to inhibit C100-R function. Alternatively, screening of peptide libraries or organic compounds with recombinantly expressed soluble C100-R protein or cell lines expressing C100-R protein may be useful for identification of therapeutic molecules that function by inhibiting the biological activity of C100-R.

In an embodiment of the invention, engineered cell lines which express the entire C100-R coding region or its ligand binding domain may be utilized to screen and identify βAPP-C100 agonists or antagonists. Synthetic compounds, natural products, and other sources of potentially biologically active materials can be screened in a number of ways. The ability of a test compound to inhibit binding of βAPP-C100 to C100-R may be measured using standard receptor binding techniques, such as those described in Section 5.3.2. The ability of agents to prevent the βAPP signal transduction response resulting from βAPP-C100 binding to C100-R may be measured. For example, responses such as activation of C100-R kinase activity, modulation of second messenger production or changes in cellular metabolism may be monitored. These assays may be performed using conventional techniques developed for these purposes.

The ability of a test compound to modulate signal transduction through the C100-R system may also be measured in vivo. The ability of agents to prevent the effect of βAPP-C100 binding on signal transduction responses of C100-R expressing cells may be measured. For example, responses such as inhibition of neurotoxicity or decrease in accumulation of deposit-like structures resulting in formation of amyloid-like fibrils may be assayed.

5.5.1. Screening of Peptide Library with C100-R Protein or Engineered Cell Lines Random peptide libraries consisting of all possible combinations of amino acids attached to a solid phase support may be used to identify peptides that are able to bind to the ligand binding site of a given receptor or other functional domains of a receptor such as kinase domains (Lam, K. S. et al., 1991, Nature 354: 82–84). The screening of peptide libraries may have therapeutic value in the discovery of pharmaceutical agents that act to inhibit the biological activity of C100-R receptor through their interaction with the receptor.

Identification of molecules that are able to bind to the C100-R may be accomplished by screening a peptide library with recombinant soluble C100-R protein. Methods for expression and purification of C100-R are described in Section 5.2.1 and may be used to express recombinant full length C100-R or fragments of C100-R depending on the functional domains of interest. For example, the kinase and βAPP-C100 ligand binding domains of the C100-R may be separately expressed and used to screen peptide libraries.

To identify and isolate the peptide/solid phase support that interacts and forms a complex with C100-R, it is necessary to label or "tag" the C100-R molecule. The C100-R protein may be conjugated to enzymes such as alkaline phosphatase or horseradish peroxidase or to other reagents such as fluorescent labels which may include fluorescein isothyiocynate (FITC), phycoerythrin (PE) or rhodamine. Conjugation of any given label, to C100-R, may be performed using techniques that are routine in the art. Alternatively, C100-R expression vectors may be engineered to express a chimeric C100-R protein containing an epitope for which a commercially available antibody exist. The epitope specific antibody may be tagged using methods well known in the art including labeling with enzymes, fluorescent dyes or colored or magnetic beads.

The "tagged" C100-R conjugate is incubated with the random peptide library for 30 minutes to one hour at 22° C. to allow complex formation between and peptide species within the library. The library is then washed to remove any unbound C100-R protein. If C100-R has been conjugated to alkaline phosphatase or horseradish peroxidase the whole library is poured into a petri dish containing a substrates for either alkaline phosphatase or peroxidase, for example, 5-bromo-4-chloro-3-indoyl phosphate (BCIP) or 3,3',4,4'-diaminobenzidine (DAB), respectively. After incubating for several minutes, the peptide/solid phase-C100-R complex changes color, and can be easily identified and isolated physically under a dissecting microscope with a micromanipulator. If a fluorescent tagged C100-R molecule has been used, complexes may be isolated by fluorescent activated sorting. If a chimeric C100-R protein expressing a heterologous epitope has been used, detection of the peptide/C100-R complex may be accomplished by using a labeled epitope specific antibody. Once isolated, the identity of the peptide attached to the solid phase support may be determined by peptide sequencing.

In addition to using soluble C100-R molecules, in another embodiment, it is possible to detect peptides that bind to the receptor using intact cells. The use of intact cells is preferred for use with receptors that are multi-subunits or labile or with receptors that require the lipid domain of the cell membrane to be functional. Methods for generating cell lines expressing C100-R are described in Sections 5.2.1. and 5.2.2. The cells used in this technique may be either live or fixed cells. The cells will be incubated with the random peptide library and will bind to certain peptides in the library to form a "rosette" between the target cells and the relevant solid phase support/peptide. The rosette can thereafter be isolated by differential centrifugation or removed physically under a dissecting microscope.

As an alternative to whole cell assays for membrane bound receptors or receptors that require the lipid domain of the cell membrane to be functional, the receptor molecules can be reconstituted into liposomes where label or "tag" can be attached.

5.5.2. Screening of Organic Compounds With C100-R Protein or Engineered Cell Lines Cell lines that express C100-R may be used to screen for molecules that modulate C100-R activity or C100-R mediated signal transduction. Such molecules may include small organic or inorganic compounds, or other molecules that modulate C100-R activity or that promote or prevent the formation of βAPP-C100/C100-R complex. Synthetic compounds, natural products, and other sources of potentially biologically active materials can be screened in a number of ways.

The ability of a test molecule to interfere with βAPP-C100/C100-R binding and/or C100-R signal transduction may be measured using standard biochemical techniques.

Other responses such as activation or suppression of catalytic activity, phosphorylation or dephosphorylation of other proteins, activation or modulation of second messenger production, changes in cellular ion levels, association, dissociation or translocation of signalling molecules, or transcription or translation of specific genes may also be monitored. These assays may be performed using conventional techniques developed for these purposes in the course of screening.

Ligand binding to its cellular receptor may, via signal transduction pathways, affect a variety of cellular processes. Cellular processes under the control of the βAPP C100/C100-R signalling pathway may include, but are not limited to, normal cellular functions, proliferation, differentiation, maintenance of cell shape, and adhesion, in addition to abnormal or potentially deleterious processes such as axonal degeneration, unregulated cell proliferation, loss of contact inhibition, blocking of differentiation or cell death. The qualitative or quantitative observation and measurement of any of the described cellular processes by techniques known in the art may be advantageously used as a means of scoring for signal transduction in the course of screening.

Various embodiments are described below for screening, identification and evaluation of compounds that interact with the C100-R receptor, which compounds may affect various cellular processes under the control of the C100-R receptor signalling pathway.

The present invention includes a method for identifying a compound which is capable of modulating signal transduction, comprising:

(a) contacting the compound with C100-R, or a functional derivative thereof, in pure or semi-pure form, in a membrane preparation, or in a whole live or fixed cell;

(b) incubating the mixture of step (a) in the presence of βAPP-C100, for an interval sufficient for the compound to stimulate or inhibit the signal transduction;

(c) measuring the signal transduction;

(d) comparing the signal transduction activity to that of C100-R, incubated without the compound, thereby determining whether the compound stimulates or inhibits signal C100-R mediated transduction.

C100-R, or functional derivatives thereof, useful in identifying compounds capable of modulating signal transduction may have, for example, amino acid deletions and/or insertions and/or substitutions as long as they retain significant signal transducing capacity. A functional derivative of C100-R may be prepared from a naturally occurring or recombinantly expressed C100-R by proteolytic cleavage followed by conventional purification procedures known to those skilled in the art. Alternatively, the functional derivative may be produced by recombinant DNA technology by expressing parts of C100-R which include the functional domain in suitable cells. Functional derivatives may also be chemically synthesized. Cells expressing C100-R may be used as a source of C100-R, crude or purified, or in a membrane preparation, for testing in these assays. Alternatively, whole live or fixed cells may be used directly in those assays.

C100-R signal transduction activity may be measured by standard biochemical techniques or by monitoring the cellular processes controlled by the signal. To assess modulation of kinase activity, the test molecule is added to a reaction mixture containing C100-R and a substrate test. To assess modulation of kinase activity of the C100-R receptor, the test molecule is added to a reaction mixture containing the C100-R. The kinase reaction is then initiated with the addition of βAPP-C100 and ATP. An immunoassay is performed on the kinase reaction to detect the presence or absence of the phosphorylated tyrosine residues on the substrate or to detect phosphorylated tyrosine residues on autophosphorylated C100-R, and results are compared to those obtained for controls i.e., reaction mixtures not exposed to the test molecule.

The invention also includes a method whereby a molecule capable of binding to C100-R in a chemical or biological preparation may be identified comprising:

(a) immobilizing C100-R, or functional fragments thereof, to a solid phase matrix;

(b) contacting the chemical or biological preparation with the solid phase matrix produced in step (a), for an interval sufficient to allow the compound to bind;

(c) washing away any unbound material from the solid phase matrix;

(d) detecting the presence of the compound bound to the solid phase, thereby identifying the compound.

The above method may further include the step of:

(e) eluting the bound compound from the solid phase matrix, thereby isolating the compound.

The term "compound capable of binding to C100-R" refers to a naturally occurring or synthetically produced molecule which interacts with C100-R. Such a compound may directly or indirectly modulate C100-R signal transduction and may include molecules that are natively associated with the functional domains of C100-R. Examples of such compounds are (i) a natural substrate of C100-R; (ii) a naturally occurring molecule which is part of the signalling complex; and/or a naturally occurring signalling molecule produced by other cell types.

5.6. Use of C100-R or Ligands

Receptor/ligand interaction between C100-R and βAPP-C100 is believed to play an important role in the signalling system during neuronal signal transduction. Expression of βAPP-C100 peptide in primate cells results in production and accumulation of deposit-like structures that result in formation of amyloid structures indicating a role βAPP-C100 in development of neurodengeration in Alzheimer's disease.

In one embodiment of the invention, ligands for C100-R, the C100-R itself, or a fragment containing its βAPP-C100 binding site, could be administered in vivo to modulate neuronal signal transduction. For example, administration of the C100-R or a fragment containing the βAPP-C100 binding site, could competitively bind to βAPP-C100 and inhibit its interaction with the native C100-R in vivo to inhibit signal transduction. Alternatively, ligands for C100-R, including anti-C100-R antibodies or fragments thereof, may be used to modulate signal transduction. Antagonists of βAPP-C100 activity may be used to inhibit the development of Alzheimer's disease.

The particular peptides, proteins, organic compounds or antibodies that modulate C100-R signal transduction can be administered to a patient either by itself, or in pharmaceutical compositions where it is mixed with suitable carriers or excipient(s).

These agents may be formulated and administered systemically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, intraocular injections or intranasal. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Compositions comprising a compound of the invention formulated in a compatible pharmaceutical carrier may be prepared, placed in an appropriate container, and labelled for treatment of an indicated condition. Suitable conditions indicated on the label may include treatment of a tumor, such as a glioma or glioblastoma; and inhibition of angiogenesis.

Alternatively, other delivery systems for hydrophobic pharmaceutical compounds may be employed. Liposomes and emulsions are well known examples of delivery vehicles or carriers for hydrophobic drugs. Certain organic solvents such as DMSO also may be employed, although usually at the cost of greater toxicity.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the C100-R modulating compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

For any compound used in the method of the invention, the therapeutically effective dose can be estimated initially from cell culture assays. For example, a dose can be formulated in animal models to achieve a circulating concentration range that includes the IC50 as determined in cell culture (i.e., the concentration of the test compound which achieves a half-maximal inhibition of the neuronal signal transduction activity). Such information can be used to more accurately determine useful doses in humans.

A therapeutically effective dose refers to that amount of the compound that results in amelioration of symptoms of Alzheimers Disease or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1).

Dosage amount and interval may be adjusted individually to provide plasma levels of the active moiety which are sufficient to maintain the C100-R inhibitory effects.

Alternately, one may administer the compound in a local rather than systemic manner, for example, via injection of the compound directly into neural tissue, often in a depot or sustained release formulation.

Furthermore, one may administer the drug in a targeted drug delivery system, for example, in a liposome coated with a neuronal specific antibody. In such a case the liposomes will be targeted to and taken up selectively by the neuronal tissue.

In cases of local administration or selective uptake, the effective local concentration of the drug may not be related to plasma concentration.

6. EXAMPLES

The subsection below describes the initial characterization of an APP binding protein expressed on neuronally derived cells and the cloning and sequencing of a complementary DNA representing part of the rat C100-R. The deduced amino acid sequence of C100-R reveals several motifs shared in common between "B" type calcium channels, Ryanodine calcium channels, calreticulin and protein Serine/Threonine Kinases.

6.1. Material and Methods

6.1.1. In Vitro Translation of Flag-βAPP-C100

The following "flag" sequence-containing oligonucleotide (SEQ ID NOS: 34 and 35) (SEQ ID NO: 8) was synthesized and inserted into pGEM7, ACC ATG GAC TAC AAA GAC GAT GAC GAT AAA TCG AT MET ASP TYR LYS ASP ASP ASP ASP LYS SER. (Immunex; Prickett et al. 1989 BioTechniques 7: 580). In addition, prior to the MET codon, the ACC triplet gives a consensus sequence for eucaryotic translation start and the ClaI site after the flag sequence was added for cloning as was HindIII linker at the five prime end of the oligio. The pGEM7 flag construct was cut with SmaI and ClaI and the ClaI site was filled in. The BglII/SmaI fragment from βAPP-695 was cloned into this construct. Clones with the proper orientation were selected. This recombinant was utilized to make $^{35}$S-βAPP-C100 peptide in two ways. First, in the coupled transcription/translation system, TNT Coupled Reticulocyte Lysate System (Promega Corp.). Closed circular plasmid DNA was added to the lysate along with $^{35}$S-methionine (6 $\mu C_1$) following the recommended procedure. Second, in uncoupled reactions, the recombinant was linearized with Spe I, and 5 µg DNA was utilized to produce RNA in vitro (≈20–30µg) following the manufacturer's protocol (Promega Corp.). 1–5 µg of this RNA was translated in either a wheat germ or rabbit reticulocyte translation system according to manufacturer'protocol (Promega Corp.). The in vitro translations either had one-tenth volume of 100 mM N-acetyl glucosamine (Sigma) added, and were aliquotted and frozen at −80° C., and dialyzed prior to use; were aliquotted and frozen directly, then dialyzed and spin column purified prior to use (Boehringer-Mannheim); or were affinity purified using the commercially available Flag Antibody (CA$^{++}$-dependent binding M1 Ab, IBI) coupled to Affigel 10 (Biorad). Affinity chromatography was accomplished by passing the in vitro translations over the Affigel 10-coupled M1 antibody column (1 ml bed volume) equilibrated in PBS (120 mM NaCl, 2.7 mM KCl, 10 mM phosphate buffer, pH 7.4) with 0.5 mM CaCl$_2$. After thorough washing (5–10 column volumes), the peptide was eluted from the column with PBS with Na$_2$EDTA (2 mM). The peptide eluted as a sharp 0.7 ml peak. EDTA was removed by dialysis for use in binding or autoradiography. The flag-βAPP-C100 construct was sequenced and the product peptide from the in vitro translation analyzed for amino acid composition by mass spectroscopic techniques to confirm its identity.

6.1.2. Cell Culture

PC12 cells (ATCC) for the binding assays were grown in RPMI1640 supplemented with 10% heat-inactivated horse serum and 5% fetal bovine serum. T-175 flasks were seeded with $5 \times 10^5$ cells/ml in 60 ml of growth medium containing 10 ng/ml NGF. An additional 60 ml of this medium were added every 2 days until the cells were harvested (usually at 6 days). Where indicated, PC12 cells were cultured as above except in the absence of NGF. Cells were collected by centrifugation at 138× g for 8 minutes. The supernatant was discarded and the pellet resuspended in 5 ml of the growth medium. The cells were triturated 3 times through a 23 g needle attached to a 10 cc syringe to provide a single cell suspension or, at most, small cell aggregates. Trypan blue dye exclusion indicated that over 99% of the cells were viable.

SK-N-MC cells (ATCC) were grown in DME supplemented with 10% calf serum. The SK-N-MC cells were cultured as described for PC-12 cells except NGF is not included.

6.1.3. Binding to Cells

For βAPP-C100 binding experiments, PC-12 or SK-N-MC cells grown and prepared as described above, were counted, collected by low speed centrifugation (138× g), and resuspended in phosphate-buffered saline (PBS, pH 7.4) with 1% BSA and 1% glucose (PBG). An 0.08 ml volume of the cell suspension, containing $2 \times 10^6$ cells, was mixed with 0.01 ml of $^{35}$S-βAPP-C100 and 0.01 ml of PBG, or PBG containing either unlabeled βAPP-C100 or its vehicle. For kinetic and inhibition experiments, the concentration of $^{35}$S-βAPP-C100 was either 25 pM or 50 pM. For saturation experiments, the ligand concentration ranged from 15 pM to 6 nM. The mixture was incubated at 4° C. for 3 hours, unless otherwise indicated. At the end of the incubation period, the cells were pelleted by centrifugation at 138× g for 90 sec, the supernatant (containing the unbound ligand) was removed, and 0.2 ml of fresh, ice-cold PBG was added. The cells and fresh buffer were briefly agitated, and again centrifuged and suspended in fresh, ice-cold buffer as above. Finally, the cells were pelleted by centrifugation, filtered through BSA (0.1%) treated filters and washed with 4 1-ml rinses of ice-cold PBS with 0.1% BSA. The duration of the period between resuspension of the cells in fresh, ice-cold buffer and filtration of the cells was less than 10 min. In the dissociation experiments, and to collect a sample of bound ligand, the cells were incubated in the buffer added as the second wash for up to 3 hours to allow the bound ligand to dissociate. The cells were then pelleted by centrifugation and the supernatant (containing the bound ligand that had dissociated) was removed. The cells were then rewashed and harvested as described above. Radioactivity retained by filters was measured by scintillation counting. Nonspecific binding was taken as that occurring in the presence of excess (3.2 nM to 18 nM) βAPP-C100. Saturation data were analyzed by computer using commercially available software. The binding model that best fitted the experimental data was determined by F-test (p<0.05).

6.1.4. Binding Autoradiography

Sprague-Dawley rats were sacrificed by hypercapnia and placed on ice until their brains could be removed (less than an hour). The brains were rapidly frozen in isopentane chilled to −20° C. with dry ice and either used immediately or stored at −80° C. until use. The brains were affixed to the specimen holder of a cryostat and 25 μM coronal sections were collected onto gelatin-coated microscope slides. The sections were either frozen overnight at −80° C. or used immediately. The sections were air-dried at 4° C. and then reincubated with the binding buffer (PBS, 1% BSA) for 30 minutes at 4° C. This buffer was replaced by fresh buffer containing either the ligand alone ($^{35}$S-βAPP-C100, 0.01 nM) or the ligand with up to a 10-fold excess of unlabeled βAPP-C100 or its vehicle. The incubation was continued for 3 h at 4° C. The ligand-containing buffer was then removed and the sections were washed twice with fresh buffer (15 min. and 1 min., 4° C.). The sections were then dipped into ice cold distilled water 10 times and dried under a stream of air at room temperature. The sections were then apposed to a sheet of X-ray film for a period of 1 to 14 days and the film developed. Some sections were stained with Cresyl violet for identification of brain region. The optical densities of regions of the autoradiographs were determined quantitatively using an image analysis system.

6.1.5. Screening for the C100-R cDNA by Expression Cloning cDNA was constructed from embryonic day 18 rat brain mRNA according to the protocol of Neve et al. (1986; delineated in detail by Klickstein and Neve in *Current Protocols in Molecular Biology*). λgt11 libraries (rat brain cDNA library, RL Neve; human brain cDNA library, Clontech) were plated on Y1090 *E. coli* cells at 150,000 pfu/150 mm plate. Plates were incubated at 42° C. for 3 h, at which time plaques were just visible. Plates were overlaid with Schleicher and Schuell 132 mm nitrocellulose filters which had been saturated with 10 mM IPTG (isopropyl-β, D-thiogalactoside) and slightly air dried. Plates were set at 37° C. for 3 hours, and the first filter removed and placed in TBS (50 mM Tris, pH 7.7, 150 mM NaCl). A second, duplicate IPTG-soaked nitrocellulose filter was placed on the plate surface and left for two hours. The second filter was removed and placed in TBS. The filters were allowed to sit in TBS without blocking agent for at least 12 hours and up to four days to allow refolding. Filters were blocked in TBS with 5% nonfat skimmed milk for periods ranging from 2 h to overnight. Filters were washed in binding buffer (50 m Tris-HCl, Ph 7.7, 50 mM NaCl, 2 mM MgCl$_2$, 1 mM Dithiothreitol). Filters were incubated with in vitro translated $^{35}$S-βAPP-C100 at 3 nM for two hours at 4° C. Three 3 minutes washes (4° C.) were used to remove non-bound labeled peptide: (i) binding buffer alone, (ii) binding buffer +0.1% NP40, and (iii) binding buffer. Filters were immediately removed from the wash and air dried. The processed filters were exposed to X-OMAT RP film with a screen at −70° C. for 6 days to two weeks. It was found that wet plates were necessary to get sufficient protein/plaque to get significant signal. Also, throughout the procedure it was necessary to plate many more phage than routinely required at the comparable stage of purification for nucleic acid probes. Even when a "plaque"-pure phage population containing the βAPP-C100 binding protein site was plated as described above, only a low percentage of the plaques bound to the βAPP-C100, possibly due to the requirement of proper folding for binding.

Duplicate filters were compared to identify plaques expressing protein which bound to the $^{35}$S-βAPP-C100. Positive plaques were picked and taken through further rounds of binding and purification. Six rounds of isolation were required to obtain a single positive clone from a rat brain cDNA library. This rat clone is designated λAB1R. Five rounds of isolation were required to isolate five positive clones from a human brain cDNA library.

The insert from λAB1R was subcloned by PCR amplification using λgt11 sequencing primers which include restriction enzyme sites (Sal I and Not I). The amplified fragment was purified, cut with the restriction enzymes as per manufacturer's specifications and subcloned into SalI/NotI-cut Bluescript (SK+, Stratagene). The rat subclone was designated pAB1R-rat. This clone was subsequently used to screen additional rat brain cDNA libraries to isolate full length C100-R.

A second cloning strategy was developed utilizing the commercially available antibody to the "flag" tag. Libraries were plated, filter lifts produced, processed, probed and washed as described above with the exception that the βAPP-C100 was not labeled with $^{35}$S-methionine. Filters were cross-linked in a Stratalinker cross-linker (Stratagene) and blocked by 2 h incubation in TBS with 5% nonfat milk. The filters were then probed with a commercial anti-flag antibody at 10 μg/ml (M2, IBI) in TBS. Excess antibody was removed by three 10 minute washes in TBS (4° C.), with the middle wash solution supplemented with 0.1% NP40. Filters were incubated with a second antibody, goat anti-mouse IgG (heavy and light chain) biotin conjugate (NEN) in the same manner as with the first antibody. After washing, the filters were incubated with [$^{125}$I]-Avidin (NEN) at 0.5 μC$_i$/ml in binding buffer as above. The last three washes were in TBS with the middle wash including 0.1% NP40. Filters were air dried, and exposed to XOMAT-RP film with screen at −70° C. for 6 d to three weeks. Autoradiographs of the filters were compared for duplicates. Positive plaques were picked and carried through further rounds of screening.

Phage containing the human cognate of the βAPP-C100 binding protein were cloned by both the direct binding method and the flag-antibody method. These cDNAs have been subcloned and are being sequenced.

6.1.6. cDNA Characterization cDNAs were either subcloned into high copy plasmid vectors and transformed into bacteria or were amplified directly from the phage recombinants by the polymerase chain reaction. In the former case, double-stranded miniprep DNA was sequenced using Sequenase (U.S. Biochemicals); in the latter case, the PCR products were purified and sequenced with the femtomole sequencing system (Promega).

Sequencing of the clones was done by standard dideoxy methodology (Sequenase; USBiochem). Computer analysis was done primarily with GenePro (Riverside Scientific Enterprises) and PCGene (Intelligenics).

Southern transfers of human DNA or rat DNA (PC12) were probed with a $^{32}$P-labeled 260 bp fragment (EcoRI/ScaI) representing the 5' end of the AB1R cDNA. 8 μg of DNA was cut with various restriction enzymes, run on a 0.8% agarose gel, and transferred to nylon or nitrocellulose.

Northern analysis was carried out on total cellular RNA isolated with the guanidinium thiocyanate method (Chirgwin et al. 1979 Biochemistry 18 5294). Glyoxal gels, formaldehyde-agarose gels and dot blots were utilized to quantitate and evaluate the RNA under different conditions and from different sources (Tanzi et al., 1987, Science 235: 880–884; Tanzi et al., 1988, Nature 331: 528–530). RNA from PC12 cells treated with nerve growth factor for various periods of time, RNA from brains of patients with Alzheimer's Disease and Down's Syndrome, RNA from brain subregions, RNA from various developmental stages, etc. was run. Samples from AD or Downs brains were attained from the Children's Hospital (Boston) Pathology Dept. and from the McLean Hospital Brain Tissue Resource.

A lysogen of the 1985 bp AB1R cDNA in λgt11 was constructed in Y1089 by infecting Y1089 bacteria with the recombinant phage at a moi of 10,000:1, and identifying temperature sensitive clones from the unlysed bacteria. The lysogen was induced with heat and IPTG, and the resultant cell lysate resuspended in Laemmil gel sample buffer. A portion of the sample was electrophoresed on 10% PAGE, transferred to nitrocellulose, and incubated in successively more dilute concentrations of urea in PBS-Triton-X at 4° C. over two days after the method of Kageyama and Pastan (1989, Cell 59: 815). Binding to $^{35}$S-βAPP-C100 was then carried out according to the protocol used for isolating the AB1R clone from the cDNA libraries, with the change that PBS instead of TBS was used.

The cDNA insert from λAB1R was subcloned into the mammalian expression vector pCDNA1 in the antisense orientation, and PC12 cells were transfected by electroporation. These transient cells were grown in DME media for 3 d, treated with NGF and tested for their ability to bind $^{35}$S-labeled βAPP-C100. Stable transfectant cells were selected for by the inclusion of G418 in the media and neomycin resistant cells were subsequently tested in the binding assay for their ability to bind the labeled βAPP-C100 after treatment with NGF.

6.1.7. In Situ Hybridization Using βAPP-C100 Binding Protein Probe

Hybridization probes were prepared by labeling the pAB1R-rat construct linearized at various restriction sites. Anti-sense RNA probes were made from the plasmid template linearized at the NcoI site utilizing the T3 promoter of Bluescript, and sense-control RNA probes were made from the plasmid linearized at the BamHI site utilizing the T7 promoter of Bluescript. Probes were made in various ways. In vitro transcription was used to produce RNA probes. RNA was labeled with either $^{35}$S-UTP (Promega reagents) or Digoxigenin-UTP (Boehringer-Mannheim reagents). Digoxigenin-labeled DNA probes were produced by PCR (Lanzillo, 1991; M. McKenna and J. Carlson, personal communication); PCR primers were made to produce the appropriate fragments (Genosys Biotechnologies, Inc.).

Sections for in situ hybridization were prepared in the same manner as for binding autoradiography, only using RNAse free conditions. Prior to hybridization, the sections were given two 3 m washes with phosphate buffer (0.1 M) containing glycine (0.75 g/ml) followed by two 15 m washes with phosphate buffer alone. They were then treated with proteinase K (1 μg/ml in 15 mM Tris-HCl, pH 7.5 and 15 mM EDTA) for 30 m at 37° C. and washed with acetic acid anhydride (0.25% in 0.1 M triethanolamine, pH 7.5) for 10 m. This was followed by two 15 m washes with SSC (0.15 M NaCl, 0.015 M sodium citrate, pH 7.0) at twice its normal concentration (2x), defatting with EtOH and chloroform, and air drying. The hybridization probe, prepared as described above, was then placed onto the sections in a solution containing 50% formamide, 20x Denhardt's reagent, 300 μg/ml single stranded DNA, 150 μg/ml tRNA, 20 mM β-mercaptoethanol (BME), and 2x SSC. Coverslips were placed over the sections and hybridization solution and sealed to the slides with rubber cement. The hybridization was carried out overnight at 60° C. The coverslips were then removed and the sections were washed twice for 30 m at 60° C. with 4x SSC supplemented with 300 mM BME. Following this, they were treated with RNAse (20 μg/ml in 2x SSC, 20 m BME) for 30 m at 45° C. The sections were then washed four times with 2x SSC (60 m, 30 m, 30 m, and 30 m at 60° C.), washed one time with 1x SSC (30 m, 60° C.), and left overnight in 2x SSC. The following day the sections were quickly rinsed in 0.05 M phosphate buffer and then distilled water. They were then air dried and placed in contact with X-ray film. The films were developed 1 d to 2 weeks later and used to establish gross distribution of hybridized probe. Finer localization of the probe was achieved by coating the sections with a photoemulsion then developing the emulsion and measuring the grain densities over cell bodies in various brain regions.

6.1.8. Cloning of the Full Length RAT APP-4

In order to obtain the full-length C100-R the rat libraries were screened with various probes made from pAB1R-rat. These probes are specific for the most 5' sequence of the rat clone. After more rat sequence is available, subsequent rounds of screening will utilize probes specific to the most 5' sequence available at each round of screening. In addition, a second rat-brain cDNA library was constructed in λZAP (Stratagene) with a primer specific for the 5' region of the cDNA insert. The library was constructed using the RACE (rapid amplification of cDNA ends) protocol (Frohmann et al., 1988, Proc. Natl. Acad. Sci. USA 85: 8998–9002) with the following modifications: (1) The cDNA synthesis was primed with AB1RT3-1 or with AB1RT3-3, specific for the 3' UTR of the AB1R mRNA, instead of with oligo(dT). (2) The mRNA was denatured with methylmercury hydroxide prior to cDNA synthesis. (3) MMLV reverse transcriptase ("Superscript," Bethesda Research Labs) was used instead of AMV reverse transcriptase. (4) NotI adapters included at EcoRI linkers were attached to the ends of the cDNAs so that no subsequent digestion of the cDNA was necessary before cloning. The cDNAs were cloned into NotI digested, and partially filled in λ ZAP II, to make two libraries of approximately $10^5$ cDNA clones each. This library will be screened with probes specific for the most 5' sequence available at each round of cloning.

Another approach to cloning the full-length gene will be to utilize PCR technology. Using hippocampal messenger RNA we will use a primer specific for the 5' end of the cDNA insert and perform the reverse transcriptase reaction. The RNA/DNA hybrid will then be "tailed" with guanines by terminal transferase, the RNA digested with RNAse H and the second strand primed with a poly-C primer. By using primers with restriction sites incorporated into them, these "clone-specific" cDNAs will be cloned and sequenced. The process will be repeated through multiple rounds until the entire 11 kb sequence has been attained (Frohmann et al., 1988, Proc. Natl. Acad. Sci. USA 85: 8998–9002).

6.1.9. Precipitation Assays with βAPP-C100 GST Fusion

A cDNA fragment encoding APP-C100 was inserted in frame into the GST fusion protein vector pGEX-KG (Guan and Dixon, 1991, Anal. Biochem. 192: 262–267); full-length APP-695 and APP-751 cDNAs were inserted in frame into pGEX-1 (Smith and Johnson, 1988, Gene 67: 31-40). The resulting recombinants were transformed into CAG456, a htpR165 mutant that is defective in proteolysis (Baker et al., 1984 Proc. Natl. Acad Sci USA 81: 6779–6783). GST-APP fusion protein and control GST expression was induced with 0.1 mM IPTG at 32° C. for 2–5 hr. 200-ml cultures were pelleted and resuspended in homogenization buffer (100 mM NaCl, 1 mM EDTA, 10 mM Tris, pH 7.6, 10 μg/ml leupeptin, 10 μg/ml aprotinin, 1 mM DTT, 05 mg/ml lysosome) and held at 4° C. for 5 min, after which NP-40 was added to a final concentration of 10%. The suspension was homogenized and centrifuged, and the supernatant, containing soluble GST fusion protein, was retained. The fusion protein was bound to 300 μl of 50% glutathione beads that had been washed 3 times with 10 ml of wash buffer (100 mM NaCl, 1 mM CaCl$_2$, 10 mM Tris, 7.5, 5 mM DTT), by rocking the mixture at 4° C. overnight.

The GST-rhoA, -cdc42, and -rac1 plasmids were transformed into BL21 and fusion protein expression was induced with 50 μM IPTG at 37° C. for 4 hr. 100-ml cultures were pelleted and resuspended in ice-cold PBS+10 μg/ml aprotinin, 10 μg/ml leupeptin, 1 mM PMSF, 1 mM DTT and 3 mg/ml lysozyme, and held at room temperature for 15 min. Triton X-100 was added to a final concentration of 1%, and the suspension was sonicated and centrifuged. The supernatant, containing the soluble fusion proteins, was retained and incubated with 400 μl of a 50% slurry of glutathione agarose beads by incubating the mixture at 4° C. 1–3 hr with shaking.

For the precipitation assays, beads containing GST or GST fusion proteins were washed in binding buffer (20 mM Tris, pH 7.5, 1 mM DTT, 40 μg/ml BSA, 1 mM EDTA), resuspended as a 50% slurry in binding buffer (+0.5 mM GDPβS or GTPγS for the p21-GST fusions), and incubated at 37° C. for 20 min, after which MgCl$_2$ was added to a final concentration of 5 mM and the mixture incubated for 5 min at room temperature. 40 μl (for p21-GST pull-downs) or 30 ul (for APP-GST pull-downs) of in vitro translated $^{35}$S-N-Pak was added to 22–60 μl (varied to equalize protein; final volumes were brought to 60 μl with washed beads) of a 50% slurry of the appropriate GST fusion protein and the mixtures incubated at 4° C. for 1 hr or overnight with rocking. The beads were then washed 5 times with 1 ml each of PBS+0.5% NP-40 at 4° C., after which they were resuspended in 20 μl of 2x Laemmli buffer, boiled for 2 min, and subjected to 10% SDS-PAGE. The gels were stained with Coomassie blue to verify that equal amounts of GST fusion proteins had been loaded in the lanes, dried, and exposed to Hyperfilm MP (Amersham) for 1–10 days.

6.1.10. Immunoprecipitation and Activation of C100-R

Eight 60 mm dishes of subconfluent HEK 293T cells were transfected with 3 μg each of pJ3M-myc-N-Pak (myc epitope [EQKLISEEDL]-tagged C100-R cDNA in the expression vector pMT3 [ref]) by calcium phosphate precipitation. Each dish was incubated with the precipitated DNA for 12 hr, after which the cells were maintained in growth medium for a further 36 hr. The cells were serum starved for 16 hr, and then each dish was washed twice with ice cold PBS; cells were scraped into the second wash, centrifuged, and resuspended in buffer A (20 mM Tris, pH 7.5, 1 mM MgCl$_2$, 125 mM NaCl, 1% Triton X-100)+1 mM PMSF, 10 μg/ml leupeptin, 10 μg/ml aprotinin, 50 mM NaF, 100 μM Na$_3$VO$_4$. The extracts were centrifuged at 13,000 g for 10 min at 4° C., after which the supernatants were pooled and incubated for 2 hr at 4° C. with anti-myc antibody (9E10, 1:20) and protein A Sepharose (1:20). The beads were washed 3 times in PBS/1% Triton X-100 followed by one wash with buffer A, and then resuspended in 400 ul of buffer A.

GST-RhoA, -Cdc42, and -Rac1 were purified from transformed BL21 cells as described above. The fusion proteins were purified on glutathione beads, which were washed in buffer A+5 MM DTT. The GST-fusion proteins were then eluted with 20 mM Tris, pH 8.0, 150 mM NaCl, 10 mM glutathione, 5 mM DTT. The eluted protein was diluted in 300 µl of buffer C (20 mM Tris, pH 7.5, 1 mM DTT, 40 µM BSA, 1 mM EDTA) to a final concentration of 100 µg/ml. Either GDPβs OR GTPγS was added to a final concentration of 0.5 mM, and the mixtures were incubated at 37° C. for 20 min. Then $MgCl_2$ was added to a final concentration of 5 mM and each sample was incubated at 25° C. for a further 5 min.

Five µg of each nucleotide-bound GST-GTPase was added to 50 µl of purified myc-N-Pak/protein A Sepharose suspension, and incubated at 25° C. for 20 min. The mixtures were washed twice in buffer A and twice in kinase buffer (50 mM Tris, pH 7.4, 5 mM $MgCl_2$, 10 mM $MnCl_2$, 1 mM DTT). 30 µl of kinase buffer containing 0.1 µCi/µl [$\delta^{32}$P]-ATP, 25 µM ATP and 50 µM MPB were added to each sample, and the mixtures were incubated at 25° C. for 3 min. the phosphoproteins were separated by SDS-PAGE and identified and quantitated using a phosphorimager.

6.1.11. Antibodies and Immunoblots

The peptides SPAAPNKEATPPS (amino acids 212–223 of N-Pak; 1AB1R) and NTDRQRKKSKMTDEE (amino acids 235–249 of N-Pak; 2AB1R) were synthesized by Research Genetics using MAP resin technology. Antibodies were generated in rabbits, and the serum was immunoaffinity purified.

10 µg each of total human fetal or rat postnatal day (P)21 brain homogenate were subjected to 10% SDS-PAGE, and were transferred to PVDF (Millipore) membranes. The membranes were incubated in 0.2% I-block (Tropix, Bedford, Mass.) and 0.5% Tween-20 overnight at 4° C., then were incubated with a 1:1000 dilution of 1AB1R or a 1:2000 dilution of 2AB1R for 1 hr at room temperature. The membrane was washed and incubated with alkaline phosphatase-conjugated goat anti-rabbit IgG (1:10,000) for 1 hr, after which the manufacturer's (Tropix) protocol for chemiluminescent detection was followed. For the preabsorption experiments, each diluted antibody was incubated with 30 µg/ml of peptide overnight at 4° C. prior to being used for the immunoblots.

6.1.12. Synaptosomal Plasma Membrane Preparations

Synaptosomal plasma membrane (SPM) fractions were isolated from human brain specimens as described by Perrone-Bizzozero et al. (1988). Briefly, tissue was homogenized in 0.32 M sucrose, 50 mM Tris-HCl pH 7.4, and 0.1 mM PMSF in a glass Teflon homogenizer and fractionated by sucrose gradient centrifugation. SPMs were resuspended in buffer containing 10 mM Tris-HCl pH 7.4, 5 mM EGTA pH 7.4, and 5 mM $MgCl_2$ (TEM) and protein concentration was determined by the Coomassie Blue method using bovine serum albumin as a standard. Samples were stored at −80° C. at a concentration of 1 mg/ml.

6.1.13. RNA Blot Analysis

RNA was obtained from brain tissue and other organs of fetal abortuses. RNA was isolated from each tissue or brain region by the guanidinium thiocyanate procedure (Chirgwin et al., 1979, Biochemistry 18: 5294–5299) as modified by Neve et al. (1986, Mol. Brain Res. 1: 271–280). The amount of RNA purified from each tissue sample was determined by $OD_{260}$; $OD_{260/280}$ ratios were also determined to confirm uniformity of this ratio among the samples. For the human fetal tissue blot and the human/rat nervous system subregion blot, 20 µg of total RNA from each tissue was subjected to electrophoresis on agarose/formaldehyde gels, transferred to Biotrans membrane (ICN), and hybridized with radiolabeled probe as described previously (Neve et al., 1986, Mol. Brain Res. 1: 271–280). The blots were exposed to Kodak X-Omat AR film for 4 days (human fetal tissue) or 12 days (human/rat nervous system subregions). For the blot of the human fetal brain subregions, 10 µg of total RNA were loaded into each lane. The blot was exposed for 75 hours (n-pak probe) or 22 hours (APP probe). β-actin and cyclophilin cDNA probes were used as hybridization controls for the Northern blots, and confirmed equal loading of RNA in the lanes (Schwartz et al., 1994, Hum. Genet. 94: 658–664).

6.1.14. In Situ Hybridization Histochemistry

Tissues were fresh-frozen and cut in sections 12 µm thick on a cryostat. Sections were fixed in buffered 4% paraformaldehyde for 10 minutes at room temperature, rapidly air-dried, and stored desiccated at −70° C. At the time of use, sections were blocked with 0.1 M glycine, rinsed, and acetylated with 25% acetic anhydride in 0.1 M triethanolamine, pH 8.0. Sections were washed in 2× SSC and delipidated by treatment with ethanol and chloroform. Sections were then partially rehydrated and incubated overnight at 60° C. with 10,000 cpm/ul $^{35}$S-labeled riboprobes (synthesized using a template representing bp-24 to 230 of the cDNA) in a solution containing 50% formamide, 10% dextran sulfate, 20× Denhardt's solution, 300 µg/ml sheared salmon sperm DNA, 150 µg/ml tRNA, 2× SSC, and 20 mM β-mercaptoethanol. Sense and antisense riboprobes were generated using the Promega protocol. Following hybridization, sections were treated with RNAse A and were washed with increasing stringency (final stringency 0.1× SSC at 60° C.). Sections were dried, dipped in a 1:1 dilution of Kodak NTB2 emulsion with water, and developed after 5 weeks. Controls included hybridizations with sense strands.

6.2. Results

6.2.1. Radioligand Binding

Because βAPP-C100 is toxic to NGF-differentiated PC12 cells, we tested the binding of the in vitro synthesized βAPP-C100 fragment to the surface of PC12 cells that had been treated with NGF (Kozlowski et al. 1992 J. Neuroscience 12: 1679). $^{35}$S-βAPP-C100 binding to the differentiated PC12 cells was inhibitable by unlabeled βAPP-C100. Similar results were obtained with the neuroblastoma cell line, SK-N-MC (see FIG. 1).

In the NGF-treated PC-12 cells, the inhibitable fraction of the binding accounted for 40%–60% of the total binding. The $IC_{50}$ value for the inhibitable binding was 1.7±0.7 nM (n=5). Inhibitable binding reached a maximum after 3 hours of incubation and was completely dissociable (FIGS. 2A–2B). Saturation experiments indicated the presence of a single class of binding sites with a $K_d$ value of 0.81±0.37 nM, in approximate agreement with the $IC_{50}$ value determined above, and a $B_{max}$ value of 0.37±0.05 fmole/$10^6$ cells. Binding of $^{35}$S-βAPP-C100 to NGF-treated PC12 cells was not significantly inhibited by other peptides, including a number of tachykinins. In rat brain sections, the highest levels of specific binding were found in regions of the hippocampus and olfactory tubercle.

The amount of inhibitable $^{35}$S-βAPP-C100 binding was dependent upon the duration of exposure of the PC12 cells to NGF. PC12 cells that were not exposed to NGF showed little inhibitable binding, whereas those cultured in the presence of NGF for 4 or 6 days showed progressively greater amounts of binding. Another variable affecting binding was pH. The maximum amount of binding occurred at pH 7. Binding was only 25% of maximum at pH 6 and only 52% of maximum at pH 8.5.

To assess the stability of $^{35}$S-βAPP-C100 in the assay conditions, samples of both free ligand at the end of the incubation period (unbound) and ligand which had bound to the cells and been released were examined by SDS-polyacrylamide gel electrophoresis (PAGE). Before addition to the assay, most of the radioactivity was contained in a single band with an apparent molecular weight of 15 kDa. This represents monomer βAPP-C100. A small amount of material was also present in two additional diffuse bands. One migrated at approximately twice the molecular weight of the major band and possibly represents a dimer of βAPP-C100. The other band had a much higher molecular weight and may be an aggregate. The gel profile of the unbound ligand at the end of the incubation period was identical to that of the ligand before incubation, indicating that the ligand had not been degraded. Similarly, the ligand released from binding had the same profile as the ligand originally added, with the possible exception of a slight reduction in the amount of high molecular weight material. These data show that the binding of βAPP-C100 ligand does not cause its modification.

A mutation of the tyrosine in βAPP-C100, made to examine the importance of a consensus sequence for phosphotyrosine (Tyr$_{687}$ to Phe), produced a peptide that was not toxic to differentiated PC-12 cells. Phe$_{687}$-βAPP-C100 does not significantly inhibit $^{35}$S-βAPP-C100 binding at concentrations up to 14 nM (n=3), making it at least 20 times less potent a ligand at the βAPP-C100 binding site than the native form.

6.2.2. Cloning and Characterization of the C100-R

The autoradiographic signals from the $^{35}$S-βAPP-C100 binding to λgt11 plaques induced to express protein in the late lytic cycle were atypical and variable. We used the XOMAT-RP high resolution film and long exposures in order to establish clear duplicates on the autoradiographs (FIG. 3).

The size of the cDNA insert of the rat clone, λAB1R, was 1970 bp. The complete sequence is given in FIGS. 4A–4C (SEQ. ID. NOS: 1–2). The sequence given includes a portion of the β-gal gene derived from the vectors, λgt11 and Bluescript. The clone's open reading frame is not in register with the β-Gal gene, so the clone is being expressed as a nonfusion protein.

A number of additional rat cDNA clones have been isolated and sequenced (FIG. 9). The new sequence information extends, in the 5' direction, the coding region of C100-R represented in FIGS. 4A–4C. The * above nucleotide 686 in FIG. 9 represents the junction with the rat sequence depicted in FIGS. 4A–4C at nucleotide 40.

In addition, at least 3 full length cDNA clones involving the C100-R have been isolated and sequenced (FIG. 10). Sequence analysis of these clones revealed a 1632 bp open reading frame (FIG. 10) encoding a 544 amino acid protein with a calculated molecular mass of 60.7 kDa. A portion of the sequence of the cDNA was found to be homologous to that coding for the serine/threonine kinase domain of the yeast STE20 protein (Leberer et al., 1992, EMBO J. 11: 4815–4824; Ramer and Davis, 1993, Proc. Natl. Acad. Sci. USA 90: 452–456), with 67% identity over an interval of 683 bp at the 3' end of each coding sequence. A search of the protein database revealed that the putative neural APP binding protein (C100-R) was closely related to rat p65$^{PAK}$ (Pak1; Manser et al., 1994) and yeast STE20 proteins (FIGS. 12A–12B), with highest homology in the serine/threonine kinase domain (70% between C100-R and STE20; >90% between C100-R and Pak1 [p65$^{PAK}$]). In addition, these three kinases shared, in their N-terminal domains, a peptide motif representing the Cdc42/Rac1-binding domain of Pak1 (FIG. 12A). The overall identity between C100-R and Pak1 protein sequences was 83%. Pak1 is a serine/threonine protein kinase that is activated by the Rho family p21 proteins Cdc42 and Rac1. The very close similarity between C100-R and Pak1 suggests an analogous function for C100-R.

At least four spliced forms of C100-R mRNA were identified. All diverged within the 5' UTR, at bp-27 (FIG. 10). No C100-R transcripts showing alternative splicing within the coding sequence were found.

6.2.3. In Vitro Binding of C100-R to APP, APP-C100 and Activated CDC42 and RAC1

A cDNA encoding full-length C100-R was used as template for the synthesis of C100-R RNA in vitro. The RNA was translate din a wheat germ lysate in vitro translation system, and the synthesis of the expected $^{35}$S-labeled 61 kDa protein was verified by SDS-polyacrylamide gel electrophoresis (SDS-PAGE; data not shown). In "pull-down" assays, glutathione S-transferase (GST) fusion proteins (Smith and Johnson, 1988, Gene 67: 31–40) of APP-695, APP-751, and APP-C100, and of the p21 proteins RhoA, Cdc42 and Rac1 were immobilized on glutathione-agarose beads and incubated with the in vitro-synthesized radiolabeled C100-R. The beads were pelleted, washed, and subjected to SDS-PAGE. Autoradiograms of the gels, shown in FIG. 3, demonstrate the precipitation of radiolabeled C100-R by GST-APP-695 and GST-APP-C100. GST-APP-751 also precipitated radiolabeled C100-R. The p21 proteins act as molecular "switches", active when bound to GTP and inactive when bound to GDP. The Cdc42 and Rac1 GST fusion proteins precipitated C100-R when complexed with GTP and therefore in an active state, but not when bound to GDP. The RhoA GST fusion protein did not precipitate C100-R, whether in an active or an inactive configuration; and GST alone failed to precipitate C100-R.

To determine whether association of C100-R with GTP-bound Cdc42 or Rac1 stimulated its kinase activity, we expressed it with an N-terminal myc epitope (myc-C100-R) in HEK 293T cells, immunoprecipitated it with a monoclonal anti-myc antibody, and incubated it with myelin basic protein (MBP) in the presence of [τ$^{32}$P]-ATP and GDP- or GTP-bound RhoA, Cdc42, and Rac1 GST fusion proteins (FIG. 14A). Consistent with the results obtained for Pak1 by Manser et al. (1994), MBP was phosphorylated by myc-N-Pak in the presence of GTP- but not GDP-bound Cdc42 or Rac1. MBP was not phosphorylated in the absence of N-Pak (lane a) or in the presence of RhoA, whether it was associated with GTP or GDP. These data are quantitated in FIG. 14B.

To determine the tissue specificity of C100-R mRNA expression, its cDNA was used to probe an RNA blot containing RNA from a range of human fetal (20–22 week) tissues (FIG. 16A). An approximately 11 kb mRNA was detected only in the brain, suggesting that expression of the C100-R gene is restricted to the nervous system. Analysis of the expression of C100-R mRNA in subregions of human fetal (20 week) brain (FIG. 16B) shows that it is expressed at high levels in the thalamus, primary motor cortex (Brodmann area (A)4), frontal cortex (A10), and visual cortex (A17/18). C100-R mRNA is expressed at moderate levels in the hippocampus, caudate-putamen, and primary somatosensory cortex (A1), and at very low levels in the cerebellum. Notably, the pattern of expression of APP mRNA in human fetal brain is similar to that of C100-R (FIG. 16B). The expression of C100-R mRNA in the adult human brain is slightly lower than that in the fetal brain. Northern blot analysis of regions of the human and rat nervous systems revealed robust expression of C100-R in fetal and adult rat spinal cord, and detectable but low expression in human retina and rat pituitary (FIG. 16B).

The very large size of the C100-R mRNA (~11 kb) relative to the 1632 bp that encode its protein product suggests that the mRNA contains long untranslated regions (UTRs). RACE (Rapid Amplification of cDNA Ends) analysis of the 5' ends of the C100-R mRNAs have identified 5'UTR regions of the alternatively spliced C100-R mRNA 3'UTR is, however, unusually long. One of our cDNA clones possesses over 3 kb of 3'UTR and yet does not extend to the polyadenylation site, indicating that the C100-R 3'UTR is greater than 3 kb in length.

Southern analysis of human and rat genomic DNA demonstrates that AB1R cDNA hybridizes to a small number of bands, which is consistent with the AB1R representing a single copy gene (FIG. 6). A strongly hybridizing 3.0 kb band was observed as well as two more weakly hybridizing bands, one at 8.5 kb and a high molecular weight band between 25 and 30 kb. depending on species.

6.2.4. In Situ Hybridization

In rat brain section, levels of hybridization greater than background were obvious only in the hippocampus and olfactory tubercle (FIGS. 8A–8B). This agrees with the distribution of binding sites as determined autoradioagraphically (FIGS. 7A–7B).

To further localize C100-R mRNA in the rat brain, in situ hybridization was carried out using an antisense riboprobe corresponding to the region of C100-R cDNA that shares at least homology with the pak-1 cDNA. Consistent with the robust expression of C100-R mRNA observed on blots, the expression of C100-R mRNA in rat brain was widespread (FIG. 17A) and was similar to that previously shown in the human fetal brain using RNA blots (see above). Very high levels of C100-R mRNA were observed in brain regions including the hippocampus, amygdala, piriform and entorhinal cortex, and olfactory bulb. A robust signal was also observed in discrete brainstem nuclei, including the raphe nucleus. Moderate levels of signal were found in neocortex and thalamus. In some brain regions with an overall low level of signal, including the caudate nucleus, dispersed intensely-labeled cells were nonetheless observed. The cerebellum was devoid of detectable signal. Control hybridizations with sense riboprobe gave no specific signal (not shown).

To determine whether C100-R mRNA was localized outside the brain, in situ hybridization of antisense C100-R riboprobe to coronal sections of embryonic day (E) 18 rats was carried out. C100-R mRNA was found in spinal cord and dorsal root ganglia, as well as in brain (FIG. 17B), suggesting that it is expressed in both the central and peripheral nervous systems. Non-neural tissues, including gut, bone, and muscle, were not labeled.

7. EXAMPLE

Cloning of Human C100-R

An adult human hippocampal cDNA library in lambda ZAP 11 (Stratagene) was screened using a labeled fragment from the rat C100-R cDNA insert. The labeled fragment is represented as the EcoRI fragment, from nucleotide 31 through 409, in FIG. 9. The rat C100-R EcoRI fragment was labeled using a random priming reaction and the library was screened under stringent conditions using methods routinely employed by one skilled in the art. For a review of screening strategies see e.g. Maniatis, 1989, Molecular Cloning, A Laboratory Manual, Cold Spring Harbor Press, N.Y. Several clones were obtained, ranging from 600 to 1500 base pairs in length. Results from partial sequencing of the 1500 base pair clone is shown in FIG. 18. Regions of sequence homology between the human C100-R sequence and the rat C100-R sequence are depicted in FIGS. 19A and 19B.

8. DEPOSIT OF MICROORGANISMS

The following microorganisms have been deposited with the American Type Culture Collection, (ATCC), Rockville, Md. and have been assigned the following accession numbers:

| Microorganism | Date of Deposit | Accession No. |
| --- | --- | --- |
| pABIR-rat | August 7, 1992 | 69047 |

The present invention is not to be limited in scope by the microorganisms deposited since the deposited embodiments are intended as illustrations of single aspects of the invention and any microorganisms which are functionally equivalent are within the scope of the invention.

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those skilled in the art from the foregoing description and accompanying drawings. Such modifications are intended to fall within the scope of the appended claims.

It is also to be understood that all base pair sizes given for nucleotides are approximate and are used for purposes of description.

What is claimed is:

1. An isolated nucleic acid molecule comprising (a) a nucleotide sequence that encodes a polypeptide having the amino acid sequence of SEQ ID No. 19; or (b) the full length complement of the nucleotide sequence of (a).

2. An isolated nucleic acid molecule comprising the nucleotide sequence of SEQ ID No. 18.

3. An isolated nucleic acid sequence consisting of a nucleotide sequence selected from the group consisting of SEQ ID No.: 26, SEQ ID No.: 27 and SEQ ID No.: 28.

4. A recombinant vector comprising the nucleotide sequence of claim 1, 2 or 3.

5. An isolated genetically engineered host cell comprising the recombinant vector of claim 4.

6. An expression vector comprising the nucleotide sequence of claim 1 or 2 operatively associated with a regulatory nucleotide sequence containing transcriptional and translational regulatory information that controls expression of the nucleotide sequence in a host cell.

7. An isolated genetically engineered host cell comprising the expression vector of claim 6.

8. The isolated genetically engineered host cell of claim 5 or 7 in which the host cell is prokaryotic.

9. The isolated genetically engineered host cell of claim 5 or 7 in which the host cell is eukaryotic.

10. A method for producing recombinant C100-R, comprising:

(a) culturing a host cell transformed with the expression vector of claim 6 and which expresses the C100-R; and (b) recovering the C100-R product from the cell culture.

11. The expression vector of claim 6 which is a fusion protein vector.

12. A method for producing recombinant C100-R fusion protein, comprising:

(a) culturing a host cell transformed with the expression vector of claim 11 and which expresses the C100-R fusion protein; and (b) recovering the C100-R fusion protein product from the cell culture.

* * * * *